(12) United States Patent
Haldar et al.

(10) Patent No.: US 10,597,696 B2
(45) Date of Patent: Mar. 24, 2020

(54) DETECTION OF NIEMANN-PICK DISEASE COMPRISING DETECTION OF LYSOZYME AND CATHEPSINS

(71) Applicant: UNIVERSITY OF NOTRE DAME DU LAC, Notre Dame, IN (US)

(72) Inventors: Kasturi Haldar, Chicago, IL (US); Md. Suhail Alam, Mishawaka, IN (US)

(73) Assignee: University of Notre Dame du Lac, South Bend, IN (US)

( * ) Notice: Subject to any disclaimer, the term of this patent is extended or adjusted under 35 U.S.C. 154(b) by 0 days.

(21) Appl. No.: 15/022,928

(22) PCT Filed: Sep. 18, 2014

(86) PCT No.: PCT/US2014/056417
§ 371 (c)(1),
(2) Date: Mar. 17, 2016

(87) PCT Pub. No.: WO2015/042326
PCT Pub. Date: Mar. 26, 2015

(65) Prior Publication Data
US 2017/0044590 A1 Feb. 16, 2017

Related U.S. Application Data

(60) Provisional application No. 61/879,529, filed on Sep. 18, 2013.

(51) Int. Cl.
*C12Q 1/37* (2006.01)
*C12Q 1/34* (2006.01)
*G01N 33/68* (2006.01)
*C12Q 1/6883* (2018.01)

(52) U.S. Cl.
CPC ............... *C12Q 1/37* (2013.01); *C12Q 1/34* (2013.01); *C12Q 1/6883* (2013.01); *G01N 33/6896* (2013.01); *C12Q 2600/136* (2013.01); *C12Q 2600/158* (2013.01); *G01N 2333/936* (2013.01); *G01N 2333/96466* (2013.01); *G01N 2500/00* (2013.01); *G01N 2800/28* (2013.01); *G01N 2800/52* (2013.01)

(58) Field of Classification Search
None
See application file for complete search history.

(56) References Cited

U.S. PATENT DOCUMENTS

| 2005/0071088 A1* | 3/2005 | Landfield | C12Q 1/6809 |
| | | | 702/20 |
| 2005/0118665 A1* | 6/2005 | Zhou | C12Q 1/00 |
| | | | 435/23 |
| 2006/0270835 A1 | 11/2006 | Berthet et al. | |
| 2009/0131265 A1 | 5/2009 | Zhang | |
| 2011/0009343 A1 | 1/2011 | Findeis et al. | |
| 2011/0195873 A1* | 8/2011 | Selinfreund | C12Q 1/40 |
| | | | 506/39 |
| 2013/0183662 A1 | 7/2013 | Zychlinsky et al. | |

FOREIGN PATENT DOCUMENTS

WO  WO 99/49317  * 9/1999 ............ G01N 33/68

OTHER PUBLICATIONS

Boman et al., Journal of Parkinson's Disease, 2016; 6: 307-315 (Year: 2016).*
Mullane and Williams, Biochemical Pharmacology, 2013; 85: 289-305 (Year: 2013).*
Maarup et al., Molecular Genetics and Metabolism, 2015; 116: 75-79. (Year: 2015).*
Alam et al., PLOS ONE, Oct. 2012; 7: e48273; 17 pages total. (Year: 2012).*
Pipalia et al., PNAS, 2011; 108: 5620-5625. (Year: 2011).*
Cluzeau et al., Human Molecular Genetics, 2012; 21: 3632-3646 (Year: 2012).*
Sleat et al., Proteomics 2012, 12, 3499-3509 (Year: 2012).*
Hastings et al., Molecular Genetics and Metabolism, 2012; 105: S15-S69, p. S34: doi:10.1016/j.ymgme.2011.11.072 (Year: 2012).*
"International Search Report PCTUS2014056417", dated Mar. 20, 2015, 5, ISA/USPTO, Alexandria, United States of America.
"Written Opinion of the International Search Authority PCTUS2014056417", dated Mar. 20, 2015, 7, ISA/USPTO, Alexandria, United States of America.
"International Preliminary Report on Patentability PCTUS2014056417", dated Mar. 22, 2016, 8, The International Bureau of WIPO, Geneva, Switzerland.
Maes, "Evidence for inflammation and activation of cell mediated immunity in Myalgic Encephalomyelitis/Chronic Fatigue Syndrome (ME/CFS): increased interleukin-1, tumor necrosis factor-alpha, PMN-elastase", 7, J. Affect. Disord, 2012.
Booth et al., "Instability. unfolding and aggregation of human lysozyme variants underlying amyloid fibrillogenesis", 7, Nature, vol. 385127, p. 787-793, Feb. 1997.
Vina et al., "Why women have more Alzheimer's disease than men: gender and mitochondrial toxicity of amyloid-beta peptide", 1, J Alzheimers Dis, http://www.ncbi.nlm.nih.gov/pubmed/20442496 Accessed on Mar. 3, 2015.
"PCT Third Party Observation PCTUS2014056417", Aug. 2, 2015, 5.
Vina et al., "Why women have more Alzheimer's disease than men: gender and mitochondrial toxicity of amyloid-beta peptide", 7, J Alzheimers Dis, vol. 20, p. S527-S533, 2010.

* cited by examiner

*Primary Examiner* — Christina M Borgeest
(74) *Attorney, Agent, or Firm* — Haukaas Fortius PLLC; Michael H. Haukaas

(57) ABSTRACT

Provided herein are methods for detecting an increased probability or risk of neurodegeneration in a subject. In some embodiments the method comprises assaying a sample from the subject for lysozyme and/or cathepsin S and detecting the lysozyme and/or cathepsin S from the sample, wherein an increased lysozyme and/or cathepsin S compared to levels in a control subject sample indicate an increased probability or risk of neurodegeneration. Methods of treatment and screening assays for determining drug effectiveness are also provided herein.

8 Claims, 36 Drawing Sheets

Total number of molecules present in each function is represented

FIG. 7
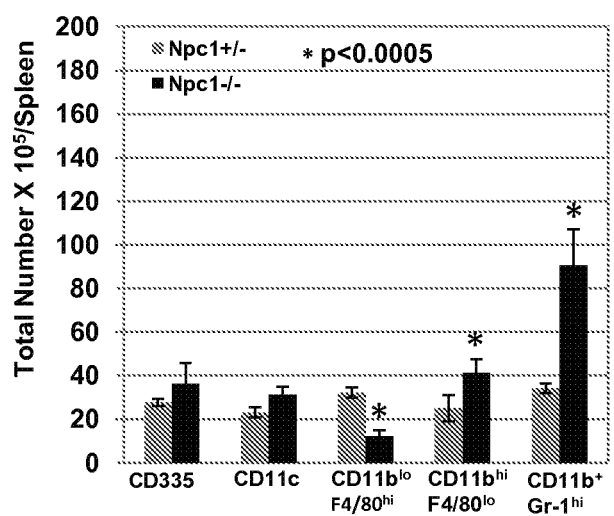
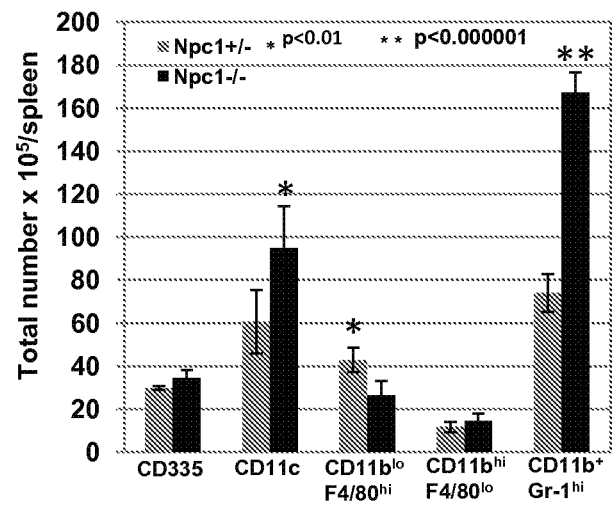

FIG. 8A-B
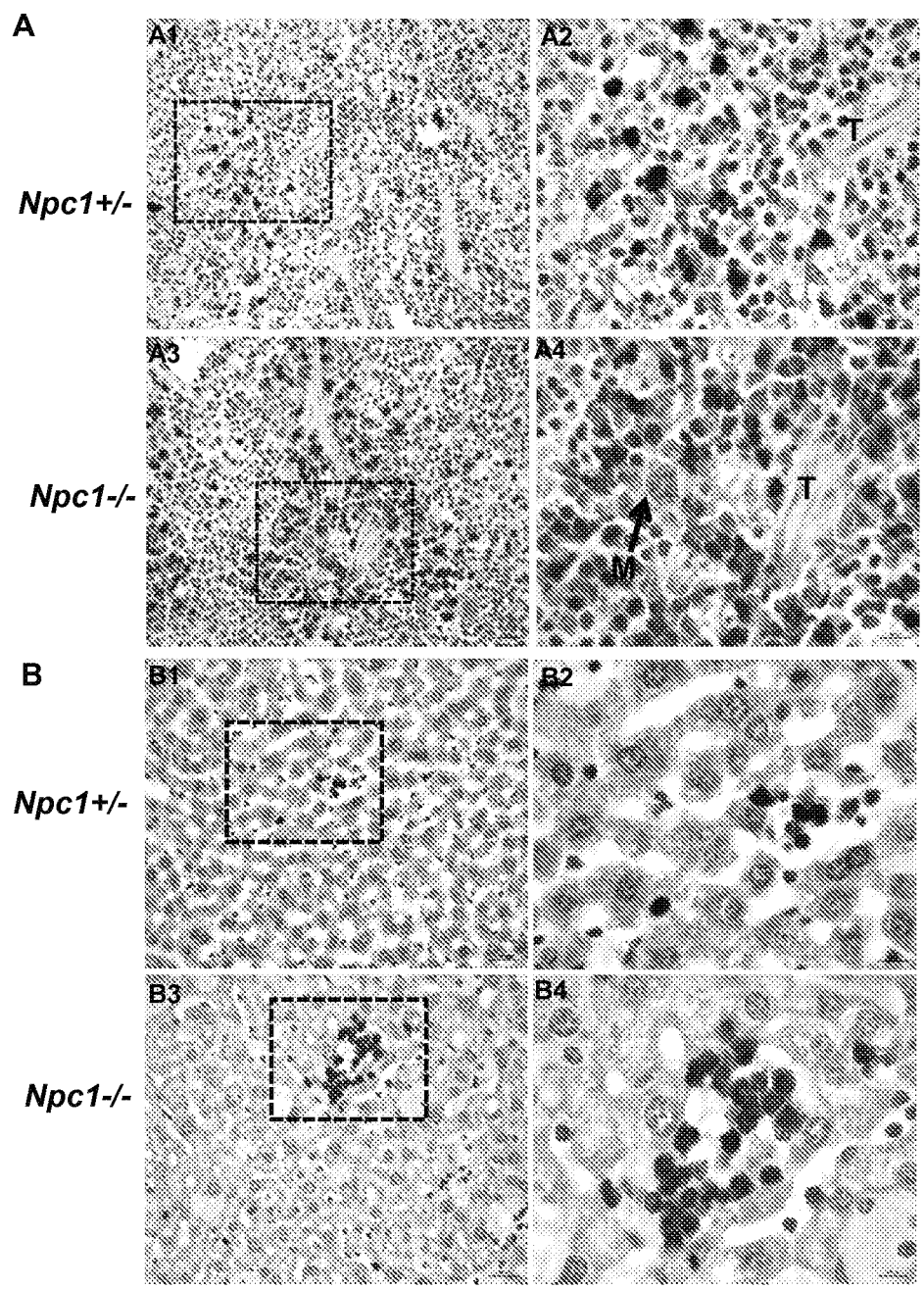

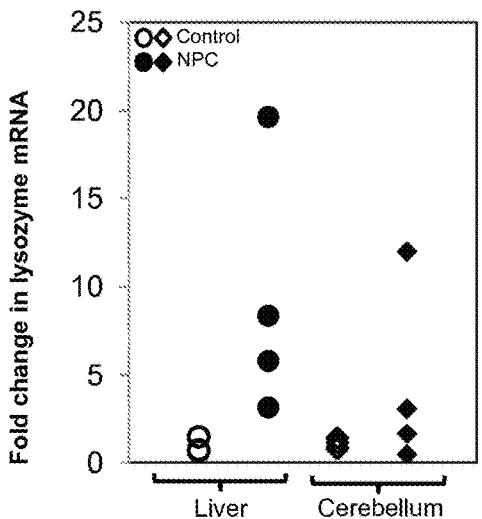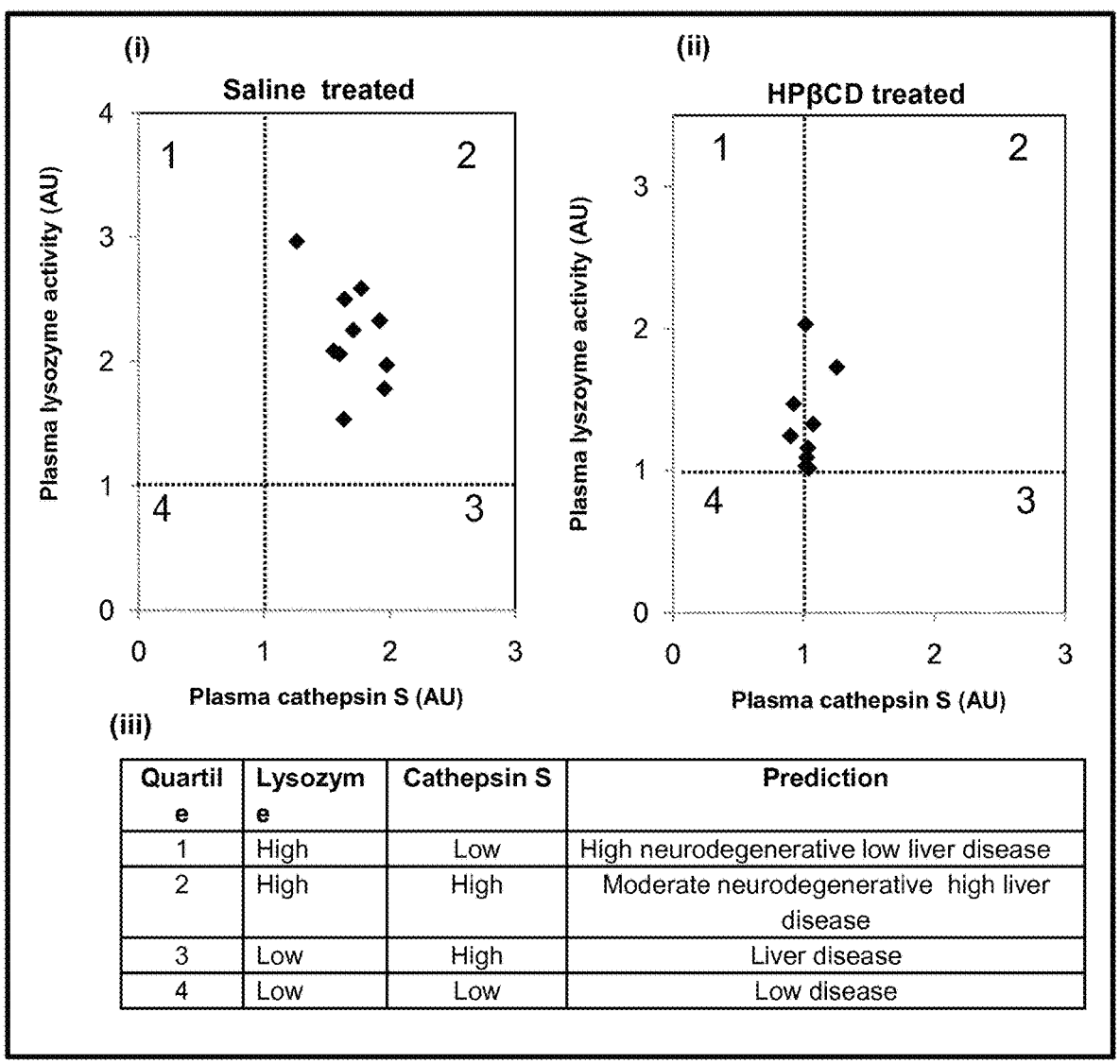
FIG. 20

Ratio of plasma cathepsinS and lysozyme level in Alzheimer patients

FIG. 28

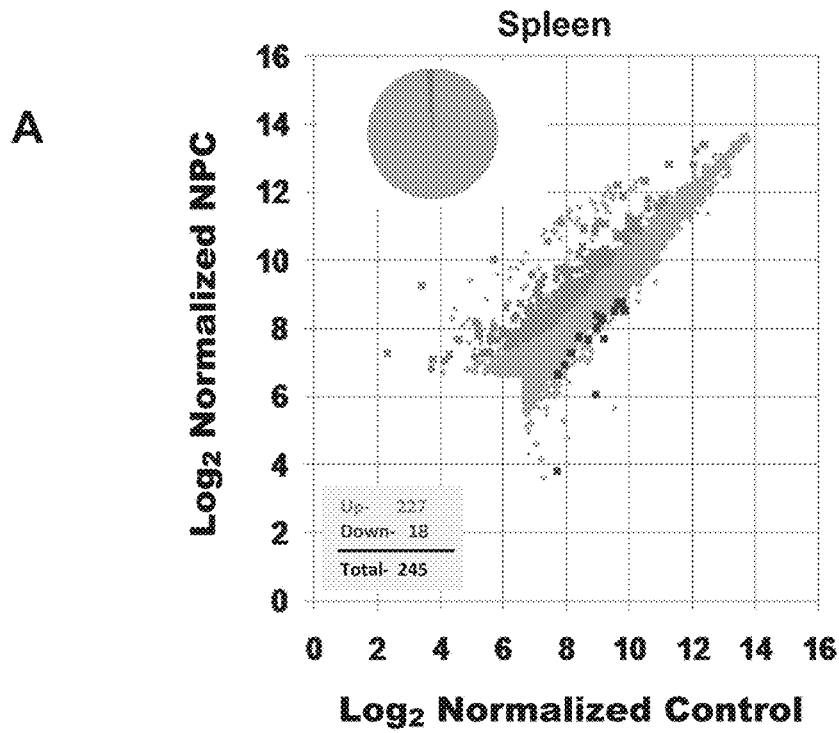

B

| Gene | Fold up regulation |
|---|---|
| Atp6v0d2: ATPase, H+ transporting, lysosomal V0 subunit D2 | 58.08 |
| Gpnmb: glycoprotein (transmembrane) nmb | 19.98 |
| Hal: histidine ammonia lyase | 10.06 |
| Clec7a: C-type lectin domain family 7, member a | 9.7 |
| Gm11428: predicted gene 11428 | 8.84 |
| Trim29: tripartite motif-containing 29 | 8.65 |
| Atf3: activating transcription factor 3 | 8.37 |
| Mmp12: matrix metallopeptidase 12 | 8.24 |
| Ahnak2: AHNAK nucleoprotein 2 | 7.64 |
| Dnahc2: dynein, axonemal, heavy chain 2 | 7.55 |
| Cdkn1c: cyclin-dependent kinase inhibitor 1C (P57) | 6.84 |
| Mm.138637.1 | 6.23 |
| Ms4a7: membrane-spanning 4-domains, subfamily A, member 7 | 6.21 |
| Fabp5: fatty acid binding protein 5 | 6.1 |
| 9430019H13Rik: RIKEN cDNA 9430019H13 gene | 5.88 |
| Msr1: macrophage scavenger receptor 1 | 5.86 |
| Anpep: alanyl (membrane) aminopeptidase | 5.05 |
| Elane: elastase, neutrophil expressed | 4.68 |
| F10: coagulation factor X | 4.56 |
| Ms4a3: membrane-spanning 4-domains, subfamily A, member 3 | 4.52 |

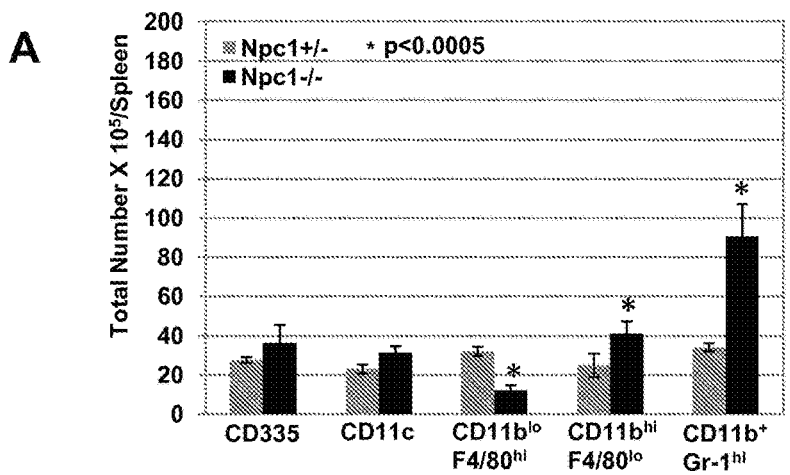
FIG. 29
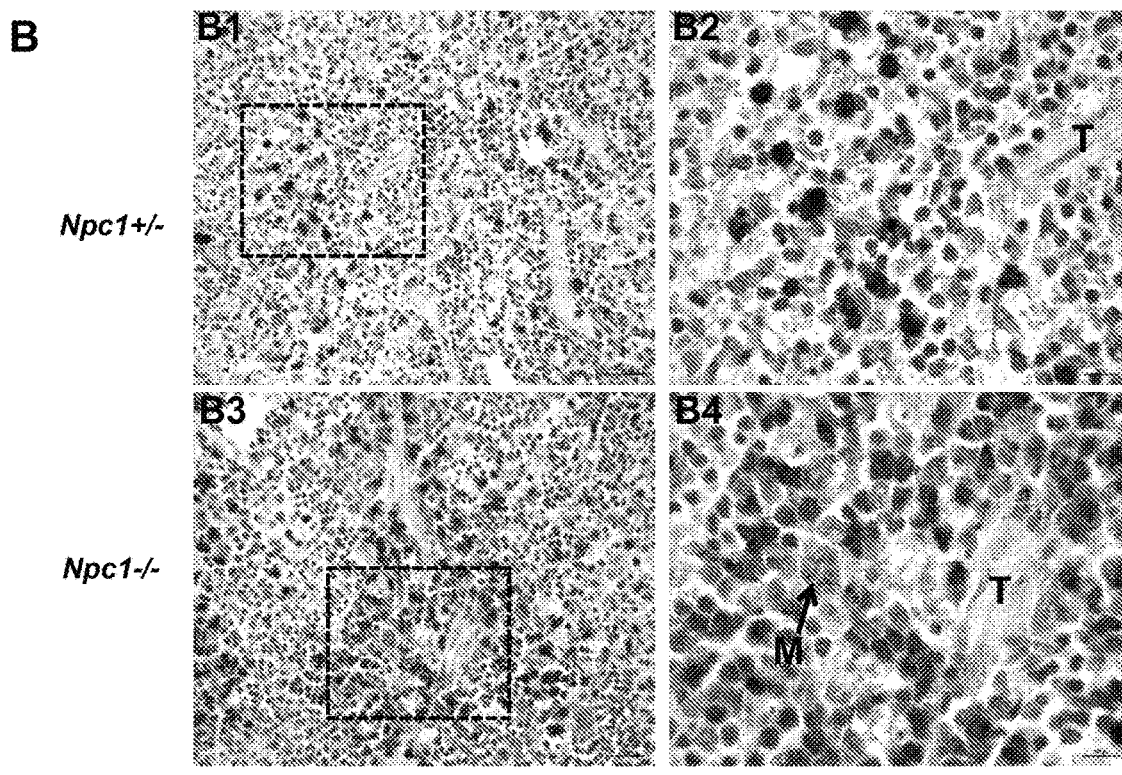
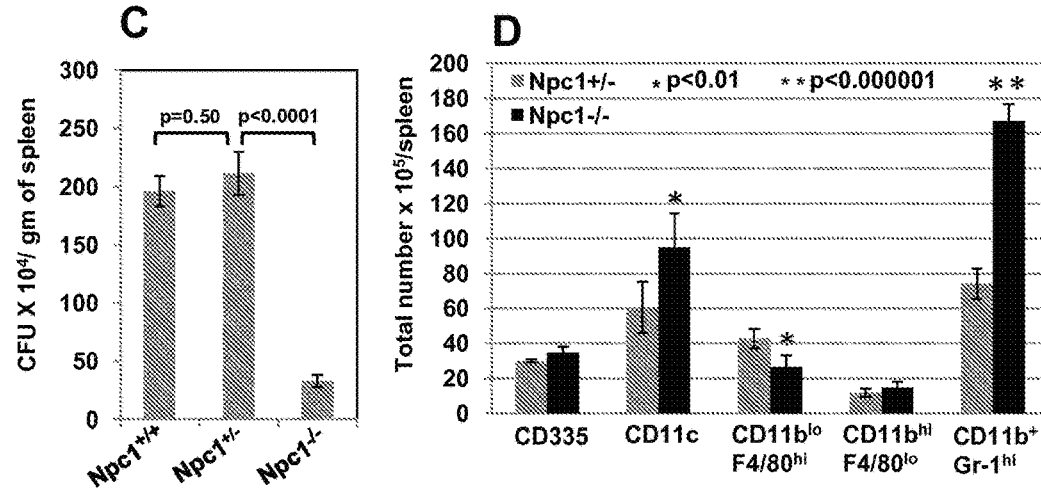

A

*Npc1+/-* (A1, A2)

*Npc1-/-* (A3, A4)

B

Blood cell parameters in *Npc1-/-* mice

|  | Normal Range | *Npc1+/-* | *Npc1-/-* |
|---|---|---|---|
| Leukocytes |  |  |  |
| WBC (K/µl) | 1.8-10.7 | 8.3±0.80 | 8.43±1.39 |
| NE (K/µl) | 0.1-2.4 | 1.18±0.16 | 1.53±0.54 |
| LY (K/µl) | 0.9-9.3 | 6.82±0.67 | 6.515±0.93 |
| MO (K/µl) | 0.0-0.4 | 0.29±0.03 | 0.36±0.08 |
| EO (K/µl) | 0.0-0.2 | 0.01 | 0.025 |
| BA (K/µl) | 0.0-0.2 | 0 | 0.005 |
| Erythrocytes |  |  |  |
| RBC (M/µl) | 6.36-9.42 | 9.69±0.05 | 10.005±0.04 |
| Hb (g/dl) | 11.0-15.1 | 12.85±0.05 | 11.9±0.30 |
| HCT (%) | 35.1-45.4 | 61.35±0.15 | 55.3±0.3 |
| MCV (fl) | 45.4-60.3 | 63.3±0.20 | 55.25±0.05 |
| MCH (pg) | 14.1-19.3 | 13.25±0.15 | 11.85±0.25 |
| MCHC (g/dl) | 30.2-34.2 | 20.95±0.15 | 21.5±0.4 |
| RDW(%) | 12.4-27.0 | 15.45±0.05 | 17.25±0.75 |
| Thrombocytes |  |  |  |
| PLT (K/µl) | 592-2972 | 855±6 | 1023.5±55.5 |
| MPV (fl) | 5.0-20.0 | 4.6 | 4.85±0.05 |

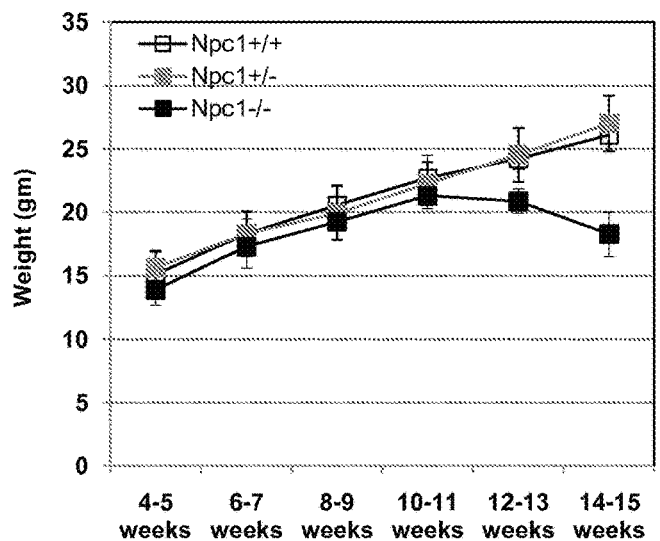
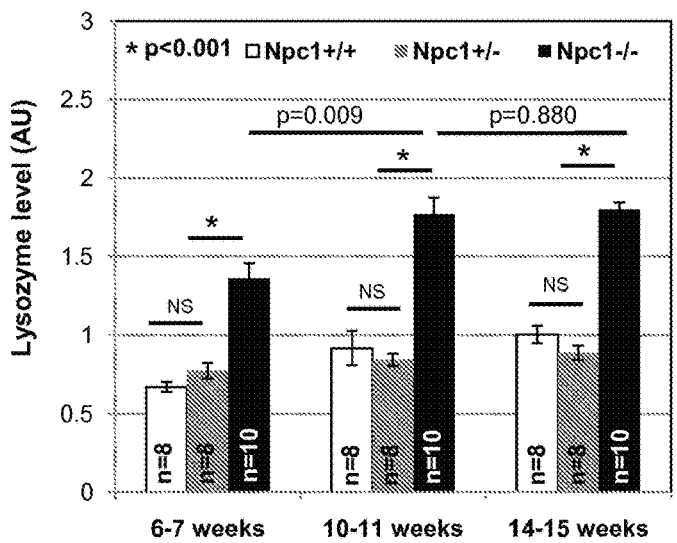
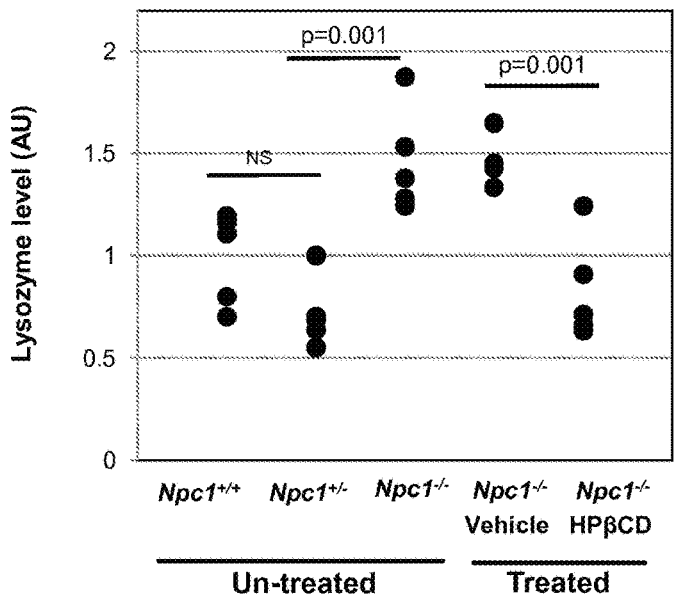
FIG. 34

DETECTION OF NIEMANN-PICK DISEASE COMPRISING DETECTION OF LYSOZYME AND CATHEPSINS

CROSS REFERENCE TO RELATED APPLICATIONS

This application is a National Stage filing under 35 U.S.C. § 371 of International Application No. PCT/US2014/056417 filed Sep. 18, 2014, which claims the benefit of U.S. Provisional Application No. 61/879,529, filed Sep. 18, 2013, which applications are incorporated herein by reference in their entirety.

STATEMENT OF FEDERALLY SPONSORED RESEARCH AND DEVELOPMENT

This invention was made with government support under Grant No. P01HL078826 awarded by the National Institutes of Health. The government has certain rights in the invention.

FIELD OF THE INVENTION

The field of the invention relates to neurodegenerative diseases, treatments and methods of detecting and diagnosing neurodegenerative diseases.

BACKGROUND

Early diagnosis of neurological disorders would greatly improve their management and treatment. A major hurdle is that inflammatory products of cerebral disease are not easily detected in blood. Inflammation in multiple organs and heterogeneity in disease present additional challenges in distinguishing the extent to which a blood based marker reflects disease in brain or other afflicted organs.

Accordingly, there remains a need in the art for diagnostic methods to detect neurodegenerative diseases. There also remains a need for improved methods of treating neurodegenerative diseases and screening methods to determine drug efficacy.

SUMMARY

It is to be understood that both the foregoing general description of the embodiments and the following detailed description are exemplary, and thus do not restrict the scope of the embodiments.

In one aspect, the invention provides a method for detecting an increased probability or risk of neurodegeneration in a subject comprising assaying a sample from the subject for lysozyme and/or cathepsin S and detecting the lysozyme and/or cathepsin S from the sample, wherein an increased lysozyme and/or cathepsin S compared to levels in a control subject indicate an increased probability or risk of neurodegeneration.

In another aspect, the invention provides a method for detecting an increased probability or risk of neurodegeneration in a subject comprising assaying a sample from the subject for lysozyme and cathepsin S and detecting the lysozyme and/or cathepsin S from the sample, wherein an increased ratio of lysozyme:cathepsin S in the subject compared to the ratio of lysozyme:cathepsin S in the control subject indicates an increased probability or risk of neurodegeneration.

In another aspect, the invention provides a method for detecting an increased probability or risk of neurodegeneration in a subject comprising assaying a sample from the subject for lysozyme and cathepsin S and detecting the lysozyme and/or cathepsin S from the sample, wherein an increased ratio of cathepsin S:lysozyme in the subject compared to the ratio of cathepsin S:lysozyme in the control subject indicates an increased probability or risk of neurodegeneration.

In another aspect, the invention provides a method of screening for drug effectiveness in a subject to treat or prevent neurodegeneration comprising:
  i) assaying a sample from the subject for lysozyme and/or cathepsin S and detecting the lysozyme and/or cathepsin S from the sample, wherein an increased lysozyme and/or cathepsin S compared to levels in a control subject indicate an increased probability or risk of neurodegeneration;
  ii) administering to the subject an amount of the drug after the assay of step i); and
  iii) assaying a sample from the subject for lysozyme and/or cathepsin S after the administering of step ii) and detecting the lysozyme and/or cathepsin S from the sample, wherein a reduction in lysozyme and/or cathepsin S in the sample from the subject compared to the lysozyme and/or cathepsin S in the sample from the subject in step i) indicates that the drug may be effective in reducing neurodegeneration.

In another aspect, the invention provides a method of screening for drug effectiveness in a subject to treat or prevent neurodegeneration comprising:
  i) assaying a sample from the subject for lysozyme and cathepsin S and detecting the lysozyme and/or cathepsin S from the sample, wherein an increased ratio of lysozyme:cathepsin S in the subject compared to the ratio of lysozyme:cathepsin S in a control subject indicates an increased probability or risk of neurodegeneration;
  ii) administering to the subject an amount of the drug after the assay of step i); and
  iii) assaying a sample from the subject for lysozyme and cathepsin S after the administering of step ii) and detecting the lysozyme and/or cathepsin S from the sample, wherein a reduction in the ratio of lysozyme:cathepsin S in the subject compared to the ratio of lysozyme:cathepsin S in the sample from the subject in step i) indicates that the drug may be effective in reducing neurodegeneration.

In another aspect, the invention provides a method of screening for drug effectiveness in a subject to treat or prevent neurodegeneration comprising:
  i) assaying a sample from the subject for lysozyme and cathepsin S and detecting the lysozyme and/or cathepsin S from the sample, wherein an increased ratio of cathepsin S:lysozyme in the subject compared to the ratio of cathepsin S:lysozyme in a control subject indicates an increased probability or risk of neurodegeneration;
  ii) administering to the subject an amount of the drug after the assay of step i); and
  iii) assaying a sample from the subject for lysozyme and cathepsin S after the administering of step ii) and detecting the lysozyme and/or cathepsin S from the sample, wherein a reduction in the ratio of cathepsin S:lysozyme in the subject compared to the ratio of cathepsin S:lysozyme in the sample from the subject in step i) indicates that the drug may be effective in reducing neurodegeneration.

In another aspect, the invention provides for a use of lysozyme and cathepsin S as a composite biomarker for detecting an increased probability or risk of neurodegeneration in a subject.

In another aspect, the invention provides for a use of lysozyme and cathepsin S as a composite biomarker in combination with one or more additional biomarkers for detecting an increased probability or risk of neurodegeneration in a subject.

In another aspect, the invention provides for a use of lysozyme as a biomarker for detecting an increased probability or risk of neurodegeneration in a subject.

In another aspect, the invention provides for a use of lysozyme as a biomarker in combination with one or more additional biomarkers for detecting an increased probability or risk of neurodegeneration in a subject.

In another aspect, the invention provides for a use of cathepsin S as a biomarker for detecting an increased probability or risk of neurodegeneration in a subject.

In another aspect, the invention provides for a use of cathepsin S as a biomarker in combination with one or more additional biomarkers for detecting an increased probability or risk of neurodegeneration in a subject.

In another aspect, the invention provides a kit for carrying out any one of the methods of the invention, the kit comprising one or more reagents for detection of lysozyme and/or cathepsin S from a sample.

In another aspect, the invention provides a method for distinguishing a probability or risk of neurodegeneration and inflammation in liver a subject comprising assaying a sample from the subject for lysozyme and cathepsin S and detecting the lysozyme and cathepsin S from the sample,
1) wherein an increased lysozyme and increased cathepsin S compared to levels in a control indicate a relative increased probability or risk of neurodegeneration and a relative increased probability or risk of inflammation in liver;
2) wherein an increased lysozyme and a normal or decreased cathepsin S compared to levels in a control indicate a relative increased probability or risk of neurodegeneration and a relative low probability or risk of inflammation in liver;
3) wherein a normal or decreased lysozyme and a normal or decreased cathepsin S compared to levels in a control indicate a relative low probability or risk of neurodegeneration and a relative low probability or risk of inflammation in liver; and
4) wherein a normal or decreased lysozyme and an increased cathepsin S compared to levels in a control indicate a relative low probability or risk of neurodegeneration and a relative increased probability or risk of inflammation in liver.

In another aspect, the invention provides a method for screening a drug to distinguish the effectiveness of reducing the probability or risk of neurodegeneration and the effectiveness of reducing the probability or risk of inflammation in liver, comprising
i) assaying a sample from a subject for lysozyme and cathepsin S and detecting the lysozyme and cathepsin S from the sample,
1) wherein an increased lysozyme and increased cathepsin S compared to levels in a control indicate a relative increased probability or risk of neurodegeneration and a relative increased probability or risk of inflammation in liver;
2) wherein an increased lysozyme and a normal or decreased cathepsin S compared to levels in a control indicate a relative increased probability or risk of neurodegeneration and a relative low probability or risk of inflammation in liver;
3) wherein a normal or decreased lysozyme and a normal or decreased cathepsin S compared to levels in a control indicate a relative low probability or risk of neurodegeneration and a relative low probability or risk of inflammation in liver;
4) wherein a normal or decreased lysozyme and an increased cathepsin S compared to levels in a control indicate a relative low probability or risk of neurodegeneration and a relative increased probability or risk of inflammation in liver;
ii) administering to the subject an amount of the drug after the assay of step i); and
iii) assaying a sample from the subject for lysozyme and cathepsin S after the administering of step ii) and detecting the lysozyme and cathepsin S from the sample,
1) wherein if the subject exhibits a profile corresponding to i)1) prior to administering and following administering exhibits a profile corresponding to i)4), then the drug is relatively more effective at reducing the probability or risk of neurodegeneration than reducing the probability or risk of inflammation in liver;
2) wherein if the subject exhibits a profile corresponding to i)1) prior to administering and following administering exhibits a profile corresponding to i)2), then the drug is relatively more effective at reducing the probability or risk of inflammation in liver compared to the probability or risk of neurodegeneration;
3) wherein if the subject exhibits a profile corresponding to i)2) prior to administering and following administering exhibits a profile corresponding to i)3), then the drug is effective at reducing the probability or risk of neurodegeneration;
4) wherein if the subject exhibits a profile corresponding to i)4) prior to administering and following administering exhibits a profile corresponding to i)3), then the drug is effective at reducing the probability or risk of inflammation in liver.

In some embodiments, the sample is a plasma sample.

In some embodiments, the neurodegeneration is caused by a disease selected from Alpha-mannosidosis, Cystinosis, Danon disease, Fabry disease, Farber disease, Fucosidosis, Galactosialidosis, Gaucher Disease (Type1, TypeII, TypeIII), GM1 gangliosidosis (infantile, juvenile and adult), I-Cell disease (Mucolipidosis II), Infantile Free Sialic Acid Storage Disease, Juvenile Hexosaminidase A Deficiency, Krabbe disease (Infantile and late onset), Lysosomal acid lipase deficiency (early and late), Metachromatic Leukodystrophy, Pseudo-Hurler polydystrophy (Mucolipidosis IIIA), MPSI (Hurler Syndrome), MPS II (Hunter syndrome), Sanfilippo syndrome Type A (MPS III A), Sanfilippo syndrome Type B (MPS III B), Sanfilippo syndrome Type C (MPS III C), Sanfilippo syndrome Type D (MPS III D), Morquio Type A (MPS IVA), Morquio Type B (MPS IVB), MPS IX (Hyaluronidase Deficiency), MPS VI (Maroteaux-Lamy), MPS VII (Sly Syndrome), Mucolipidosis I (Sialidosis), Mucolipidosis IIIC, Mucolipidosis type IV, Multiple sulfatase deficiency, Niemann-Pick Disease, Type A, Niemann-Pick Disease, Type B, Niemann-Pick Disease, Type C, Neuronal Ceroid Lipofuscinoses, Pompe disease, Pycnodysostosis, Sandhoff disease (infantile, juvenile and adult), Schindler disease, Salla disease (Sialic Acid Storage Disease), Tay-Sachs disease, Wolman disease, chronic traumatic encephalopathy, Alzheimer's disease (AD), Parkinson disease (PD), Huntington disease (HD), Frontotemporal dementia (FTD-3 subtype), Amyotrophic lateral sclerosis (ALS), Charcot-Marie Tooth disease type 2B, Neuronal ceroid lipofuscinoses/Batten disease (NCL), Creutzfeldt- Jakob disease, Autosomal dominant Spastin hereditary spastic paraplegia (ADHSP), Chediak-Higashi syndrome (CHS), and Inclusion body myositis (IBM).

BRIEF DESCRIPTION OF THE DRAWINGS

The skilled artisan will understand that the drawings, described below, are for illustration purposes only. The drawings are not intended to limit the scope of the present teachings in any way.

FIG. 7. Increased neutrophils in spleen of Npc1$^{-/-}$ mice. (A) Flow cytometric analysis of innate immune cells in spleen of Npc1$^{+/-}$ and Npc1$^{-/-}$ mice. Splenocytes from un-infected Npc1$^{+/-}$ and Npc1$^{-/-}$ female littermates (age 6-8 weeks) mice were isolated and stained with anti-CD335 for NK cells, anti-CD11c for dendritic cells (DC), anti-F4/80 and CD11b for monocytes and macrophages (Mo/MO), anti-Gr-1 and CD11b for neutrophils. The data represent the mean from two independent experiments with a total of 6 mice (3 each experiment). Error bars show the mean±SD. Gating parameters are indicated in FIG. 11. (B) Flow cytometric analysis of innate immune cells in the spleen of *S. typhimurium* infected Npc1$^{+/-}$ and Npc1$^{-/-}$ mice. Mice at 6-8 weeks were infected with *S. typhimurium* intraperitoneally (see Materials and Methods) and splenocytes were prepared at 48 hpi. Innate immune cells were analyzed as described in A. The data represent the mean from three independent experiments with a total of 6 mice (2 each experiment). Error bars indicate the mean±SD. Statistical significance was determined using Student's t test. Gating parameters are indicated in FIG. 11.

Npc1$^{-/-}$ mice treated with saline (D) Npc1$^{-/-}$ mice treated with HPβCD. CTSS staining (brown) were seen in the foamy macrophages (blue arrows) of un- and saline-treated Npc1$^{-/-}$ mice. HPβCD injection eliminated the foamy macrophages and CTSS staining. To visualize neutrophils, sections were stained with anti-Ly-6G antibodies. In (E) liver sections are shown from Npc1$^{+/-}$ mice at 54 days (E1) and 80 days (E2). 1-2 neutrophils (cell stained in brown) are infrequently seen in these sections. (F) Detection of giant foci of neutrophils (cluster of brown cells, blue arrows) in the liver of Npc1$^{-/-}$ mouse at age 54 days (F1). Increased sizes of neutrophil clusters were seen as mice aged to 80 days (F2). (G) Large foci of neutrophils were also seen in liver sections of Npc1$^{-/-}$ mice treated with saline at 50 (G1) and 80 days (G2). (H) Neutrophils were barely detected in liver sections from Npc1$^{-/-}$ mice treated with HPβCD at either 50 or 80 days (H1-H2). Original magnifications ×40. Representative images are shown. I-M. (I) mRNA levels of Lyz1 (Lysozyme 1) in liver. Mice, Npc1$^{+/-}$ (+/−) and Npc1$^{-/-}$ (−/−) treated with saline or HPβCD were sacrificed between 70 to 95 days. Total RNA was extracted from liver and the expression of Lyz1 was quantified by qPCR (as described in Materials and Methods). Gapdh was used as an internal control. Fold change shown is relative to average levels of Lyz1 transcripts detected in Npc1$^{+/-}$ mice. The data represent mean triplicate values±SD. Data were subjected to the Student's t test for statistical significance. J-M. Immunofluorescence analyses of lysozyme in liver: effects of HPβCD. Liver sections of Npc1$^{+/-}$ and Npc1$^{-/-}$ mice were stained with anti-mouse lysozyme antibodies. Immunostaining shows the expression of lysozyme in the liver section of (J) untreated Npc1$^{+/-}$ mice (K) untreated Npc1$^{-/-}$ mice (L) Npc1$^{-/-}$ mice treated with saline (M) Npc1$^{-/-}$ mice treated with HPβCD. Enhanced lysozyme staining (green) was seen in the foamy macrophages (white arrows) of untreated and saline-treated Npc1$^{-/-}$ mice.

Figure 16:
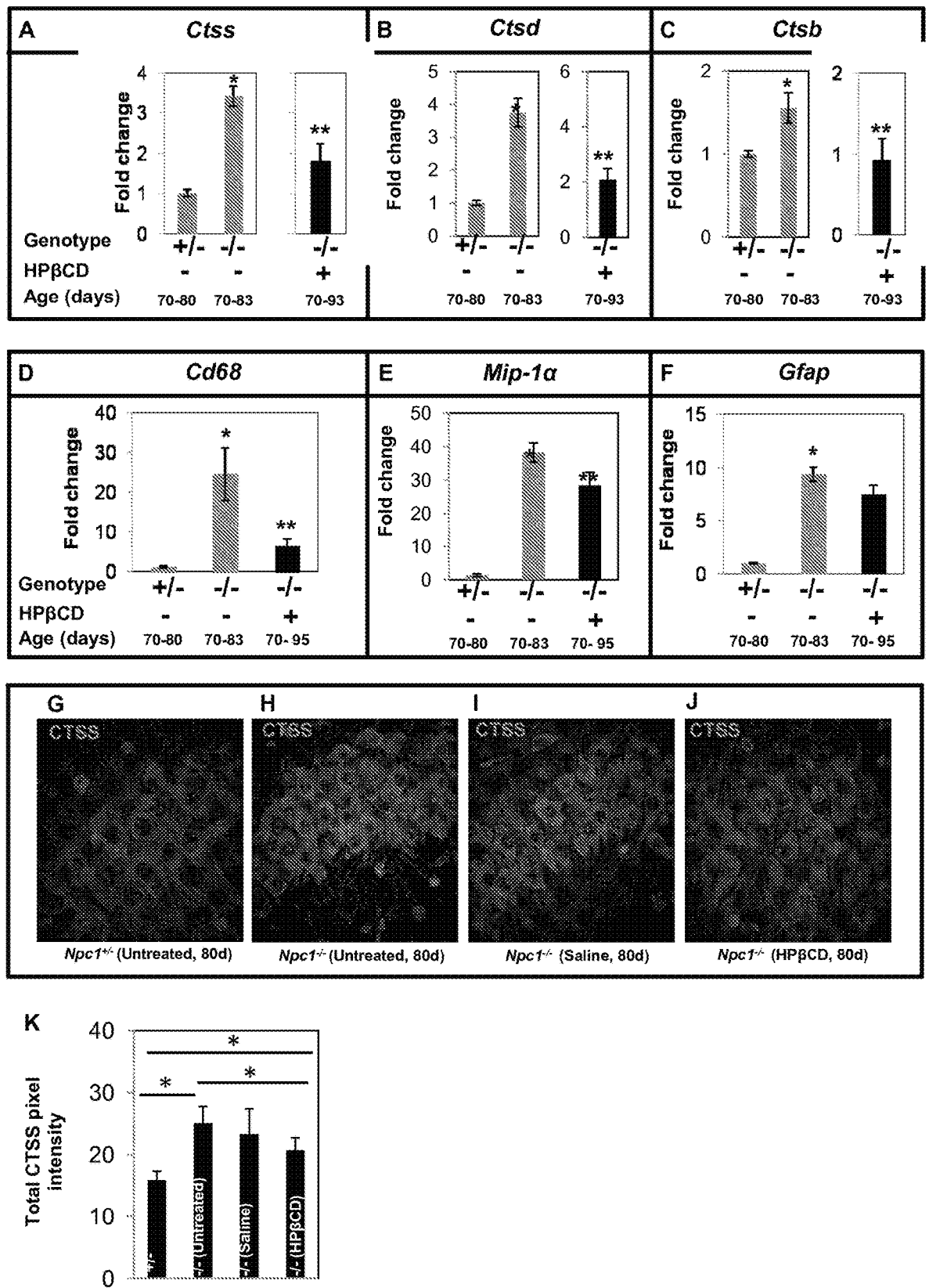

FIG. 16. Effect of cyclodextrin treatment on the expression of cathepsins and inflammatory markers in Npc1$^{nih}$ mouse brain. Total RNA from the brain was prepared and qPCR analysis was carried out for (A) Ctss (B) Ctsd (C) Ctsb (D) Cd68 (E) Mi-1α and (F) Gfap. For Ctss, Ctsd and Ctsb (A-C), there were 4 mice per group. For Cd68, Mip-1α and Gfap (E-F) there were 6 per group. Fold change in Npc1$^{-/-}$ is expressed relative to transcript levels in Npc1$^{+/-}$ mice. The data represent mean triplicate values±SD. Gapdh was used as an internal control. The data shown for untreated Npc1$^{-/-}$ mice in 'A-C' are identical to those shown in FIG. 12C to enable comparisons across the study. *Npc1$^{+/-}$ vs untreated Npc1$^{-/-}$, p<0.005; **untreated Npc1$^{-/-}$ vs treated Npc1$^{-/-}$, p<0.05. G-J. Immuno fluorescence micrographs showing the expression of CTSS in the hippocampal neurons of (G) untreated Npc1$^{-/-}$ mice (H) untreated Npc1$^{-/-}$ mice (I) Npc1$^{-/-}$ mice treated with saline (J) Npc1$^{-/-}$ mice treated with HPβCD. Enhanced CTSS staining were seen in untreated and saline treated Npc1$^{-/-}$ mice. Original magnifications ×40. Representative images are shown. (K) Quantification of CTSS fluorescence using ImageJ software. Eight sections (2 mice/group, 4 sections/mouse) were analyzed. The data represent the mean±SD. *p<0.05.

Figure 17:
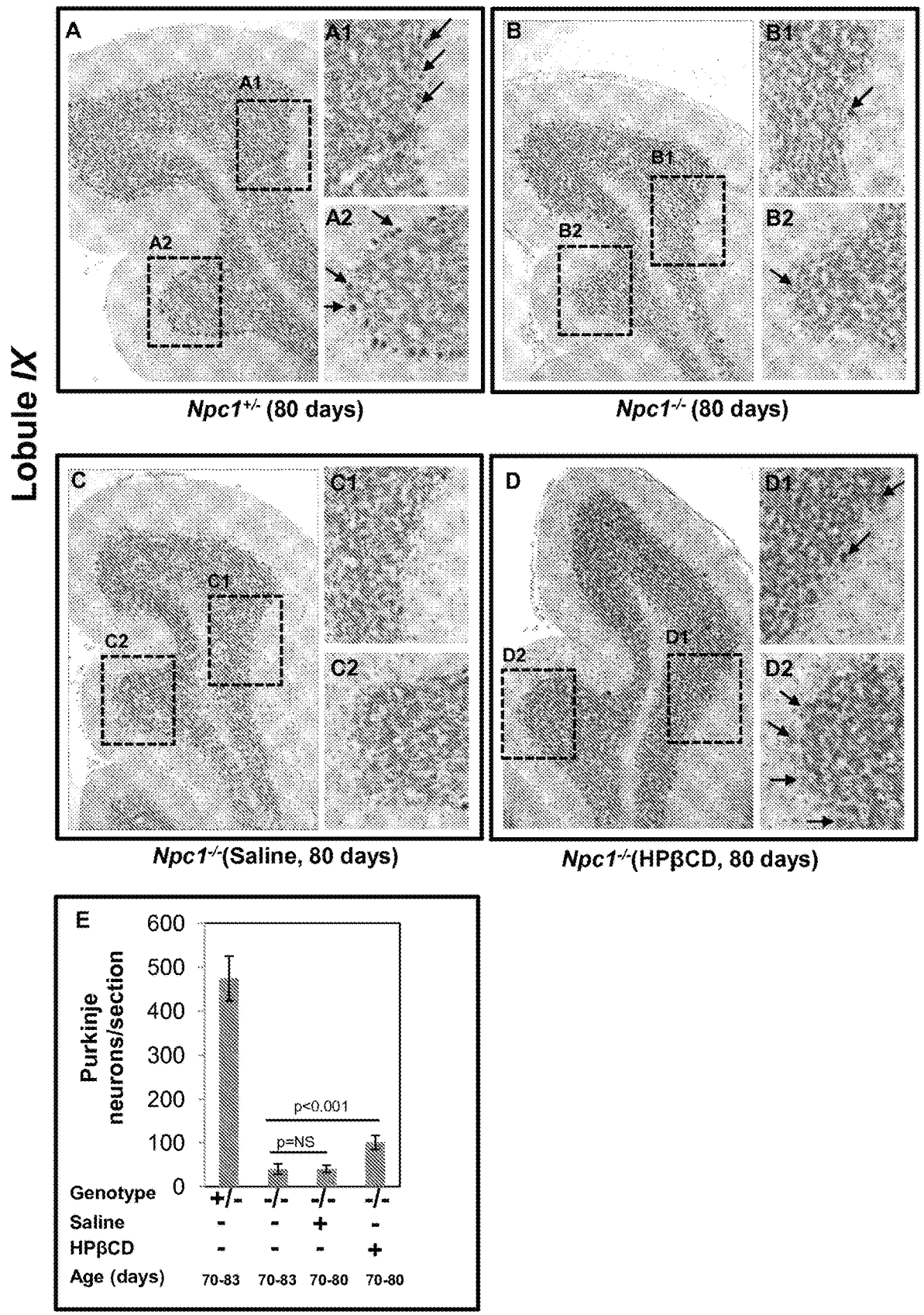

FIG. 17. Effects of cyclodextrin on the Npc1$^{nih}$ mouse brain as determined by immunohistochemistry. Formalin-fixed paraffin embedded brains were sectioned (sagittal, 4-5 μm) and stained using anti-mouse calbindin antibodies to visualize Purkinje neurons in the entire cerebellum. Micrographs shown are representative images of IX lobule of the cerebellum. (A) Purkinje neurons (stained in brown) indicated by black arrows are evident in Npc1$^{+/-}$ mice (age 80 days). A1 and A2 are the magnified areas boxed in A. (B) Loss of Purkinje cells in the cerebellum of Npc1$^{-/-}$ mouse (age 80 days). Calbindin immunoreactivity was barely detected across the different lobules of cerebellum. B1 and B2 are magnified areas boxed in B. (C) Cerebellar section of Npc1$^{-/-}$ mouse (age 80 days) injected with saline were devoid of Purkinje neurons. C1 and C2 are magnified areas boxed in C. (D) Chronic HPβCD treatment (that partially rescued inflammation) also partially recovered Purkinje neurons in Npc1−/− mice. Few lightly brown stained Purkinje neurons (indicated by arrows) are seen. D1 and D2 are magnified areas boxed in D. Original magnifications ×40. (E) Semi-quantitative analysis of Purkinje neurons in Npc1$^{nih}$ mouse brain. Number of Purkinje neurons in the calbindin labeled cerebellar sections from 4 mice (age 80 days) in each group were counted. HPβCD treatment resulted into a small but significant increase in the number of Purkinje neurons. The data represent the mean±SD.

Figure 18:
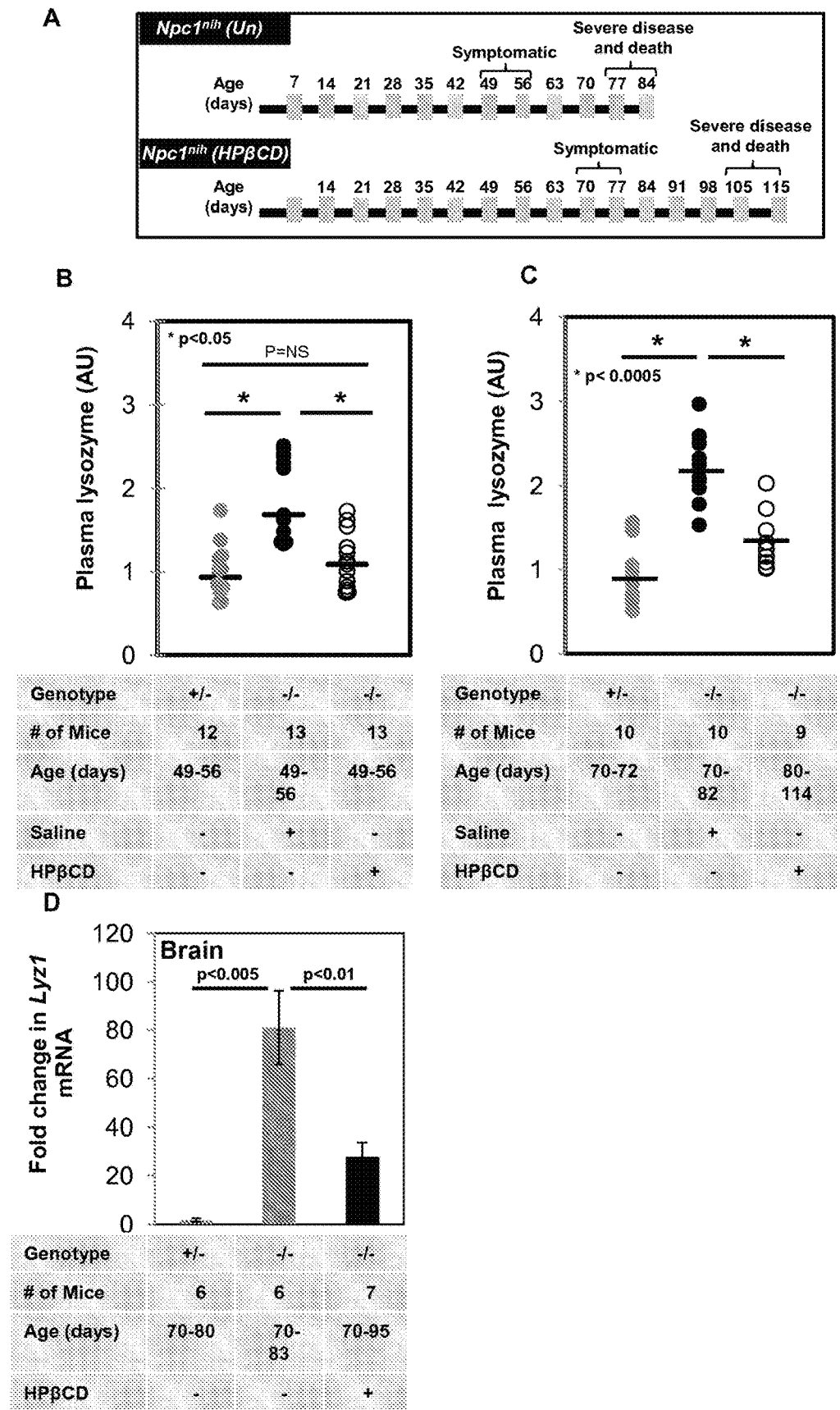

FIG. 18. Cyclodextrin partially reduces lysozyme levels in plasma and brain of Npc1$^{nih}$ mice. (A) Diagrammatic representation of the onset of phenotypic symptoms and life span of Npc1$^{nih}$ mice (upper panel) and their improvement upon treatment with HPβCD (lower panel). Plasma lysozyme activity was determined for Npc1$^{-/-}$ mice (−/−) treated with saline or HPβCD compared to untreated Npc1$^{+/-}$ mice (+/−) at (B) 49-56 days and (C) 80-114 days. Fold change shown is relative to average levels of lysozyme activity detected in Npc1$^{+/-}$ mice. Horizontal lines indicate median values. (D) mRNA levels of Lyz1 (Lysozyme 1) in brain. Mice, Npc1$^{+/-}$ (+/−) and Npc1$^{-/-}$ (−/−) treated with saline or HPβCD were sacrificed between 70 to 95 days. Total RNA was extracted from liver and brain and the expression of Lyz1 was quantified by qPCR (as described in Materials and Methods). Gapdh was used as an internal control. Fold change shown is relative to average levels of Lyz1 transcripts detected in Npc1$^{+/-}$ mice. Data represent the mean of three experiments±SEM. Data were subjected to the Student's t test for statistical significance.

Figure 19:
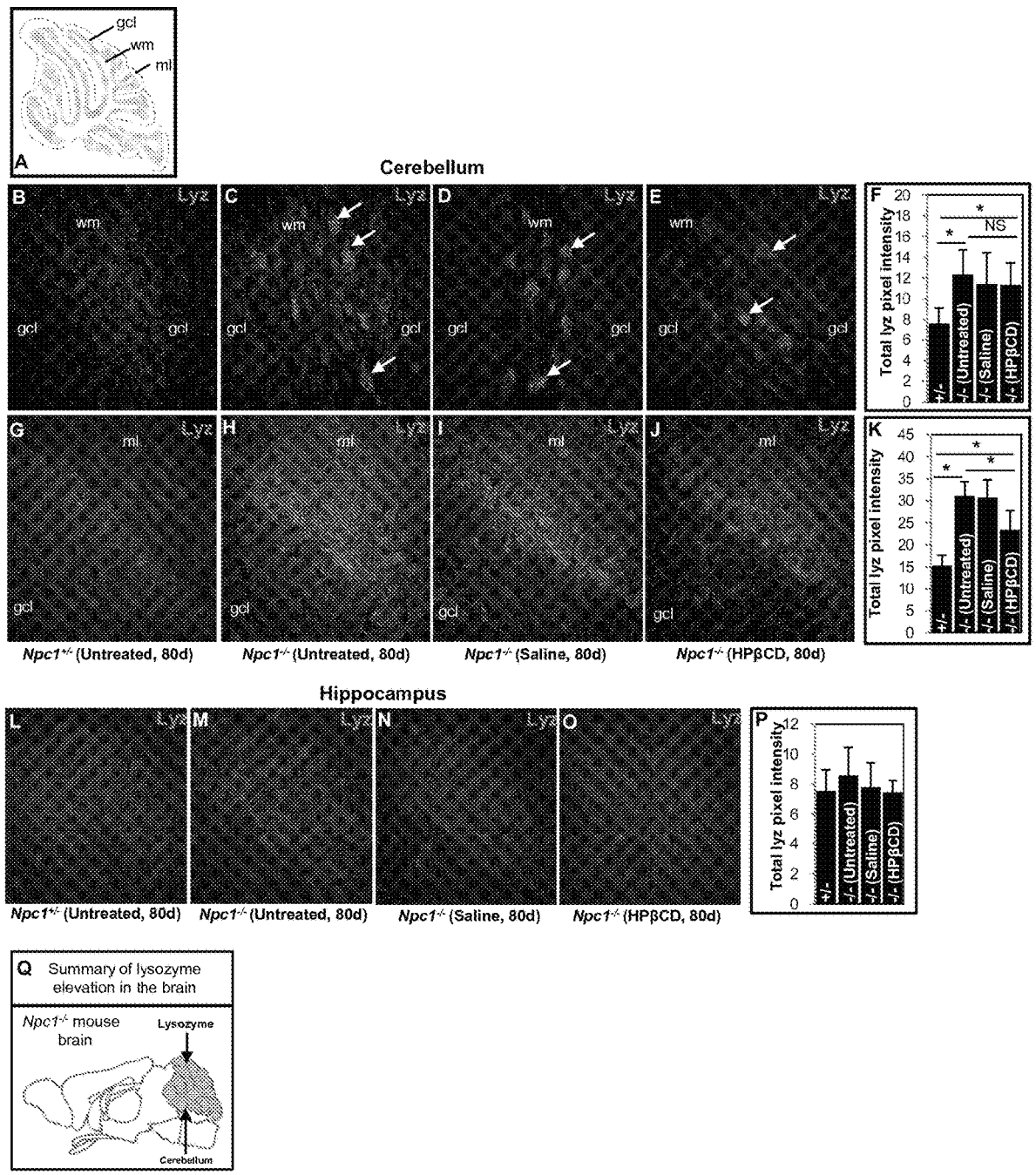

FIG. 19. Immunohistochemical analyses of lysozyme in brain of Npc1$^{nih}$ mice. (A) Schematic illustration of the structure of mouse cerebellum. gcl, granule cell layer; wm, white mater; ml, molecular layer. Brain sections of Npc1$^{+/-}$ and Npc1$^{-/-}$ mice were stained with anti-mouse lysozyme antibodies B-E. Immunohistochemical micrographs corresponding to the granule cell layer and white mater of the cerebellum of (B) untreated Npc1$^{+/-}$ mice (C) untreated Npc1$^{-/-}$ mice (D) Npc1$^{-/-}$ mice treated with saline (E) Npc1$^{-/-}$ mice treated with HPβCD. Numerous lysozyme positive cells (green, indicated by white arrows) were primarily seen in the white mater of the cerebellum of Npc1$^{-/-}$ mice. (F) Bar diagram shows the total lysozyme intensity in the cerebellum corresponding to region shown in B-E. G-J. Region corresponding to granule cell layer and molecular layer of the cerebellum of (G) untreated Npc1$^{+/-}$ mice (H) untreated Npc1$^{-/-}$ mice (I) Npc1$^{-/-}$ mice treated with saline (J) Npc1$^{-/-}$ mice treated with HPβCD. Enhanced lysozyme staining in the molecular layer of the cerebellum of untreated and saline treated Npc1$^{-/-}$ mice were seen. (K) Bar diagram shows the total lysozyme intensity in the cerebellum corresponding to region shown in region G-J. L-O. Immunohistochemical micrographs show the staining of lysozyme in hippocampus of (L) untreated Npc1$^{+/-}$ mice (M) untreated Npc1$^{-/-}$ mice (N) Npc1$^{-/-}$ mice treated with saline (O) Npc1$^{-/-}$ mice treated with HPβCD. (P) Quantification of lysozyme fluorescence in the hippocampus corresponding to region shown in L-O. Nuclei (blue) are stained with DAPI. Treatment and age of the mouse are shown.

Original magnifications ×40. Representative images are shown. ImageJ was used for the quantification of lysozyme fluorescence. In cerebellum, twenty different fields (2 mice/group, ten fields from each mouse) were analyzed. In hippocampus eight sections (2 mice/group, 4 sections/mouse) were analyzed. The data represent the mean±SD. *p<0.05. (Q) Schematic summarizing elevation of lysozyme in cerebellum of the $Npc1^{-/-}$ mouse brain.

FIG. 20. Evidence of lysozyme elevation in patients and development of a composite scale to distinguish between four distinct states of cerebral and liver disease. (A) Expression analysis of Lyz (lysozyme gene) in liver and cerebellum of four human NPC patients. Expression levels of Lyz were determined by qPCR. Fold change is relative to average value of control subjects. Gapdh was used as an internal control. (B) Correlation between plasma lysozyme activity and cathepsin S level in NPC mice treated with (i) saline (ii) HPβCD and (iii) a derived quartile score predictive of four distinct states of neurodegeneration and liver disease, suggesting composite plasma diagnostic of neuroinflammation.

Figure 21:
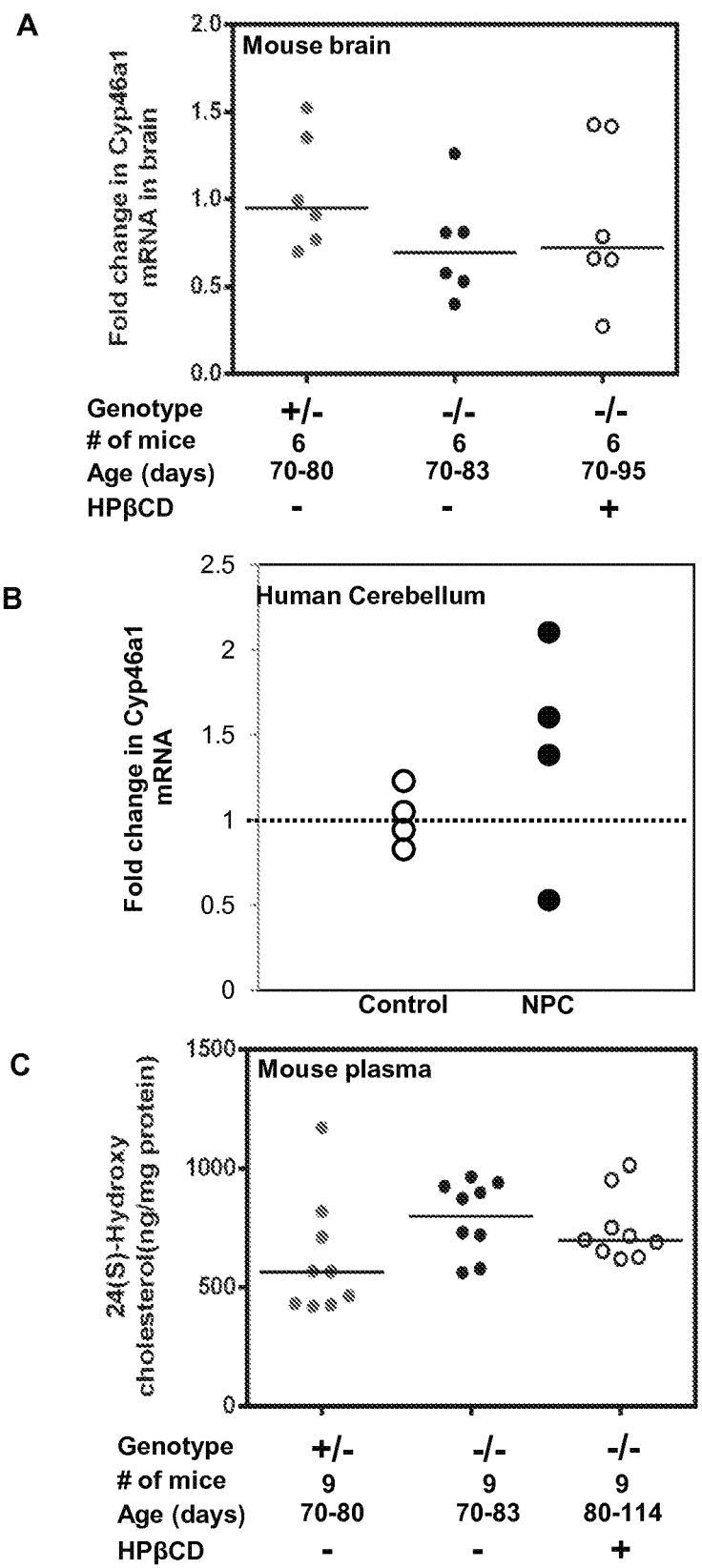

FIG. 21. Expression of 24-hydroxylase gene and plasma 24(S)-hydroxy cholesterol level in NPC. (A) Expression of 24-hydroxylase (Cyp46a1) gene in NPC mouse brain. Cyp46a1 RNA level was determined by qPCR with total RNA extracted from the brain of $Npc1^{+/-}$ (+/-, n=6), $Npc1^{-/-}$ (-/-, n=6) and HPβCD-treated $Npc1^{-/-}$ (-/-, n=6) mice. Fold increase is expressed relative to transcript levels in $Npc1^{+/-}$ mice. (B) Expression of Cyp46a1 gene in the cerebellum of 4 NPC and 4 control subjects. Expression levels were determined by qPCR. Fold change is relative to average value of control subjects. Change above and below 1 (shown by dotted line) represents the extent of up- and down-regulation respectively. For both mouse and human qPCR studies, Gapdh was used as an internal control. Horizontal bars show the median values. (C) 24(S)-hydroxy cholesterol (24-HC) levels in $Npc1^{nih}$ $Npc1^{-/-}$ (-/-) mice treated with saline or HPβCD compared to $Npc1^{+/-}$ (+/-). The plasma concentration of 24-HC was determined by ELISA (see Materials and Methods).

Figure 22:
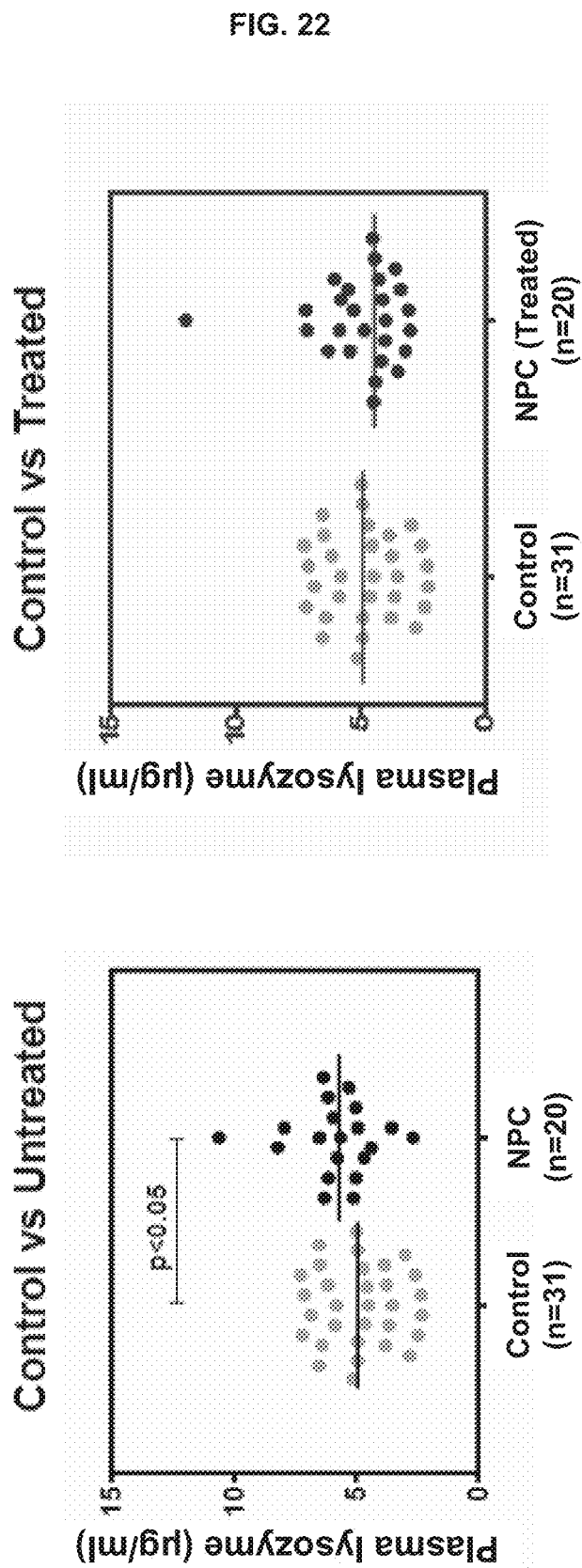

FIG. 22. Lysozyme level in the plasma of untreated NPC (left) and Miglustat-treated NPC (right) patient. Healthy control samples are shown in grey and NPC samples are shown in black sphere.

Figure 23:
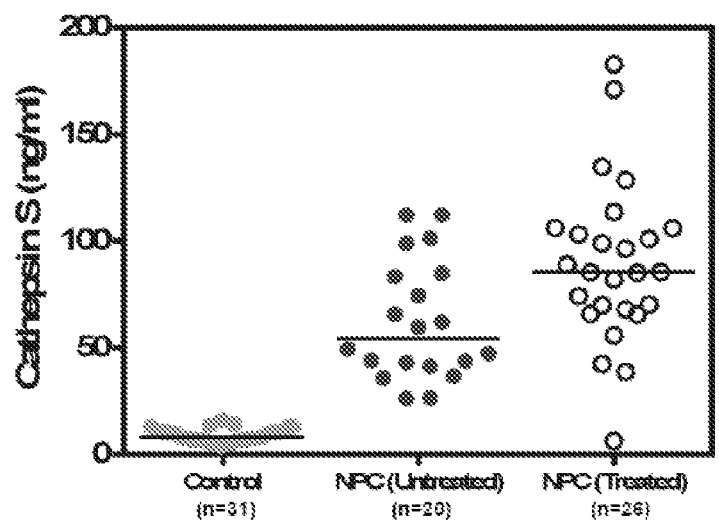
Figure 24:
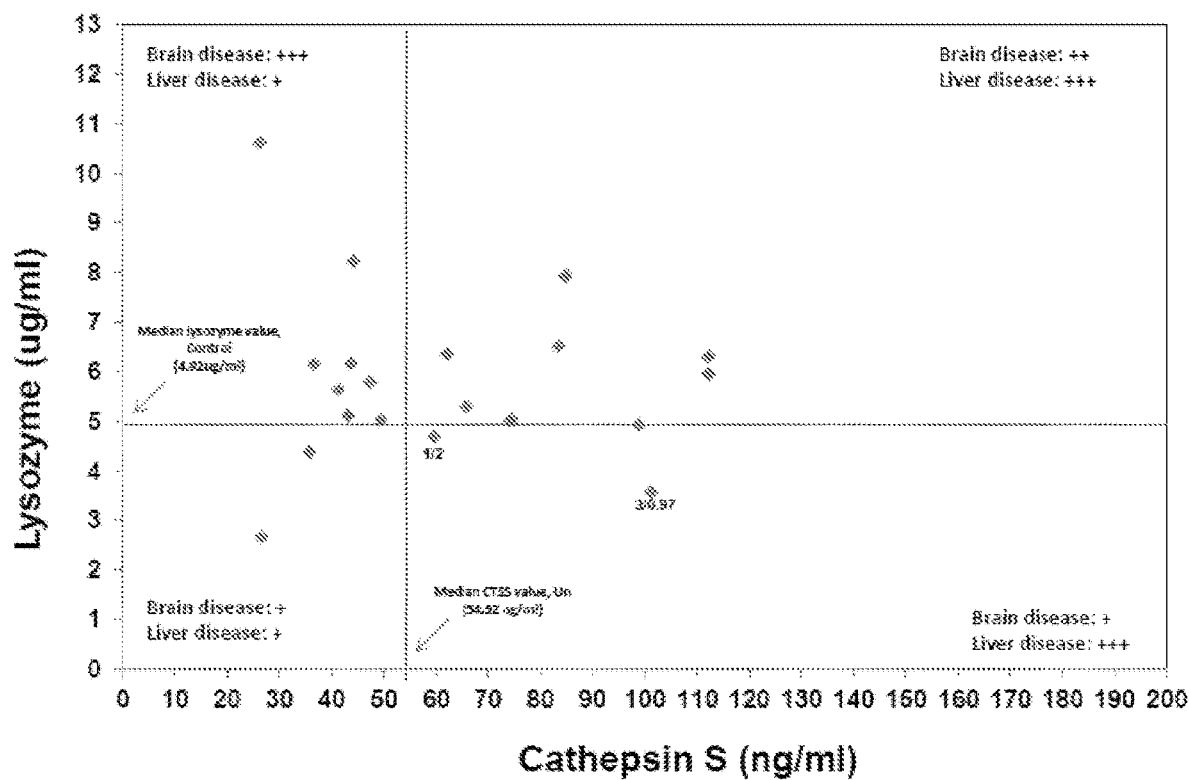

FIG. 23. Cathepsin S level in the plasma of healthy controls (grey) untreated NPC (solid black) and Miglustat-treated NPC (open circles) patients FIG. 24. Correlation between plasma lysozyme and cathepsin S level in NPC patients. Quartile 1 (upper left) represent high lysozyme and low cathepsin S level, an indicative of high brain disease and low systemic disease. Quartile 2 (upper right) represent high lysozyme and high cathepsin S level, an indicative of moderate brain disease and high systemic disease. Quartile 3 (lower right) represent low lysozyme and high cathepsin S level, an indicative of high brain disease and low systemic disease. Quartile 4 (lower left) represent low lysozyme and low cathepsin S level, an indicative of low/no brain disease and low/no systemic disease.

Figure 25:
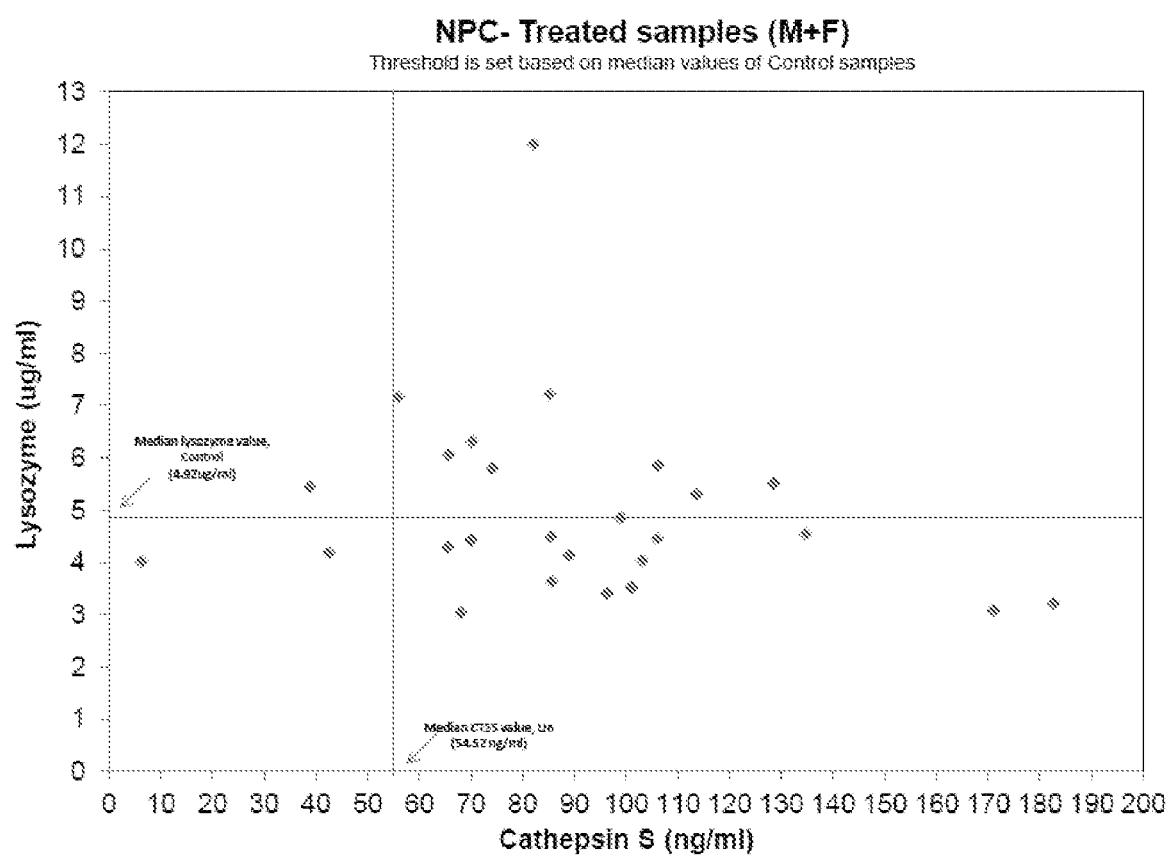

FIG. 25. Correlation between plasma lysozyme and cathepsin S level in Miglustat-treated NPC patients. Quartile 1 (upper left) represent high lysozyme and low cathepsin S level, an indicative of high brain disease and low liver disease. Quartile 2 (upper right) represent high lysozyme and high cathepsin S level, an indicative of moderate brain disease and high liver disease. Quartile 3 (lower right) represent low lysozyme and high cathepsin S level, an indicative of high brain disease and low liver disease. Quartile 4 (lower left) represent low lysozyme and low cathepsin S level, an indicative of low/no brain disease and low/no liver disease.

Figure 26:
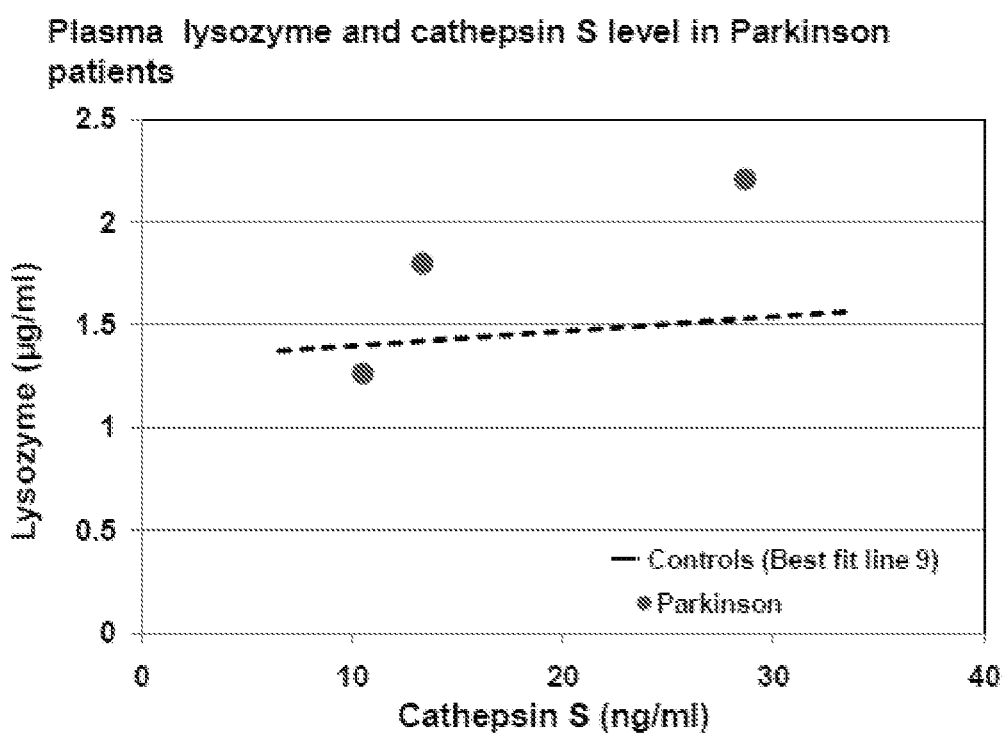

FIG. 26. Correlation between plasma lysozyme and cathepsin S level in Parkinson patients.

Figure 27:
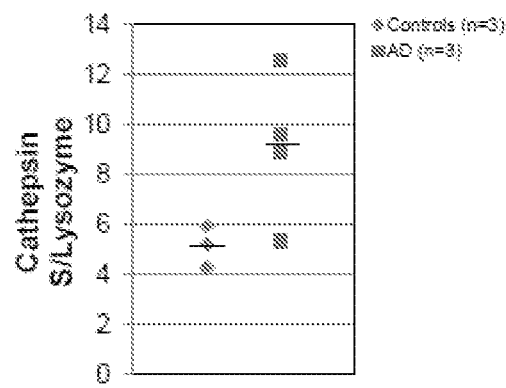

FIG. 27. Elevation in the ratio of plasma cathepsin S and lysozyme level in Alzheimer patients.

FIG. 28. Gene Expression profiling on spleen from $Npc1^{-/-}$ mice. (A). Plot of $\log_2$ normalized signal from spleen of 6 $Npc1^{-/-}$ vs 6 $Npc1^{+/-}$ mice (age 20-71 days). Total RNA from spleen of 12 mice (6 $Npc1^{-/-}$ and 6 age matched controls ($Npc1^{+/-}$) of age ranging 20-71 days (3 age groups, see FIG. 9Bfor details) were isolated and expression of transcripts were assessed using affymetrix microarray chips. The level of 247 transcripts (229 up and 18 down) in the $Npc1^{-/-}$ mice changed by 1.5 fold or higher (p<0.05). Red squares, blue squares and grey diamonds respectively indicate transcripts that are up regulated, down regulated or unchanged. Inset, pie chart displays 1.47% up-regulated 0.11% down regulated transcripts relative to the total number of transcripts expressed (15348) in spleen. (B). Table shows fold change in top 20 up regulated transcripts in spleen of $Npc1^{-/-}$ mice. 5 of 20 genes (shown in bold and underlined) are reported to have roles in innate immunity and/or antimicrobial activity and are enlisted in InnateDB (Lynn et al., 2008).

FIG. 29. Elevation of neutrophils and attenuation of *S. typhimurium* proliferation in spleen of $Npc1^{-/-}$ mice. (A) Flow cytometric analysis of innate immunity cells in spleen of $Npc1^{+/-}$ and $Npc1^{-/-}$ mice. Splenocytes from un-infected $Npc1^{+/-}$ and $Npc1^{-/-}$ female littermates (age 6-8 weeks) mice were isolated and stained with anti-CD335 for NK cell, anti-CD11c for dendritic cells (DC), anti-F4/80 and CD11b for monocytes and macrophages (Mo/MO), anti-Gr-1 and CD11b for neutrophils. Cell numbers were determined using flow cytometry. Data represent the mean from two independent experiments with a total of 6 mice (3 each experiment). Error bars show the mean±SD. (B) Immunohistochemical analysis confirmed the increased accumulation of neutrophils in the spleen of $Npc1^{-/-}$ mouse. Formalin-fixed paraffin embedded spleen sections (3-4 μm) of $Npc1^{-/-}$ and $Npc1^{+/-}$ mice (age 48-52 days) were stained with anti-Gr-1 antibodies to visualize neutrophils (cells stained in brown) which were primarily observed in the marginal zone, and in the red pulp of the spleen. Prominent accumulation of neutrophils was seen in the red pulp of $Npc1^{-/-}$ mouse (B3-4) compared to $Npc1^{+/-}$ mouse (B1-2). B2 and B4 are magnified view of area shown by dotted box in B1 and B3 respectively. M, megacaryocyte; T, trabecula. Original magnifications, ×400 (B1 &B3) and ×1000 (B2&B4). (C) Attenuated proliferation of *S. typhimurium* in the spleen of $Npc1^{-/-}$ mice. $Npc1^{+/+}$, Npc1+/- and $Npc1^{-/-}$, mice (age 6-8 weeks) were infected with *S. typhimurium* ($1 \times 10^4$ CFU) by i.p injection. At 48 hpi, mice were sacrificed and bacterial CFU was determined. The data obtained from 3 independent experiments are shown. N=10 for $Npc1^{+/+}$ and $Npc1^{-/-}$ and N=8 for $Npc1^{+/-}$. Error bar show the mean±SEM. Student's t test was carried out to determine the statistical significance. (D) Flow cytometric analysis of innate immunity cells in spleen of *S. typhimurium* infected $Npc1^{+/-}$ and $Npc1^{-/-}$ mice $Npc1^{+/-}$ and $Npc1^{-/-}$ (age 6-8 weeks) mice were infected with *S. typhimurium* intraperitoneally (see Materials and Methods) and splenocytes were prepared at 48 hpi. Different innate immunity cells were enumerated using flow cytometry using surface markers as described for un-infected mice. Data represent the means from three independent experiments with a total of 6 mice (2 each experiment). Error bars show the mean±SD. Student's t test was carried out to determine the statistical significance.

Figure 30:
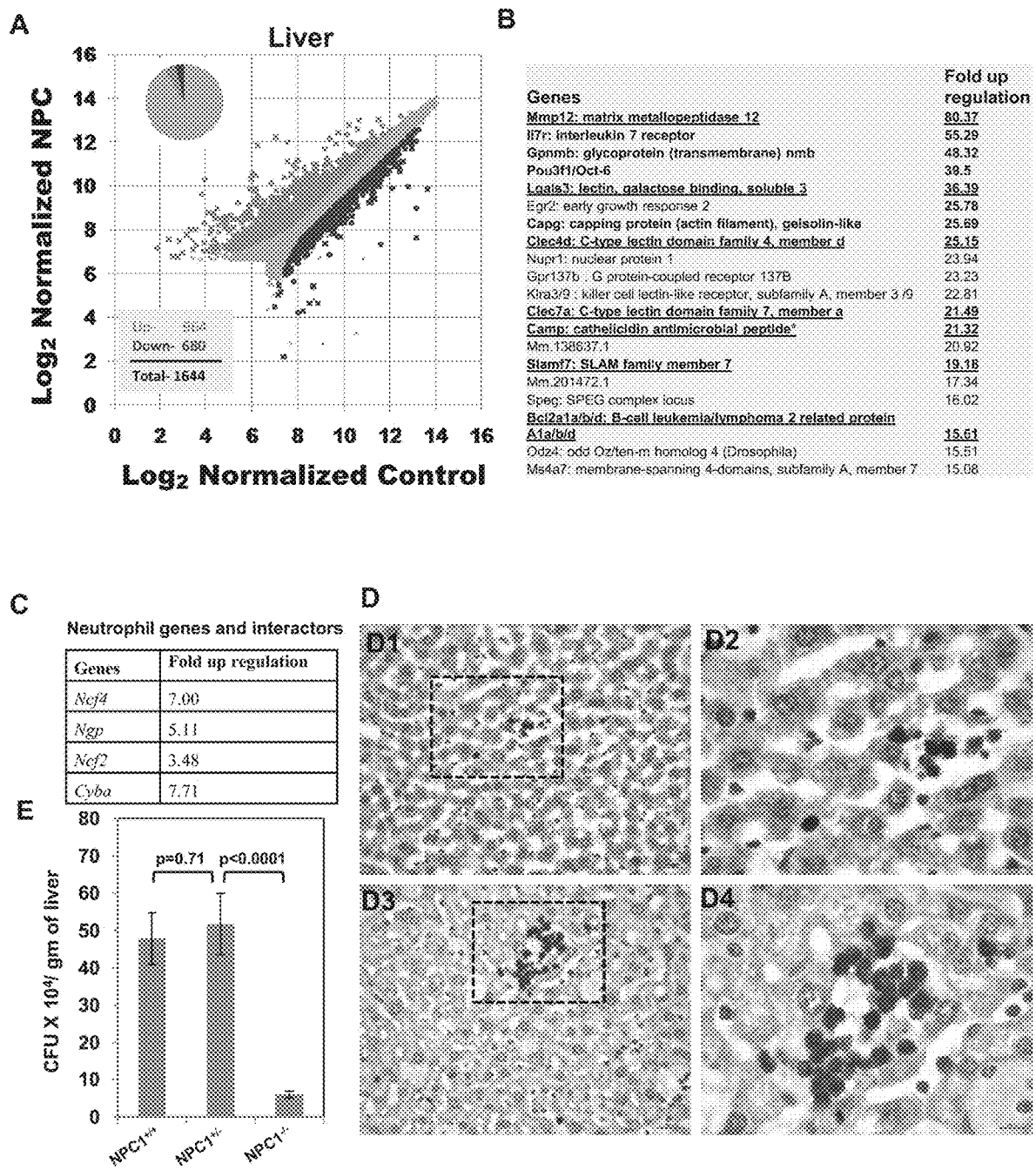

FIG. 30. Elevation of neutrophils and attenuation of *S. typhimurium* in the liver from Npc1$^{-/-}$ mice. (A). Expression analysis showing plot of $\log_2$ normalized signal from liver of 6 Npc1$^{-/-}$ vs 6 Npc1$^{+/-}$ mice (age 20-71 days). Total RNA from spleen of 12 mice (6 Npc1$^{-/-}$ and 6 age matched controls (Npc1$^{+/-}$) of age ranging 20-71 days (3 age groups, see FIG. 9B for details) were isolated and expression of transcripts were assessed using Affimetrix microarray chips. The levels of 1648 transcripts (968 up and 680 down) in the Npc1$^{-/-}$ mice change by 1.5 fold or higher (p<0.05). Red squares, blue squares and grey diamonds respectively indicate transcripts that are up regulated, down regulated or unchanged. Inset, pie chart displays 5.24% up regulated 3.7% down regulated transcripts expressed as a fraction of total transcripts in liver (18377). (B). Table shows the top 20 up regulated transcripts and their fold up regulation in liver of Npc1$^{-/-}$ mice. Total 10 out of 20 genes (shown in bold) are reported to have roles in innate immunity and/or antimicrobial activity. Seven (bold and underlined) are enlisted in InnateDB (Lynn et al., 2008). (C). Table shows 4 neutrophil-specific transcripts up regulated in liver: the proteins encoded are known to function together in a complex. (D) Detection of giant foci of neutrophils (cells stained in brown) in the liver of Npc1$^{-/-}$ mouse (D3-4), while quasi non-existent in the liver of Npc1$^{+/-}$ mouse (D1-2), age 48-52 days. Immunohistochemical staining on formalin-fixed paraffin embedded liver sections (3-4 μm) were carried out using anti-Gr-1 antibodies to visualize neutrophils. Tissue damage is clearly evident (D3-D4) in the area of neutrophils accumulation in Npc1$^{-/-}$ mouse. D2 and D4 are magnified view of area shown by dotted box in D1 and D3 respectively. Original magnifications, ×400 (D1 &D3) and ×1000 (D2&D4). (E). Attenuated proliferation of *S. typhimurium* in the liver of Npc1$^{-/-}$ mice. Littermates (age 6-8 weeks) Npc1$^{+/+}$, Npc1$^{+/-}$ and Npc1$^{-/-}$, were infected with *S. typhimurium*. Mice were given 1×10$^4$ CFU by i.p injection. At 48 hpi, mice were sacrificed and bacterial CFU was determined. The data obtained from 3 independent experiments. N=10 for Npc1$^{+/+}$ and Npc1$^{-/-}$ and N=8 for Npc1$^{+/-}$. Error bar show the mean±SEM. Student's t test was carried out to determine the statistical significance.

Figure 31:
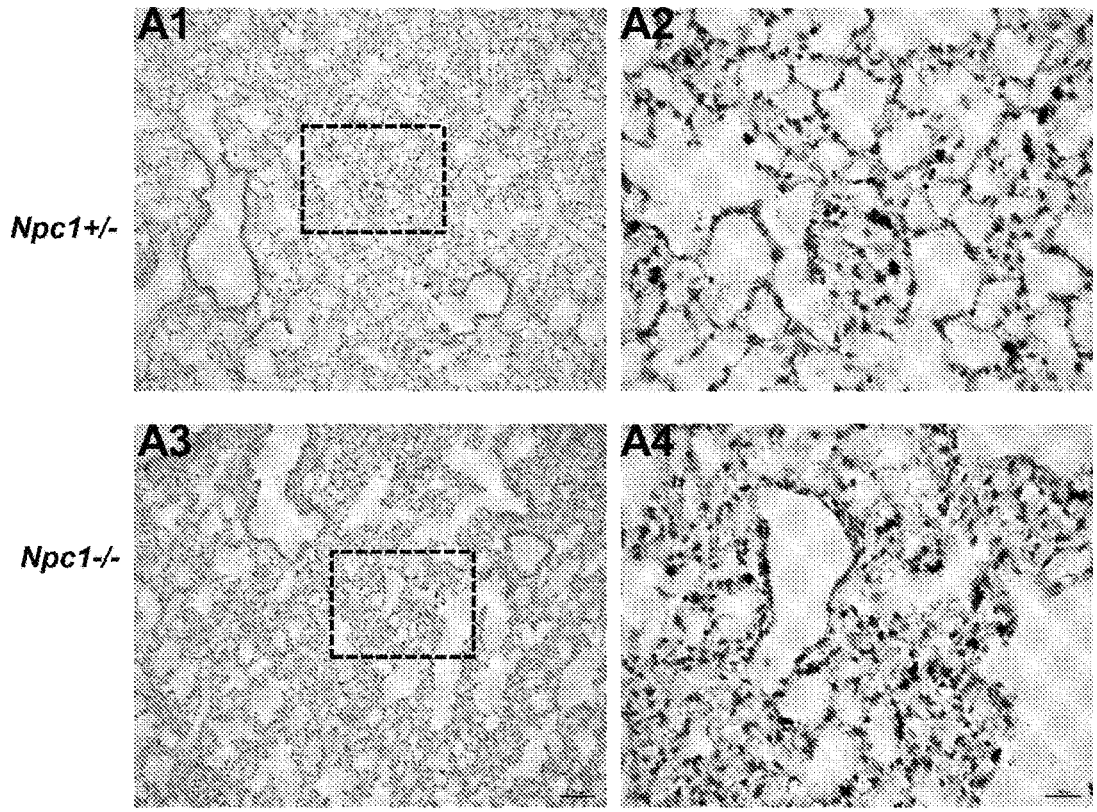

FIG. 31. Neutrophil number increase in lung but not in blood of Npc1$^{-/-}$ mice. (A) Micrographs showing increased infiltration of neutrophils (cells stained in brown) in the alveolar septa of the lung from Npc1$^{-/-}$ mouse (A3-4) compared to Npc1$^{+/-}$ mouse (A1-2), age 48-52 days. Immunohistochemical staining on formalin-fixed paraffin embedded liver sections (3-4 μm) were carried out using anti-Gr-1 to visualize neutrophils. A2 and A4 are magnified view of area shown by dotted box in A1 and A3 respectively Original magnifications, ×100 (A1 &A3) and ×400 (A2&A4). (B) Cellular and hematological parameters are unchanged in Npc1$^{-/-}$ mice. Blood (~20 μl) was collected from female Npc1$^{+/-}$ (n=2, age 63 and 66 days) and Npc1$^{-/-}$ mice (n=2, age 63 and 66 days) by cheek bleed. Blood cell parameters were analyzed by Hemavet 950. Values represent mean±SEM. Abbreviations are, WBC=White Blood Cells, NE=Neutrophils, LY=Lymphocytes, MO=Monocytes, EO=Eosinophils, BA=Basophils, RBC=Red Blood Cells, Hb=Hemoglobin, HCT=Hematocrit, MCV=Mean Corpuscular Volume, MCH=Mean Corpuscular Hemoglobin, MCHC=Mean Corpuscular Hemoglobin Concentration, RDW=Red Cell Distribution width, PLT=Platelet, and MPV=Mean Platelet Volume. K/μl stands for 1000411.

Figure 32:
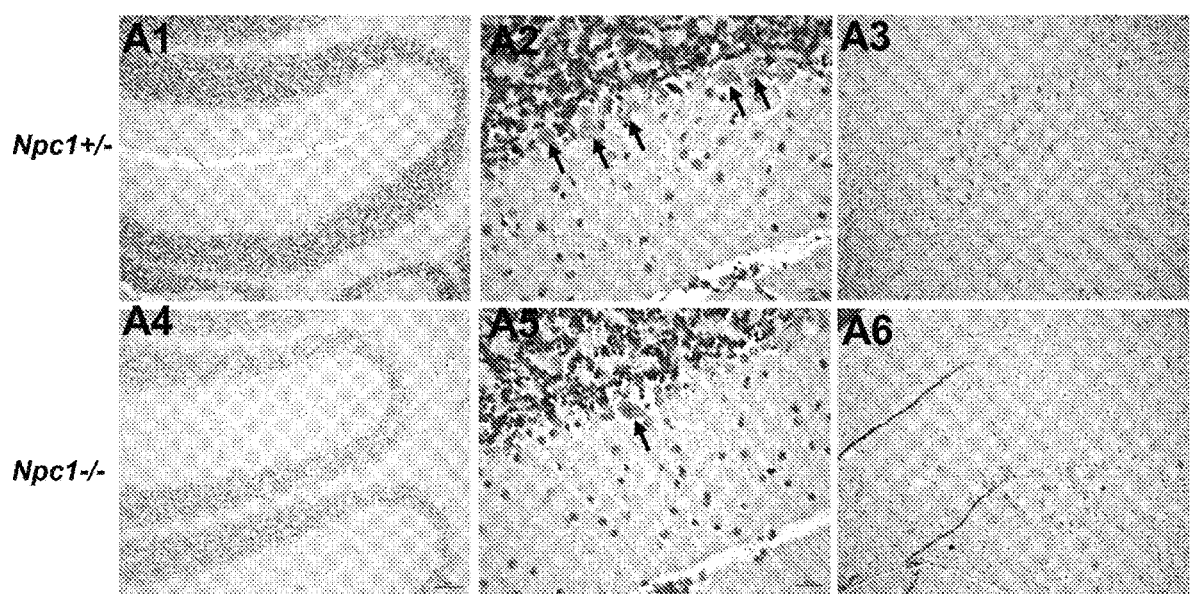

FIG. 32. Neutrophils do not accumulate in the brain of Npc1$^{-/-}$ or Npc1$^{+/-}$ mice. Immunohistochemical staining of formalin-fixed paraffin embedded brain sections of Npc1$^{-/-}$ and Npc1$^{+/-}$ mice (age 48-52 days) was performed using anti-Gr-1 antibodies. The entire brain (sagittal sections) was scanned. Panels are; A1 and A4, cerebellum of Npc1$^{+/-}$ and Npc1$^{-/-}$ mouse respectively; A2 and A5, magnified view of cerebellum of Npc1$^{+/-}$ and Npc1$^{-/-}$ mouse respectively; A3 and A6, magnified view of regions from mid brain of Npc1$^{+/-}$ and Npc1$^{-/-}$ mouse respectively. Several purkinje cells are evident (shown by black arrows) in Npc1$^{+/-}$ (A2) however in Npc1$^{-/-}$ (A5) only few are seen. Original magnifications, ×100 (A1, A3, A4 & A6) and ×400 (A2&A5).

Figure 33:
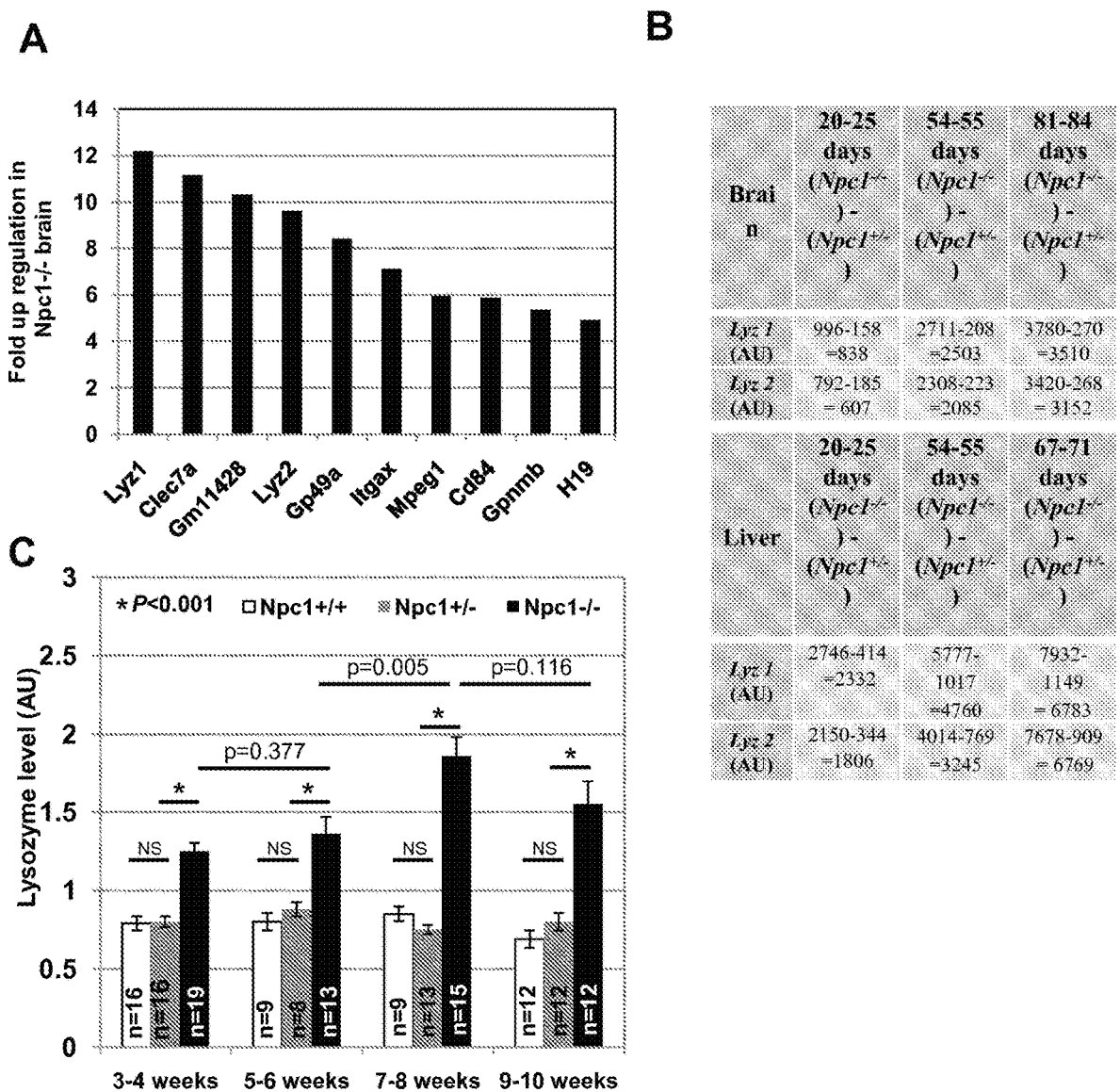

FIG. 33. Lysozyme elevation in brain and plasma of Npc1$^{-/-}$ mice (A) Bar diagram of top 10 up regulated genes in the brain of Npc1$^{-/-}$ relative to control mice. Total RNA from brains of 27 mice (11 Npc1$^{-/-}$ and 16 age matched controls (Npc1$^{+/+}$ and/or Npc1$^{+/-}$) of age ranging 20-84 days (6 age groups, see FIG. 9A for details) were isolated and expression of transcripts were assessed using whole genome, microarray chips. (B) Age dependent enrichment in transcripts of lysozyme and 2 in brain and liver of Npc1$^{-/-}$ mice. Mean expression values obtained in Dchip analyses for Npc1$^{+/-}$ mice were subtracted by the values obtained for Npc1$^{-/-}$ mice at their respective ages and have been denoted in the table. (C) Increased lysozyme activity in the plasma of Npc1$^{-/-}$ mice. Lysozyme activity in the plasma of Npc1$^{+/+}$, Npc1$^{+/-}$ and Npc1$^{-/-}$ mice was assessed using a commercially available fluorescence based lysozyme assay kit (see Materials and Methods). 'n' denotes the number of mice used per group. x-axis denotes the age of mice in weeks at which the plasma lysozyme activity assay was performed. Error bars show the mean±SEM. 'NS' denotes not significant. Student's t test was carried out to determine the statistical significance.

FIG. 34. Weight loss and plasma lysozyme activity in Npc1$^{nmf164}$ mice. (A) Curves showing the weight of Npc1$^{nmf164}$ WT, Npc1, (n=5, females), Npc1$^{nmf164}$ heterozygous mutant, Npc1$^{+/-}$ (n=9, females) and of Npc1$^{nmf164}$ homozygous mutant, Npc1$^{-/-}$ mice (n=5, females). The homozygous mutant mice began weight loss from 12$^{th}$ week of their age. Typically homozygous mutant mice survive 17-18 weeks. The data represent the mean±SD. (B) Lysozyme activity in the plasma of Npc1$^{nmf164}$ WT, Npc1$^{+/+}$, of Npc1$^{nmf164}$ heterozygous mutant, Npc1$^{+/-}$ and of Npc1$^{nmf164}$ homozygous mutant, Npc1$^{-/-}$ mice was tested as described for Npc1$^{nih}$ mice (see Materials and Methods). 'n' denotes the number of mice used per group. Error bars show the mean±SEM. 'NS' denotes not significant (C) Scatter plot shows the plasma lysozyme activity of untreated Npc1$^{nmf164}$ (age 42-49 days) and HPβCD or vehicle treated female mice (age 50-55 days). Each group had five mice. Error bars show the mean±SEM. 'NS' denotes not significant. Student's t test was carried out to determine the statistical significance.

DESCRIPTION OF VARIOUS EMBODIMENTS

It is shown herein that lysozyme and/or cathepsin S detected in a sample can be useful as biomarkers for detecting an increased probability or risk of neurodegeneration in subjects. It is also shown herein that lysozyme and cathepsin S can be used as a composite biomarker. It is also shown herein that lysozyme and cathepsin S can be used to distinguish neuronal degeneration from systemic disease such as liver inflammation.

In some embodiments, the invention provides for a use of lysozyme and cathepsin S as a composite biomarker for detecting an increased probability or risk of neurodegeneration in a subject.

In some embodiments, the invention provides for a use of lysozyme and cathepsin S as a composite biomarker in combination with one or more additional biomarkers for detecting an increased probability or risk of neurodegeneration in a subject.

In some embodiments, the invention provides for a use of lysozyme as a biomarker for detecting an increased probability or risk of neurodegeneration in a subject.

In some embodiments, the invention provides for a use of lysozyme as a biomarker in combination with one or more additional biomarkers for detecting an increased probability or risk of neurodegeneration in a subject.

In some embodiments, the invention provides for a use of cathepsin S as a biomarker for detecting an increased probability or risk of neurodegeneration in a subject.

In some embodiments, the invention provides for a use of cathepsin S as a biomarker in combination with one or more additional biomarkers for detecting an increased probability or risk of neurodegeneration in a subject.

In some embodiments, the invention provides a method for detecting an increased probability or risk of neurodegeneration in a subject comprising assaying a sample from the subject for lysozyme and/or cathepsin S and detecting the lysozyme and/or cathepsin S from the sample, wherein an increased lysozyme and/or cathepsin S compared to levels in a control subject indicate an increased probability or risk of neurodegeneration.

In some embodiments, the invention provides a method for detecting an increased probability or risk of neurodegeneration in a subject comprising assaying a sample from the subject for lysozyme and cathepsin S and detecting the lysozyme and/or cathepsin S from the sample, wherein an increased ratio of lysozyme:cathepsin S in the subject compared to the ratio of lysozyme:cathepsin S in the control subject indicates an increased probability or risk of neurodegeneration.

In some embodiments, the invention provides a method for detecting an increased probability or risk of neurodegeneration in a subject comprising assaying a sample from the subject for lysozyme and cathepsin S and detecting the lysozyme and/or cathepsin S from the sample, wherein an increased ratio of cathepsin S:lysozyme in the subject compared to the ratio of cathepsin S:lysozyme in the control subject indicates an increased probability or risk of neurodegeneration.

In some embodiments, the invention provides a method of screening for drug effectiveness in a subject to treat or prevent neurodegeneration comprising:

i) assaying a sample from the subject for lysozyme and/or cathepsin S and detecting the lysozyme and/or cathepsin S from the sample, wherein an increased lysozyme and/or cathepsin S compared to levels in a control subject indicate an increased probability or risk of neurodegeneration;

ii) administering to the subject an amount of the drug after the assay of step i); and iii) assaying a sample from the subject for lysozyme and/or cathepsin S after the administering of step ii) and detecting the lysozyme and/or cathepsin S from the sample, wherein a reduction in lysozyme and/or cathepsin S in the sample from the subject compared to the lysozyme and/or cathepsin S in the sample from the subject in step i) indicates that the drug may be effective in reducing neurodegeneration.

In some embodiments, the invention provides a method of screening for drug effectiveness in a subject to treat or prevent neurodegeneration comprising:

i) assaying a sample from the subject for lysozyme and cathepsin S and detecting the lysozyme and/or cathepsin S from the sample, wherein an increased ratio of lysozyme:cathepsin S in the subject compared to the ratio of lysozyme:cathepsin S in a control subject indicates an increased probability or risk of neurodegeneration;

ii) administering to the subject an amount of the drug after the assay of step i); and iii) assaying a sample from the subject for lysozyme and cathepsin S after the administering of step ii) and detecting the lysozyme and/or cathepsin S from the sample, wherein a reduction in the ratio of lysozyme:cathepsin S in the subject compared to the ratio of lysozyme:cathepsin S in the sample from the subject in step i) indicates that the drug may be effective in reducing neurodegeneration.

In some embodiments, the invention provides a method of screening for drug effectiveness in a subject to treat or prevent neurodegeneration comprising:

i) assaying a sample from the subject for lysozyme and cathepsin S and detecting the lysozyme and/or cathepsin S from the sample, wherein an increased ratio of cathepsin S:lysozyme in the subject compared to the ratio of cathepsin S:lysozyme in a control subject indicates an increased probability or risk of neurodegeneration;

ii) administering to the subject an amount of the drug after the assay of step i); and iii) assaying a sample from the subject for lysozyme and cathepsin S after the administering of step ii) and detecting the lysozyme and/or cathepsin S from the sample, wherein a reduction in the ratio of cathepsin S:lysozyme in the subject compared to the ratio of cathepsin S:lysozyme in the sample from the subject in step i) indicates that the drug may be effective in reducing neurodegeneration.

In some embodiments, the invention provides a method for distinguishing a probability or risk of neurodegeneration and systemic disease such as inflammation in liver a subject comprising assaying a sample from the subject for lysozyme and cathepsin S and detecting the lysozyme and cathepsin S from the sample, 1) wherein an increased lysozyme and increased cathepsin S compared to levels in a control indicate a relative increased probability or risk of neurodegeneration and a relative increased probability or risk of systemic disease (inflammation in liver);

2) wherein an increased lysozyme and a normal or decreased cathepsin S compared to levels in a control indicate a relative increased probability or risk of neurodegeneration and a relative low probability or risk of systemic disease (inflammation in liver);

3) wherein a normal or decreased lysozyme and a normal or decreased cathepsin S compared to levels in a control indicate a relative low probability or risk of neurodegeneration and a relative low probability or risk of systemic disease (inflammation in liver); and 4) wherein a normal or decreased lysozyme and an increased cathepsin S compared to levels in a control indicate a relative low probability or risk of neurodegeneration and a relative increased probability or risk of systemic disease (inflammation in liver).

In another aspect, the invention provides a method for screening a drug to distinguish the effectiveness of reducing the probability or risk of neurodegeneration and the effectiveness of reducing the probability or risk of systemic disease such as inflammation in liver, comprising i) assaying a sample from a subject for lysozyme and cathepsin S and detecting the lysozyme and cathepsin S from the sample,
  1) wherein an increased lysozyme and increased cathepsin S compared to levels in a control indicate a relative increased probability or risk of neurodegeneration and a relative increased probability or risk of systemic disease (inflammation in liver);
  2) wherein an increased lysozyme and a normal or decreased cathepsin S compared to levels in a control indicate a relative increased probability or risk of neurodegeneration and a relative low probability or risk of systemic disease (inflammation in liver);
  3) wherein a normal or decreased lysozyme and a normal or decreased cathepsin S compared to levels in a control indicate a relative low probability or risk of neurodegeneration and a relative low probability or risk of systemic disease (inflammation in liver);
  4) wherein a normal or decreased lysozyme and an increased cathepsin S compared to levels in a control indicate a relative low probability or risk of neurodegeneration and a relative increased probability or risk of systemic disease (inflammation in liver);
ii) administering to the subject an amount of the drug after the assay of step i); and
iii) assaying a sample from the subject for lysozyme and cathepsin S after the administering of step ii) and detecting the lysozyme and cathepsin S from the sample,
  5) wherein if the subject exhibits a profile corresponding to i)1) prior to administering and following administering exhibits a profile corresponding to i)4), then the drug is relatively more effective at reducing the probability or risk of neurodegeneration than reducing the probability or risk of systemic disease (inflammation in liver);
  6) wherein if the subject exhibits a profile corresponding to i)1) prior to administering and following administering exhibits a profile corresponding to i)2), then the drug is relatively more effective at reducing the probability or risk of systemic disease (inflammation in liver) compared to the probability or risk of neurodegeneration;
  7) wherein if the subject exhibits a profile corresponding to i)2) prior to administering and following administering exhibits a profile corresponding to i)3), then the drug is effective at reducing the probability or risk of neurodegeneration;
  8) wherein if the subject exhibits a profile corresponding to i)4) prior to administering and following administering exhibits a profile corresponding to i)3), then the drug is effective at reducing the probability or risk of systemic disease (inflammation in liver).

The source of the sample is not limiting. In some embodiments, the sample is selected from the group consisting of blood, plasma, serum, saliva, urine, tears, cerebrospinal fluid and combinations thereof. In some embodiments the sample is plasma. In some embodiments, the sample is any type of cells or tissue obtained from the subject.

In some embodiments, the control is an age matched subject. In some embodiments, the control subject is a gender matched. In some embodiments, the levels are compared to a mean value or median value obtained from a pool of subjects that are age and/or gender matched.

In some embodiments the subject's age differs from the control by less than 15 years, less than 10 years, less than 9 years, less than 8 years, less than 7 years, less than 6 years, less than 5 years, less than 4 years, less than 3 years, less than 2 years, or less than 1 year.

In some embodiments, the control lacks evidence of neurodegeneration.

In some embodiments, the subject is suspected of having a neurodegenerative disease or is at risk for a neurodegenerative disease.

In some embodiments, the neurodegeneration is caused by a disease selected from the group consisting of Alpha-mannosidosis, Cystinosis, Danon disease, Fabry disease, Farber disease, Fucosidosis, Galactosialidosis, Gaucher Disease (Type1, TypeII, TypeIII), GM1 gangliosidosis (infantile, juvenile and adult), I-Cell disease (Mucolipidosis II), Infantile Free Sialic Acid Storage Disease, Juvenile Hexosaminidase A Deficiency, Krabbe disease (Infantile and late onset), Lysosomal acid lipase deficiency (early and late), Metachromatic Leukodystrophy, Pseudo-Hurler polydystrophy (Mucolipidosis IIIA), MPSI (Hurler Syndrome), MPS II (Hunter syndrome), Sanfilippo syndrome Type A (MPS III A), Sanfilippo syndrome Type B (MPS III B), Sanfilippo syndrome Type C (MPS III C), Sanfilippo syndrome Type D (MPS III D), Morquio Type A (MPS WA), Morquio Type B (MPS IVB), MPS IX (Hyaluronidase Deficiency), MPS VI (Maroteaux-Lamy), MPS VII (Sly Syndrome), Mucolipidosis I (Sialidosis), Mucolipidosis IIIC, Mucolipidosis type IV, Multiple sulfatase deficiency, Niemann-Pick Disease, Type A, Niemann-Pick Disease, Type B, Niemann-Pick Disease, Type C, Neuronal Ceroid Lipofuscinoses, Pompe disease, Pycnodysostosis, Sandhoff disease (infantile, juvenile and adult), Schindler disease, Salla disease (Sialic Acid Storage Disease), Tay-Sachs disease, Wolman disease, chronic traumatic encephalopathy, Alzheimer's disease (AD), Parkinson disease (PD), Huntington disease (HD), Frontotemporal dementia (FTD-3 subtype), Amyotrophic lateral sclerosis (ALS), Charcot-Marie Tooth disease type 2B, Neuronal ceroid lipofuscinoses/Batten disease (NCL), Creutzfeldt-Jakob disease, Autosomal dominant Spastin hereditary spastic paraplegia (ADHSP), Chediak-Higashi syndrome (CHS), and Inclusion body myositis (IBM).

The method of assaying for the level of lysozyme and/or cathepsin S is not limiting. In some embodiments, the protein level of the lysozyme and/or cathepsin S is assayed using an antibody. In some embodiments, the lysozyme and/or cathepsin S is assayed using an enzymatic assay to detect the activity of the lysozyme and/or activity cathepsin S in the sample.

In some embodiments, the subject is a mammal selected from humans, primates, monkeys, chimpanzees, dogs, cats, sheep, cattle, goats, pigs, horses, chickens, mice, rats, rabbits, and guinea pigs. In some embodiments, the subject is a mammal. In some embodiments, the mammal is an animal model for a neurodegenerative disease. In some embodiments, the subject is suspected of having neurodegeneration or is at risk of neurodegeneration. In some embodiments, the subject is being treated with a therapy for neurodegeneration.

Lysozyme can be assayed independently of cathepsin S and vice versa. In some embodiments, both lysozyme and cathepsin S are assayed.

In some embodiments, lysozyme is increased compared to the levels in the control. In some embodiments, lysozyme is increased compared to the levels in the control but the cathepsin S is not increased relative to the control.

In some embodiments, the lysozyme and the cathepsin S are increased compared to the levels in the control.

In some embodiments, the cathepsin S is increased compared to the levels in the control.

In some embodiments, the cathepsin S is increased compared to the levels in the control, but the lysozyme is not increased compared to the levels in the control.

In some embodiments, the lysozyme and/or cathepsin S are increased by an amount selected from the group consisting of at least 10% relative to the control, at least 20% relative to the control, at least 30% relative to the control, at least 40% relative to the control, at least 50% relative to the control, at least 60% relative to the control, at least 70% relative to the control, at least 80% relative to the control, at least 90% relative to the control, and at least 100% relative to the control.

In some embodiments, the lysozyme is compared to a median lysozyme value from the control. In some embodiments, the median value is 4.92 ug/ml (plasma)±2%, 5%, 10%, 15%, 20%, 25%, 35%, 50%, and 75%.

In some embodiments, the cathepsin S is compared to a median cathepsin S value from the control. In some embodiments, the median value is 54.52 ug/ml (plasma)±2%, 5%, 10%, 15%, 20%, 25%, 35%, 50%, and 75%.

Other assays and tests can be combined with the methods of the invention. In some embodiments, the methods further comprise performing neuroimaging on the subject to assay for neurodegeneration. In some embodiments, the neuroimaging is selected from the group consisting of magnetic resonance imaging (MRI), computed tomography (CT), and positron emission tomography. In some embodiments, one or more tracers are administered to the subject to facilitate the neuroimaging.

In some embodiments, the methods further comprise administering to the subject an effective amount of a drug for the treatment or prevention of the neurodegeneration in the subject. In some embodiments, a drug is administered when the subject has a probability of neurodegeneration or is at risk based on the increased lysozyme and/or cathepsin S levels compared to the control. The methods can also be used to assess drug effectiveness or for screening purposes or to distinguish whether the drug is effective to treat neurodegeneration or systemic disease such as liver inflammation.

In some embodiments, the drug to be administered in the methods in accordance with the invention are described in U.S. Provisional Application No. 62/011,553, filed Jun. 12, 2014 and U.S. Provisional Application No. 61/935,791, filed Feb. 4, 2014, which are herein incorporated by reference.

In some embodiments, the drug is selected from the group consisting of cyclodextrin, hydroxy propyl beta cyclodextrin (HPBCD), polymer of HPBCD, Miglustat/Zavesca, Vorinostat, 1-Deoxygalactonojirimycin (DJG), 4-Phenylbutyric Acid (PBA), Chlorpromazine, Cisapride, Benzo(c)quinolizinium compound, Naltrexone, histone deacetylase (HDAC) inhibitor, Amyloidosis inhibitor, a salt, prodrug, hydrate, derivative or metabolite, analogue, derivative and combinations thereof. In some embodiments, the histone deacetylase (HDAC) inhibitor is selected from the group consisting of Vorinostat, Valproic acid, Entinostat (MS-275), Panobinostat (LB H589), Trichostatin A (TSA), Droxinostat(CMH), JNJ-26481585, PCI-24781(CRA-024781), PCI-34051, Romidepsin (FK228), CI994 (Tacedinaline), M344, Rocilinostat (ACY-1215), Apicidin, a salt, prodrug, hydrate, derivative or metabolite, analogue, derivative and combinations thereof.

In some embodiments, the drug modulates intracellular calcium levels. In some embodiments, the drug is selected from the group consisting of Thapsigargin, Curcumin, 25-dihydroxyvitamin D3, a salt, prodrug, hydrate, derivative or metabolite, analogue, derivative and combinations thereof.

In some embodiments, the subject is administered one or more cognitive functioning tests and/or the subject is assayed for the presence or absence of one or more additional biomarkers of neurodegeneration.

In some embodiments, the invention provides kits for carrying out any one of the methods or uses comprising one or more reagents for detection of lysozyme and/or cathepsin S from a sample. In some embodiments, the kit comprises one or more primary antibodies that detect lysozyme, and/or one or more primary antibodies that detect cathepsin S, and optionally one or more labeled secondary antibodies. In some embodiments the kit comprises one or more reagents to test for the enzymatic activity of lysozyme and/or cathepsin S. In some embodiments, the kit comprises one or more plasma samples from a control. In some embodiments the kit comprises one or more drugs to treat or screen for neurodegeneration in a subject.

While the embodiments have been described with reference to certain particular examples and embodiments herein, those skilled in the art will appreciate that various examples and embodiments can be combined for the purpose of complying with all relevant patent laws (e.g., methods described in specific examples can be used to describe particular aspects of the embodiments and its operation even though such are not explicitly set forth in reference thereto).

Aspects of the present teachings may be further understood in light of the following examples, which should not be construed as limiting the scope of the present teachings in any way.

Example 1

Genomic Expression Analyses Reveal Lysosomal, Innate Immunity Proteins, as Disease Correlates in Murine Models of a Lysosomal Storage Disorder Niemann-Pick Type C (NPC) is a neurodegenerative, lysosomal disorder caused by defects in function of either genes Npc1 or Npc2, although in 95% of patients disease is caused by defect in Npc1 [1]. There is resulting defect in cellular transport of lipids, characterized by accumulation of both unesterified cholesterol and sphingolipids in late endosomal/lysosomal compartments. Inflammatory changes have been reported in the liver, spleen and brain of NPC animals [2,3,4,5] and anti-inflammatory treatments have been shown to reduce disease burden in mice [4,6]. Prior work suggests that antisense mediated knock down of Npc1 in C57BL/6 mice results in tumor necrosis factor α (TNF-α)-dependent accumulation of inflammatory cells in liver [2,7]. Foamy macrophage accumulation in liver activation of microglia in brain [2] and impaired development and reduced natural killer T (NKT) cells in spleen and thymus have been reported [10,11] in NPC null mice. Changes in inflammatory cells and protein markers [4,7,12] appear consistent with organ specific (largely the brain) analysis of transcripts [5,13,14]. Expression arrays have also been utilized to investigate transcriptional changes in cell culture [15,16]. However comprehensive, unbiased, genome wide analyses of changes in gene expression in a leading organ of interest, the brain, across the life span, especially as animals transition from a phenotypically asymptomatic state to manifesting major disease symptoms, is not yet available. Further whether age-dependent gene expression in the brain is linked if at all, to that in the liver and/or spleen two organs that manifest early disease symptoms, is also not known. Genes expressed in an age-dependent manner in both brain and liver (the source of plasma proteins) would facilitate identification of blood-based biomarkers that reflect cerebral disease.

Consistent with increase in their inflammatory mechanisms, NPC disease cells and/or animals have been shown to be refractory to infection by HIV-1 and *Brucella abortus* [17,18]. However resistance of NPC cells and animals to infection may also occur because cholesterol and endosomal trafficking are known to play critical roles in vacuolar infection of virus, bacteria and parasites in a variety of different hosts [19,20,21,22]. More recently, NPC1 has been shown to act as an invasion receptor for Ebola and Marburg viruses [23,24], suggesting a direct role for NPC1, possibly independent of cholesterol trafficking in the infection of filoviridae. However, whether cellular mechanisms controlling microbial proliferation in organ systems are altered, is not known.

*Salmonella enterica* serovar *Typhimurium* (*S. typhimurium*), a Gram-negative, rod shaped, facultative intracellular bacterial pathogen, is a major cause of food-borne enterocolitis in humans as well as a typhoid-like disease in mice [25,26]. Due to the ease with which it can be genetically manipulated, quantitatively analyzed both in vitro and in mouse models of infection, *Salmonella* is often used as a model system to investigate cellular and organismal processes of mammalian hosts. Replication in the liver and spleen is essential for dissemination of *Salmonella* [26,27]. These organs also manifest the earliest pathologies of NPC. However, whether NPC1 defects influence *Salmonella* virulence, and/or proliferation in vivo, is not known. In both liver and spleen, if loss of the Npc1 gene influences expression of genes important for host response to *Salmonella* infection, the underlying basis can be rapidly validated with well-developed cellular assays and other functional read outs.

We have performed non-biased, genome wide expression profiling analyses to discover increase in a restricted subset of innate immunity transcripts as a major transcriptional change in the brain, across the life span of the $Npc1^{-/-}$ mouse. Expression profiling of liver and spleen also established up-regulation of innate immunity transcripts. By comparative analyses of up regulated brain and liver genes, we identify 12 secretory proteins that have potential to be developed as plasma correlates measuring transition to NPC disease in the brain. As a proof of concept, we validated the top hit lysozyme in plasma. Further we confirmed functional elevation of innate immunity mechanisms in both liver and spleen by following resistance to infection by *S. typhimurium* as a model organism. We also report for the first time, neutrophil elevation in liver and spleen of $Npc1^{-/-}$ mice that may play a role in NPC pathophysiology and disease exacerbation.

Figure 1:
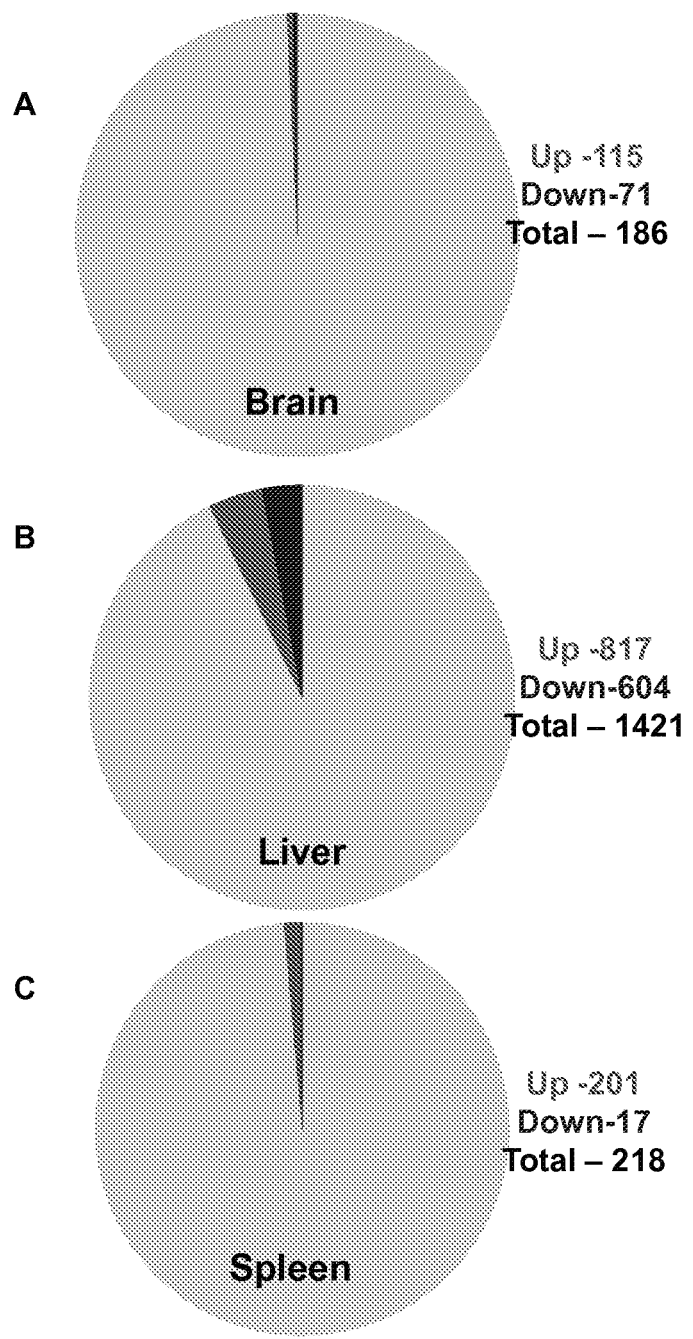
FIG. 1. Genome-wide gene-expression profiling on brain, liver and spleen of Npc1$^{-/-}$ mice. (A) Brain. Pie chart displays 0.46% up regulated and 0.28% down regulated transcripts relative to the total number of transcripts (24615) expressed in the brain of Npc1$^{-/-}$ mice across the life span. Total RNA from brain of 27 mice (11 Npc1$^{-/-}$ and 16 age matched controls) age ranging from 20-84 days (6 age groups, see FIG. 9A for details) were isolated and gene expression was analyzed using affymetrix microarray chips (see Materials and Methods). The expression level of 186 genes (115 up and 71 down) in the Npc1$^{-/-}$ mice changed by 1.5 fold or higher (p<0.05). (B) Liver. Pie chart displays 4.44% up regulated and 3.28% down regulated transcripts relative to the total number of transcripts (18377) expressed in the liver of Npc1$^{-/-}$ mice across the life span. Total RNA from the liver of 12 mice (6 Npc1$^{-/-}$ and 6 age matched Npc1$^{+/-}$) age ranging 20-71 days (3 age groups, see FIG. 9B for details) were isolated and transcript expression was analyzed as described for the brain. The expression of 1421 genes (817 up and 604 down) in the liver of Npc1$^{-/-}$ mice changed by 1.5 fold or higher (p<0.05). (C) Spleen. Pie chart displays 1.3% up regulated and 0.11% down regulated transcripts relative to the total number of transcripts (15348) expressed in the spleen of Npc1$^{-/-}$ mice across the life span. Experimental set up and analysis criteria were identical to that described for the liver. The expression of 218 genes (201 up and 17 down) in the spleen of Npc1$^{-/-}$ mice changed by 1.5 fold or higher (p<0.05).

Results
Genome-Wide Gene-Expression Analyses in Brain, Liver and Spleen of $Npc1^{-/-}$ Mice from Weaning Through Advanced Neurodegeneration Progressive neurological dysfunction is a prominent feature of NPC disease, and hence understanding correlates in the brain is of critical importance to understanding disease progression. To comprehensively cover the life span, we examined transcripts in brain from animals from ~20 days to 80 days (FIG. 9) reflecting the period from weaning, when the animals are completely asymptomatic to advanced neurodegeneration and significant weight loss (~30% reduction is observed by 60-80 days) characteristic of this model Across this range, six time points (days 20-25, 37-40, 54-55, 59-62, 67-71, and 81-84) were utilized to closely map the life span of $Npc1^{-/-}$ mice. For each point, transcripts of brains from two $Npc1^{-/-}$ mice were compared to age matched, $Npc1^{+/-}$ mice. $Npc1^{+/+}$ animals were also included for days 20-25 and 59-62 and 67-71 (as outlined in FIG. 9A) to enable comparative analysis across all three genotypes. Due to technical difficulties, RNA yield from one animal ($Npc1^{-/-}$, 71 days) was low and thus at this time point transcript data from only one $Npc1^{-/-}$ animal was included (whose exclusion had no adverse effect on inferences drawn from the global data set: data not shown). Our data analysis selected for genes whose expression was significantly altered between $Npc1^{-/-}$ mice relative to $Npc1^{+/-}$ and/or $Npc1^{+/+}$ mice at all time points (see Materials and Methods, Table S1). Because one gene may be represented multiple times on the array chip, we removed the replicates. As shown in FIG. 1A, and Table S1, 115 genes were up regulated (red), and 71 were down regulated (blue), suggesting that less than one percent of the total number of genes were consistently changed in the brain throughout the animal's life span.

Figure 9A:
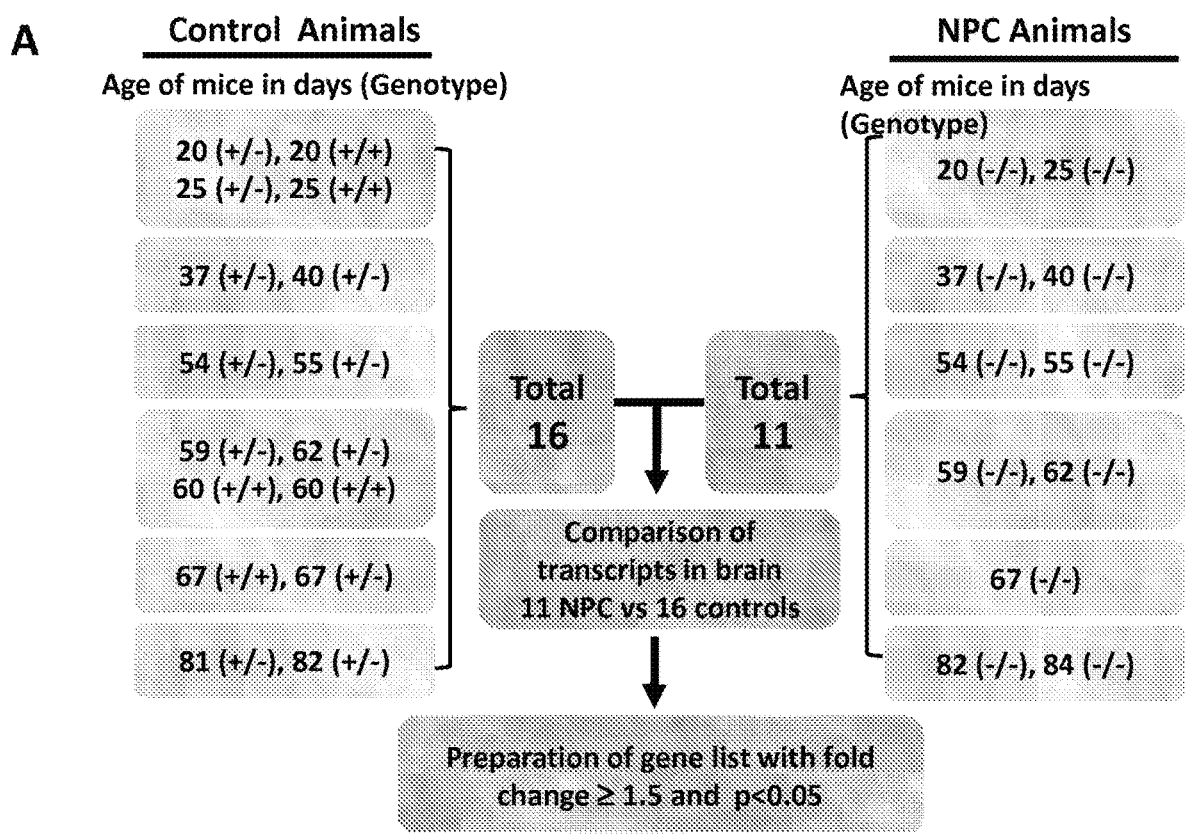
FIG. 9. Pictorial representation of the experimental design of whole-genome gene-expression analysis for brain, spleen and liver (A) Chart displaying the experimental set up for the microarray experiment using brain from 27 mice (11 Npc1$^{-/-}$ and 16 controls) age ranging from 20-84 days. (B) Chart displaying the experimental set up for the microarray experiment using liver or spleen from 12 mice (6 Npc1$^{-/-}$ and 6 controls) age ranging from 20-71 days. +/+ denotes Npc1$^{+/+}$, +/- denotes Npc1$^{+/-}$ and -/- denotes Npc1$^{-/-}$ mice.
Figure 9B:
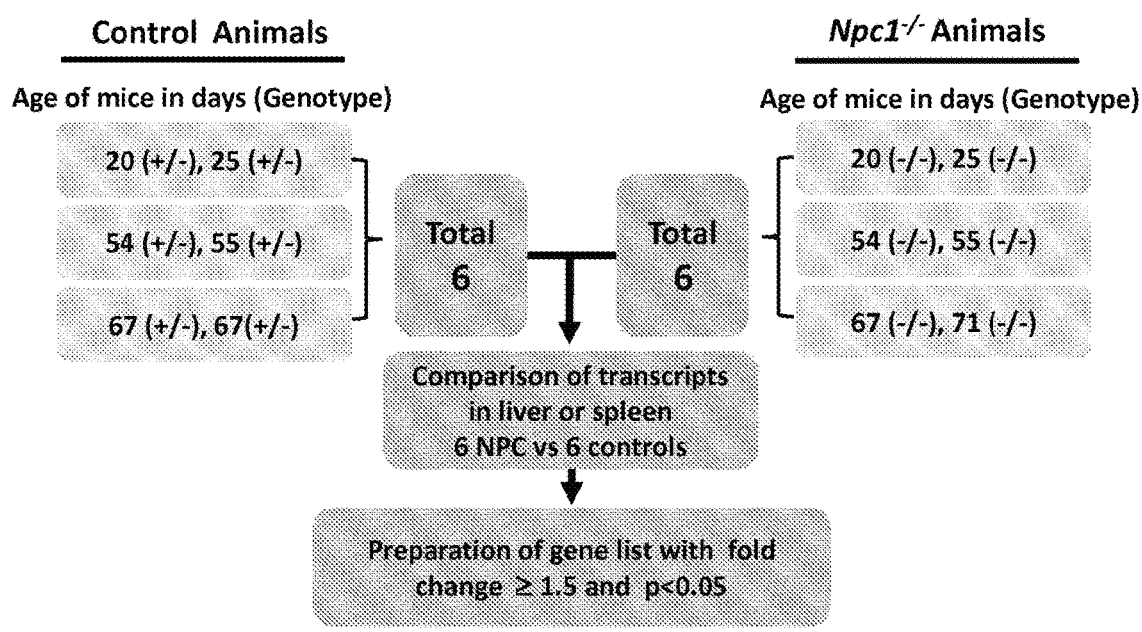

Since enlargement of the liver and spleen are early indicators of NPC, we were also interested in examining corresponding changes in these organs. For both liver and spleen, we examined three of the six time points utilized for brain analysis. Thus pairs of $Npc1^{-/-}$ mice relative to age-matched $Npc1^{+/-}$ at 20-25 days, 54-55 days and 67-71 days were analyzed for each organ (FIG. 9B). This age range was sufficient to cover animals immediately post weaning and the transition from asymptomatic (20-25 days) into symptomatic animals (that arises between 45 to 60 days) in this model [28,30,31]. As shown in FIG. 1B and Table S2, in the liver, 1421 genes showed consistent change through these age groups in $Npc1^{-/-}$ mice. 817 were reliably up regulated and 604 were down regulated. In contrast in the spleen, 218 and 17 transcripts were respectively up- and down-regulated in $Npc1^{-/-}$ mice compared to $Npc1^{+/-}$ (FIG. 1C and Table S3). Hence, compared to the brain and spleen, the liver showed the greatest number of changes manifest throughout the life span, which is consistent with significant liver dysfunction associated with this disease.

Figure 2:
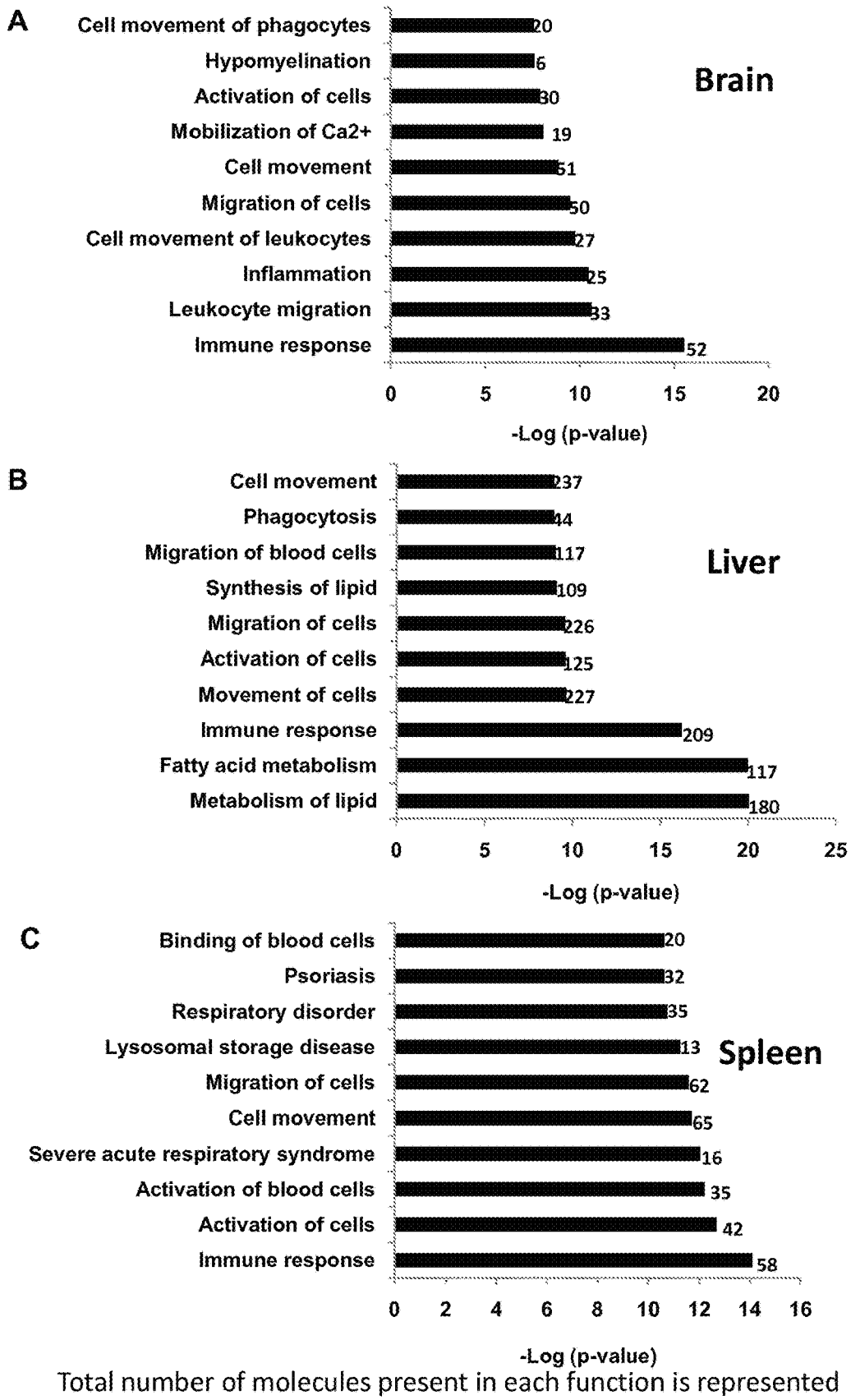
FIG. 2. Enrichment of top 10 biofunctions pathways in brain, liver and spleen of Npc1$^{-/-}$ mice (A) The top 10 biofunctions pathways derived from IPA analyses of differentially expressed genes in the brain of Npc1$^{-/-}$ mice and ranked by 'p values' (lowest to highest) are shown. The numbers along each bar represent the total number of differentially expressed genes (both up and down regulated) categorized in each biofunction (see also Table S4). A total of 53 genes (45 up and 8 down regulated) associated with immune response were enriched in the brain of Npc1$^{-/-}$ across all time points (B) Bar diagram shows the top 10 biofunctions enriched in the liver of Npc1$^{-/-}$ compared to Npc1$^{+/-}$. A total of 209 genes (159 up and 50 down regulated) associated with the immune response were enriched in the liver of Npc1$^{-/-}$ across all time points (see also Table S4). (C) Bar diagram shows the top 10 biofunctions enriched in the spleen of Npc1$^{-/-}$ compared to Npc1$^{+/-}$. A total of 58 genes (49 up and 9 down regulated) associated with the immune response were enriched in the spleen of Npc1$^{-/-}$ across all time points (see Table S4).

Over Expression of Innate Immunity Genes in Brain, Liver and Spleen Across the $Npc1^{-/-}$ Mice Life Span To gain further insights, genes showing significantly altered expression were then subjected to Ingenuity Pathway Analysis (IPA) to identify the top 10, significantly associated biofunctions. In the brain, immune response function comprising of 53 genes (45 up regulated and 8 down) was the top most enriched function (FIG. 2A and Table S4). In the liver, immune response function comprising of 209 genes (159 up regulated and 50 down regulated) was the third from the top. (FIG. 2B and Table S4). In spleen, immune response functions comprising of 58 genes (49 up regulated and 9 down regulated) was also the top function (FIG. 2C and Table S4).

Strikingly, many of the genes associated with the immune response biofunctions appeared to link to innate immunity. In the brain, at least 29 differentially expressed genes (28 up and 1 down regulated) were found in InnateDB, a leading database for innate immunity genes (www.innatedb.ca/) [32] (Table S1, shown in bold letters). As shown in Table 1 (marked in bold), of the top five genes up regulated in brain, four were annotated to be Lysozyme1, Clec7A, Lysozyme2, Gp49a. All play a role in innate immunity [33,34,35]. In the next fifteen up regulated genes, eleven were related to innate immunity, namely Itgax, Mpeg1, Gpnmb, Fcgr2b, Tnfatp2, Cd68, Ifit1, C4b, C3ar1, Usp18 and Trem2 (Table 1, marked in bold). Other up regulated innate immunity transcripts belonged to major histocompatibility complex (H2-d1, H2-k1, H2-1 and H2-t23), Fc receptors (Fcgr2b, Fcgr3, Fcer1g and Fcrls), complement system (C1qa, C1qb, C1qc, C4b, and C3ar1), cathepsins, (Ctsb, Ctsd. Ctss and Ctsz), galactose binding lectins (Lgals1, Lgals3, Lgals9 and Lgals3bp), interferon induced proteins (Ifit1, Ifit3, Ifitm2, Ifitm3, Ifi35, Ifi44 and Ifi2712a) etc (Table S1, marked in bold).

Our data are consistent with prior studies in the literature examining transcriptional changes in the brain at individual time points or multiple time points over a short age range [5,13,14,28,36]. Thus, genes like Lyz1/2, Cd84, Cd68, C1qa, C1qb, Ifit3, Ptprc, H2-d1, H2-k1 etc have been previously shown to be increased early in mouse brain [13]. Additional innate immunity genes previously described in the brain of NPC mice are Mpeg1, Gpnmb, Ctss, Ctsd, Ctsz, Gm, Clec7a, Itgax, Gp49a, Hexb, Lgls3bp, Tyrobp etc [5,13,14]. It should be noted that at a given time point, a relatively large number of genes are altered as described earlier [5,13]. However our data show that smaller subsets of these genes are consistently up regulated across the animal life span.

In the liver, both the number of genes and fold change in gene expression were greater compared to the brain. Changes in gene expression seen in the top 20 up regulated genes were relatively large and ranged from ~80 to 15 fold (Table 2). InnateDB identified 123 genes to be innate immunity genes of which 101 were up- and 22 were down-regulated (Table S2, shown in bold). In the top 20 most up regulated genes, eleven are reported to have roles in innate immunity and/or antimicrobial activity against viruses, bacteria and/or fungi (Table 2, marked in bold). Of these, Mmp12, Lgals3, Clec4d, Clec7a, Camp, Slamf7 and Bcl2a1 are incorporated in InnateDB. Other top 20 innate immunity determinants include Gpnmb, Il7r, Pou3f1/Oct 6 and Capg [37,38,39,40,41]. Additional prominent innate immune genes up regulated were cathepsins (Ctsb, Ctsd, Ctss), galectins (Lgals1, Lgals3), phagocyte oxidases (Cyba, Cybb. Ncf2) and toll like receptors (Tlr1. Tlr13) (Table S2, marked in bold).

Gene expression analysis in the spleen also suggested up regulation of innate immunity genes. InnateDB identified 35 genes of which 32 were up- and 3 were down-regulated (Table S3, shown in bold). Of the top 20 up regulated genes, 6 were innate immunity genes, five (Clec7a, Atf3, Mmp12, Msr1 and Elane) of which were found in InnateDB (Table 3, marked in bold). The sixth Gpnmb [41], was also up regulated in the brain and liver. Additional, prominent up regulated innate immunity genes were annexins (Anxa1, Anxa4), Ctsb, Ctsd, Lgals1, Lgals3, that were over expressed in brain and liver and Mmp9 and Camp, also over expressed in liver (Table S2, marked in bold).

Prioritization of Plasma Correlates Predictive of Cerebral Disease

There is as yet, no blood-based biomarker for NPC and this greatly delays diagnosis of the disease, which can take on average of five years [42,43] Recent studies suggest that elevation of oxysterols in plasma could well be developed into the first blood-based diagnostic for NPC [44]. However, despite their maximal elevation in Npc1$^{-/-}$, oxysterols also show slight increase in Npc1$^{+/-}$ animals. Further, oxysterols may not respond to substrate reduction therapies such as miglustat (Zavesca) that reduces levels of sphingolipids rather than cholesterol [45], suggesting need for multiple biomarkers.

Figure 3:
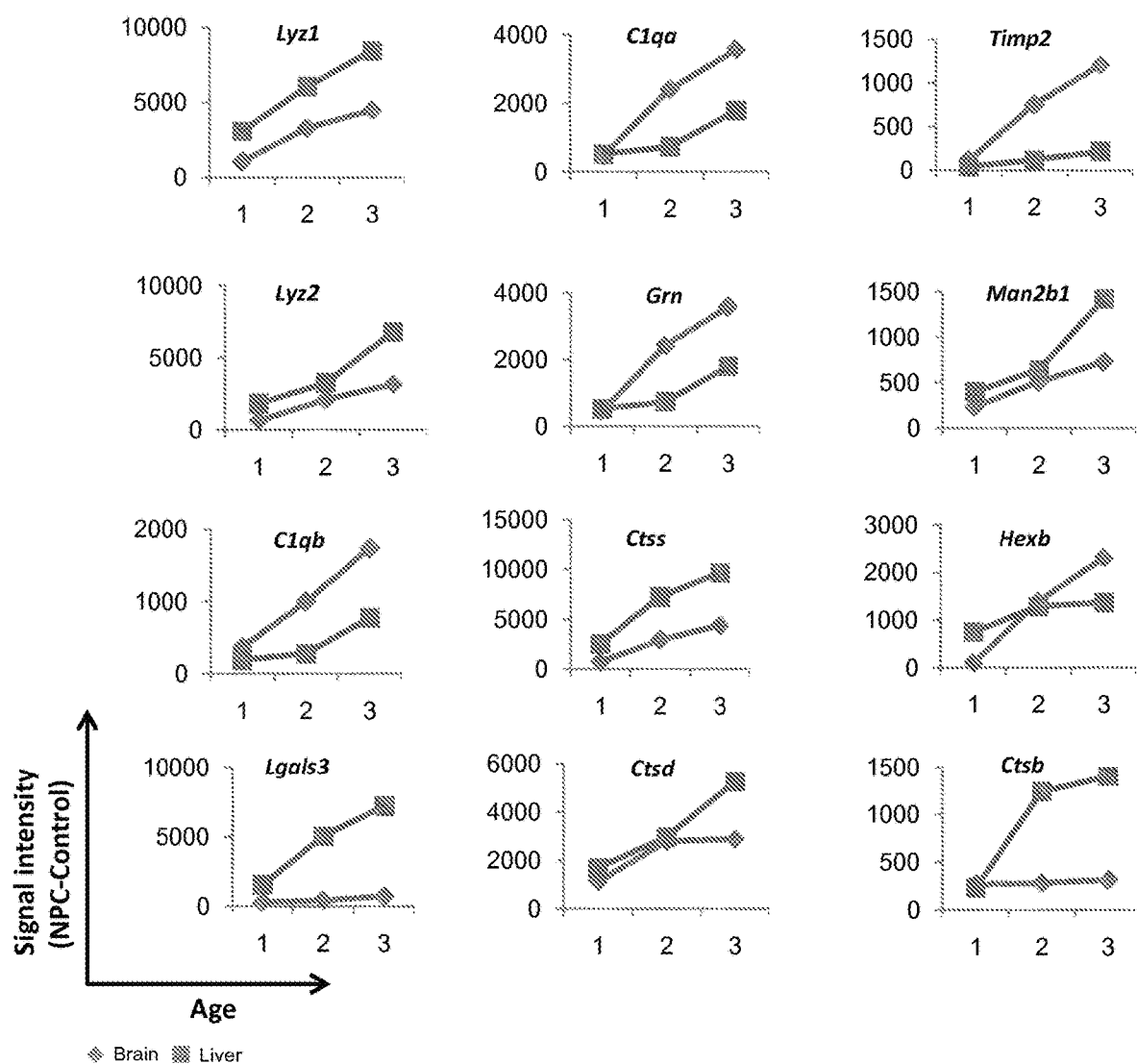
FIG. 3. Age dependent over expression of 12 potential secretory genes in brain and liver of Npc1$^{-/-}$ mice. The raw signal intensity of all 12 genes obtained after Dchip analysis of brain and liver at three distinct time points (1 corresponds to 20-25 days, 2 corresponds to 54-55 days and 3 corresponds to 67-71 days for liver and 81-84 days for brain) were taken and the mean was calculated. Mean signal intensity obtained from 2 Npc1$^{+/-}$ mice was subtracted from the mean values of 2 Npc1$^{-/-}$ mice corresponding to same age group. The process was undertaken for each gene at all three time points for both brain and liver. The difference obtained for each time point is plotted.
Figure 10:
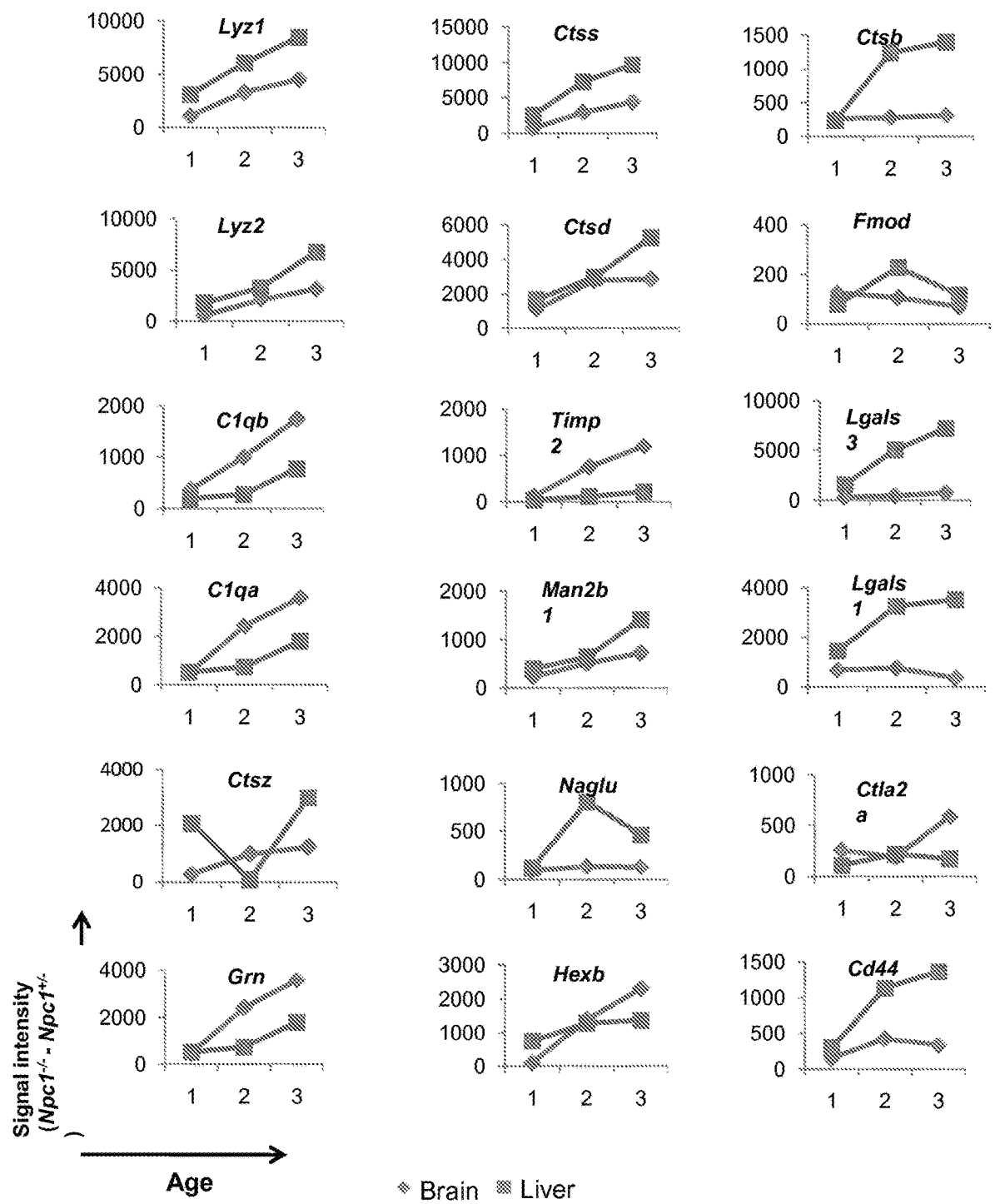
FIG. 10. Age-dependent over expression of 18 secretory genes in brain and liver of Npc1$^{-/-}$ mice. The raw signal intensity of all 18 genes obtained after the Dchip analysis of brain and liver transcripts at three time points (1 corresponds to 20-25 days, 2 corresponds to 54-55 days and 3 corresponds to 67-71 days for liver and 81-84 days for brain) were taken and mean value was calculated. Mean signal intensity of 2 Npc1$^{+/-}$ mice was subtracted from the mean signal intensity values of 2 Npc1$^{-/-}$ mice between age-matched animals. The process was carried out for each gene at all three time points for both brain and liver. The difference obtained was plotted as a function of time.

To develop a prioritized set of plasma proteins that are linked to correlates of disease in the brain, we identified genes of soluble secretory proteins that are up regulated in the NPC brain as well as the liver (the major source of plasma proteins) at all time points. This led to the identification of 18 genes namely Lyz1 (Lysozyme1), Lyz2 (Lysozyme2), C1qb (Complement component 1qb), Lgals3 (Lectin galactose binding soluble3, also known as Galectin 3), C1qa (Complement component 1qa), Ctsz (Cathepsin Z), Cd44 (CD44 antigen), Grn (Granulin), Ctss (Cathepsin S), Ctsd (Cathepsin D), Lgals1 (Lectin galactose binding soluble1), Timp2 (Tissue inhibitor of metalloproteinase 2), Ctla2a (Cytotoxic T lymphocyte-associated protein 2 alpha), Man2b1 (Mannosidase2 alpha B1), Naglu (Alpha-N-acetyl-glucosaminidase), Hexb (Hexoseaminidase B), Ctsb (Cathepsin B), and Fmod (Fibromodulin) (Table S5). Of these, 12 showed progressive, age dependent change in both brain and liver, that is desired in a disease marker (FIG. 3 and FIG. 10). In the order of their elevation in the brain, these are Lyz1, Lyz2, C1qb, Lgals3, C1qa, Gm, Ctss, Ctsd, Timp2, Man2b1, Hexb and Ctsb (Table 4 and FIG. 3). Remarkably, other than Man2b1 and Hexb, the remaining ten are innate immune genes of which eight are lysosomal. All 12 may be putative, plasma predictors of the transition to cerebral disease.

Elevated Lysozyme Activity in the Plasma of Npc1$^{-/-}$ Mice

Figure 4:
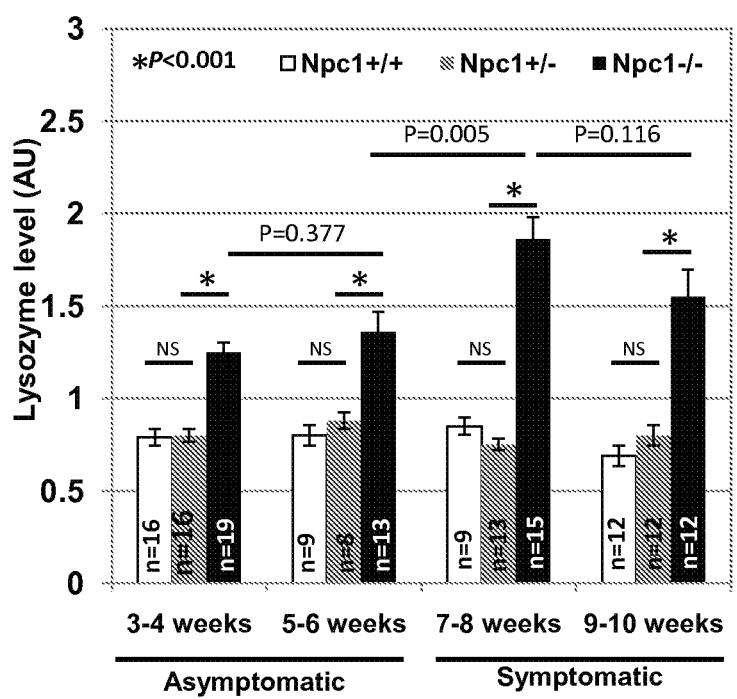
FIG. 4. Elevated lysozyme activity in plasma of Npc1$^{nih}$ Npc1$^{-/-}$ mice. Lysozyme activity in the plasma of Npc1$^{+/+}$, Npc1$^{+/-}$ and Npc1$^{-/-}$ mice was assessed using a commercially available fluorescence based lysozyme assay kit (see Materials and Methods). 'n' denotes the number of mice used per group. x-axis denotes the age of mice (in weeks) when the plasma lysozyme activity assay was performed. Error bars show the mean±SEM. 'NS' indicates not significant. Student's t test was carried out to determine the statistical significance.

As validation, we selected our top hit lysozyme, whose transcripts showed highest elevation in the brain, and also linear increase in the liver. Our interest was to determine a measure of lysozyme levels in the plasma. To facilitate rapid quantification, we pursued lysozyme's well defined muramidase activity assay in plasma. As shown in FIG. 4, levels of active lysozyme were indeed elevated in Npc1$^{-/-}$ mice 3-4 weeks old (representing 21-28 days at weaning and soon after) relative to age matched, Npc1$^{+/+}$ and Npc1$^{+/-}$. Further, plasma from Npc1$^{-/-}$ mice showed progressively increased lysozyme activity reaching a peak at 7-8 week of age. At 9-10 weeks (most animals die by 11 weeks in Npc1$^{nih}$ model), lysozyme activity levels plateau. This is in contrast to Lyz1 and Lyz2 transcript levels which increase steadily from 7-8 weeks to 9-10 weeks (See FIG. 3). Lysozyme is known to be inactivated at high concentrations and thus it is possible that activity levels do not accurately measure total protein at advanced stages. Nonetheless, it increased up to 8 weeks and in particular during transition from phenotypically asymptomatic (5-6 weeks) to symptomatic state (~7-8 weeks) [28,31]. The data shown in FIG. 4 are derived from both male and female animals, suggesting age dependent elevation of lysozyme was independent of gender. The assay could be carried out using 2 to 20 ul of plasma, suggesting it is sensitive and has a large dynamic range.

Elevation of Lysozyme in BALB/c Npc1$^{nmf164}$ Mice and its Reduction in Response to Treatment with Cyclodextrin, an Emerging Therapeutic Although the Npc1 null (Npc1$^{nih}$) mouse captures the progression of human disease, most patients show point mutations rather than a truncation in the gene. We therefore examined the BALB/c Npc1$^{nmf164}$ (Npc1$^{nmf}$) mouse with milder disease progression due to partial loss of NPC1 function as a result of a single point mutation (D1005G) in the cysteine rich domain of the protein, which is one of the most common regions for human mutations. Previous studies suggest that Npc1$^{nmf}$ in the C57BL/6J background have a life span of ~112 days and develop progressive disease [30]. They show delayed weight loss starting from 9-10 weeks and the rate was slower than the Npc1$^{nih}$ mice. Histological analyses of brain, liver and spleen showed abnormal cholesterol accumulation, and purkinje cell loss at a slower rate than the Npc1$^{nih}$ [30]. We found that BALB/c Npc1$^{nmf}$ have a similar life span (~120-125 days) and disease progression to that of C57BL/6J Npc1$^{nmf164}$ mice. Typically they exhibited weight loss from 12 weeks and by the end of 16 weeks ~15-20% weight loss was observed (FIG. 5A).

Figure 5:
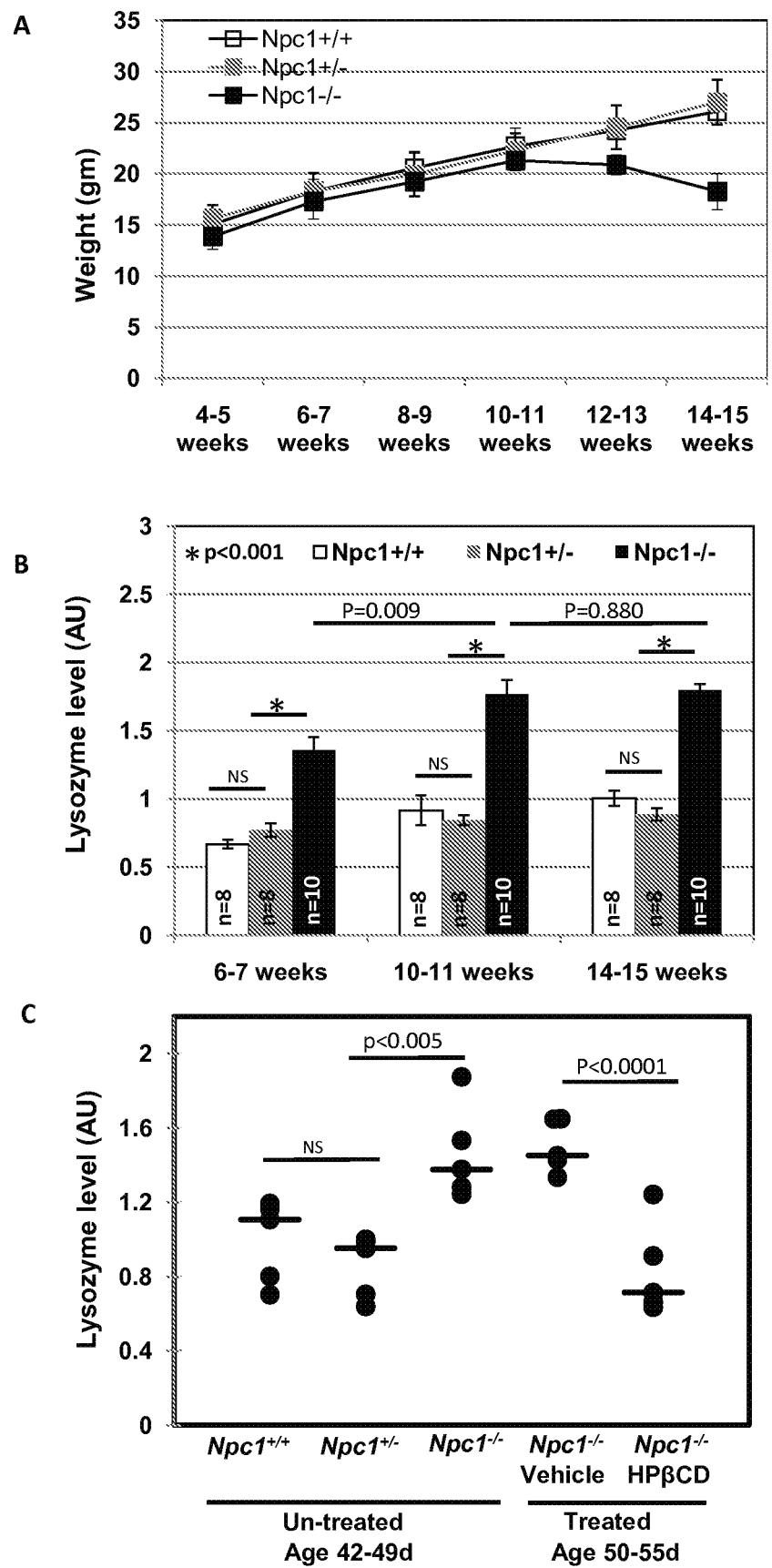
FIG. 5. Age-dependent weight loss and plasma lysozyme activity in Npc1$^{nmf164}$ mice. (A) Weight curves obtained for female animals of the following genotypes. Npc1$^{nmf164}$ WT, Npc1$^{+/+}$ (n=5); Npc1$^{nmf164}$ heterozygotes, Npc1$^{+/-}$ (n=9); Npc1$^{nmf164}$ homozygotes, Npc1$^{-/-}$ mice (n=5). Homozygote mutant mice started to lose weight from week 12: typically, they survive 17-18 weeks. Mean values±SD are shown. (B) Lysozyme activity in the plasma of Npc1$^{nmf164}$ WT, Npc1$^{+/+}$; Npc1$^{nmf164}$ heterozygotes, Npc1$^{+/-}$; Npc1$^{nmf164}$ homozygotes, Npc1$^{-/-}$. 'n' denotes the number of mice used per group. Error bars show the mean±SD. 'NS' indicates not significant (C) Scatter plot of the plasma lysozyme activity of untreated Npc1$^{nmf164}$ (age 42-49 days) and HPβCD or vehicle treated female mice (age 50-55 days). Median values are indicated by horizontal bars. 'NS' indicates not significant. Statistical significance was determined using Student's t test.

As shown in FIG. 5B, levels of active lysozyme were indeed elevated in Npc1$^{nmf}$ mice 3-4 weeks old (representing 21-28 days, the time of weaning and soon after) relative to age matched, controls. Further, plasma from Npc1$^{nmf}$ mice also showed progressively increased lysozyme activity reaching a peak at 10-11 weeks of age. At 14-15 weeks lysozyme levels plateau (and it is possible that here again, lysozyme is inactivated at high concentration). Most animals die by 17-18 weeks in this model. The data shown in FIG. 5B is derived from both male and female animals, suggesting that elevation in lysozyme may be a useful correlate for disease, especially at the early phases, when diagnosis is difficult but needed.

With the emergence of new therapeutics for NPC, there is urgent need for correlates whose levels mirror improvement of disease course as a consequence of treatment. Cyclodextrin has emerged as the most effective compound at retarding NPC disease in mice [46]. Previous studies suggest that weekly injections of HPβCD (2-hydroxypropyl-beta-cyclodextrin) to Npc1$^{nih}$ (a BALB/c strain) ameliorates the disease and extend the survival [47,48]. Similarly, weekly injections of HPβCD to Npc1$^{pf/pf}$ mice (a knock-in BALB/c strain carrying point mutations resulting in failure to cholesterol binding and manifestation of NPC disease) also show improvement in disease status [49]. We therefore treated Npc1$^{-/-}$ mice with HPβCD or vehicle control (0.2% DMSO in 0.9% saline) with once a week drug injections starting at age 21-27 days. At 50-55 days, untreated Npc1$^{-/-}$ mice had ~1.4-1.8 fold higher plasma lysozyme activity compared to Npc1$^{+/+}$ or Npc1$^{+/-}$ (age 42-49 days). The plasma lysozyme activity of the vehicle treated Npc1$^{-/-}$ mice remained elevated (comparable to untreated Npc1$^{-/-}$). However, it was significantly reduced in Npc1$^{-/-}$ mice treated with HPβCD (FIG. 5C). Thus, lysozyme may be an early disease correlate that measures responsiveness to a drug during the asymptomatic stage.

Figure 6:
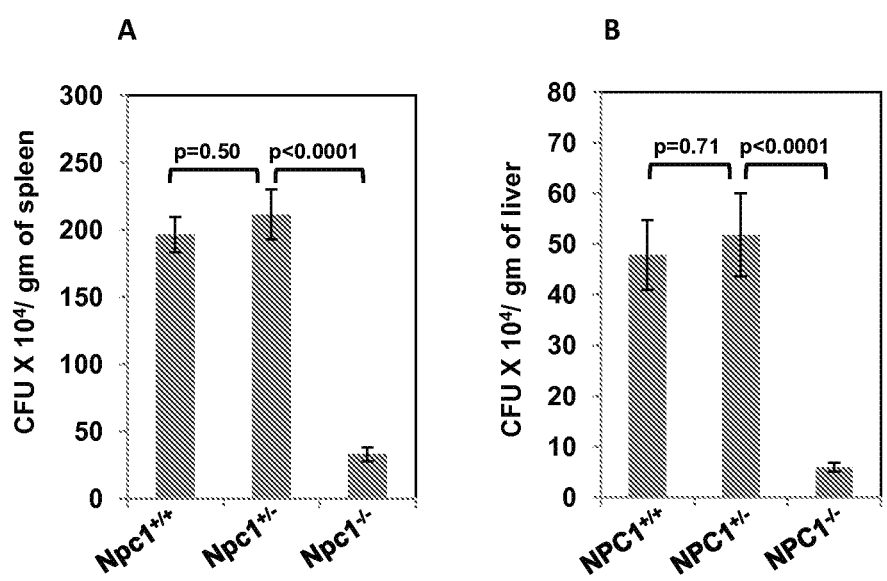
FIG. 6 Attenuated proliferation of *S. typhimurium* in (A) spleen and (B) liver of Npc1$^{-/-}$ mice. Npc1$^{+/+}$, Npc1$^{-/-}$ and Npc1$^{-/-}$, mice (age 6-8 weeks) were infected with *S. typhimurium* (1×10$^4$ CFU) by i.p injection. At 48 hpi, mice were sacrificed, organs isolated and bacterial CFU were determined. The data obtained from 3 independent experiments are shown. n=10 for Npc1$^{+/+}$ and Npc1$^{-/-}$ and n=8 for Npc1$^{+/-}$. Error bar show the mean±SEM. Student's t test was carried out to determine the statistical significance.

Functional Validation of Elevated Innate Immunity Genes in Liver and Spleen of Npc1$^{-/-}$ Mice Microbial systems provide rapid mechanisms of functional validation of innate immunity and there is prior evidence that defect in NPC1 results in attenuated intracellular infection by HIV-1 and *Brucella abortus* [17,18]. We therefore infected mice with the Gram-negative bacterium *S. typhimurium* which can be used as model organism to understand the cellular response underlying innate immunity We selected mice of age at 6-8 weeks, because this was approximately in the middle of the age range of animals examined in our microarray studies. Since we wanted to directly assess bacterial proliferation in the spleen and liver (and bypass the gut) the animals were infected through intraperitoneal (i.p) route. The bacterial load in spleen and liver was determined at 48 hours post infection (hpi) by measuring colony forming units. As shown in FIG. 6 A-B, for both liver and spleen, we found comparable bacterial loads in Npc1$^{+/+}$ and Npc1$^{+/-}$ mice. However, there was ~8-10 fold reduction in bacterial load in the organs of Npc1$^{-/-}$ mice.

Figure 11:
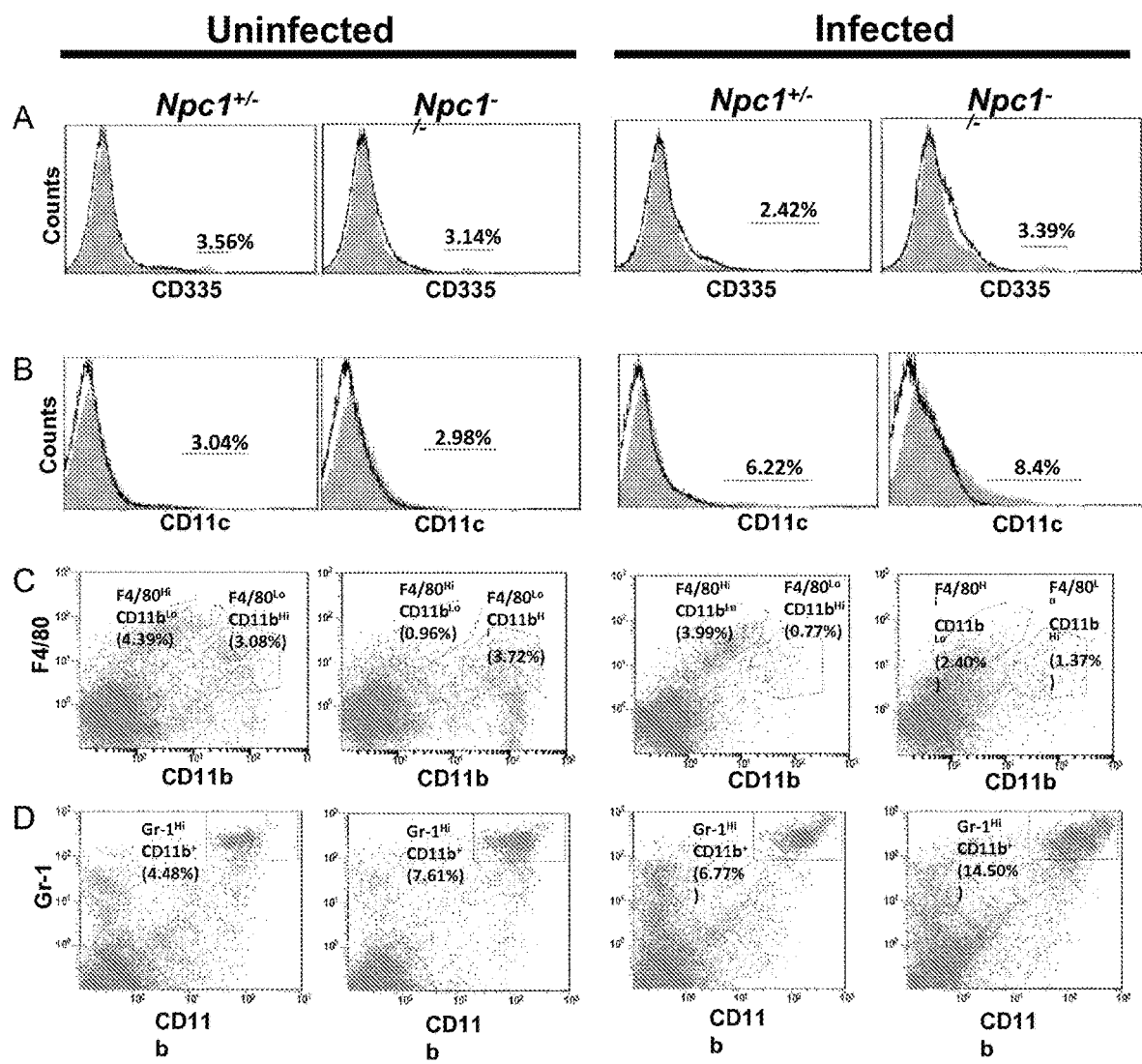
FIG. 11. Flow cytometric enumeration of different innate immune cells in spleen. Representative data showing the staining of splenocytes with different cell surface markers. Splenocytes from un-infected (left panel) and infected (right panel) with *S. typhimurium* at 48 hpi from Npc1$^{+/-}$ and Npc1$^{-/-}$ female litter mate mice (age 6-8 weeks) were isolated and stained with fluorophore conjugated antibodies, anti-CD335 for NK cells (panel A), anti-CD11c for dendritic cells (panel B), anti-F4/80 and CD11b for monocytes and macrophages (panel C) and anti-Gr-1 and CD11b for neutrophils (panel D). Monocytes and macrophages are represented into two sub groups, (i) F4/80$^{hi}$CD11b$^{lo}$ and (ii) F4/80$^{lo}$ CD11b$^{hi}$ whereas cells positive for CD11b and have high expression of Gr-1 (Gr-1$^{hi}$CD11b) were considered neutrophils. Open histograms represent the staining with isotype control and gray histograms represent the staining by specific antibodies as mentioned.

Since the spleen is readily amenable to comprehensive cellular analysis of innate immunity, we examined the numbers of CD335$^+$ natural killer (NK) cell, CD11c$^+$ dendritic cells (DC), CD11b$^+$F4/80$^+$ monocytes and macrophages (Mo/MO), and CD11b$^+$Gr-1$^{hi}$ neutrophils in splenic single cell suspensions of Npc1$^{-/-}$ and Npc1$^{+/-}$ animals (FIG. 7A and FIG. 11). Again, we selected mice of age at 6-8 weeks, because the reason described above. Flow cytometric analysis showed no effect on counts of NK cell or dendritic cells. Further, while the total number of CD11b$^+$F4/80$^+$ Mo/MO was unaffected (~57×10$^5$ in Npc1$^{+/-}$ versus ~53× 10$^5$ in Npc1$^{-/-}$), Npc1$^{-/-}$ animals showed decreased CD11b$^{lo}$ F4/80$^{hi}$ Mo/MO as compared to Npc1$^{+/-}$ controls, ~12×10$^5$ versus ~32×10$^5$, respectively, p<0.0005 and increased numbers of CD11b$^{hi}$F4/80$^{lo}$ Mo/MO as compared to Npc1$^{+/-}$ controls, ~41×10$^5$ versus ~25×10$^5$, respectively, p<0.001. Importantly, CD11b$^+$Gr-1$^{hi}$ neutrophils were significantly increased in Npc1$^{-/-}$ animals compared to Npc1$^{+/-}$, ~90×10$^5$ versus ~34×10$^5$, respectively, p<0.0005 (FIG. 7A and FIG. 11).

To test whether increased levels of neutrophils seen in FIG. 7A were functional in Npc1$^{-/-}$ spleens, we undertook cellular analyses of splenic cells after infection with *S. typhimurium* infection. As shown in FIG. 7B, the levels of NK cells were unchanged, CD11b$^{lo}$ F4/80$^{hi}$ Mo/MO decreased and CD11c$^+$ dendritic cells increased to the some extent in Npc1$^{-/-}$ versus Npc1$^{+/-}$ mice (FIG. 7B and FIG. 11). Importantly, CD11b$^+$Gr-1$^{hi}$ neutrophils were greatly increased in Npc1$^{-/-}$ compared to Npc1$^{+/-}$, ~167×10$^5$ versus ~74×10$^5$, respectively p<0.000001. The reduced bacterial proliferation seen in Npc1$^{-/-}$ spleen is well explained by the fact that as much as ~14% cells were neutrophils compared to only ~7% in Npc1$^{+/-}$ Together these data suggest an increased innate immunity function associated with neutrophils in the Npc1$^{-/-}$ spleen.

Figure 8C:
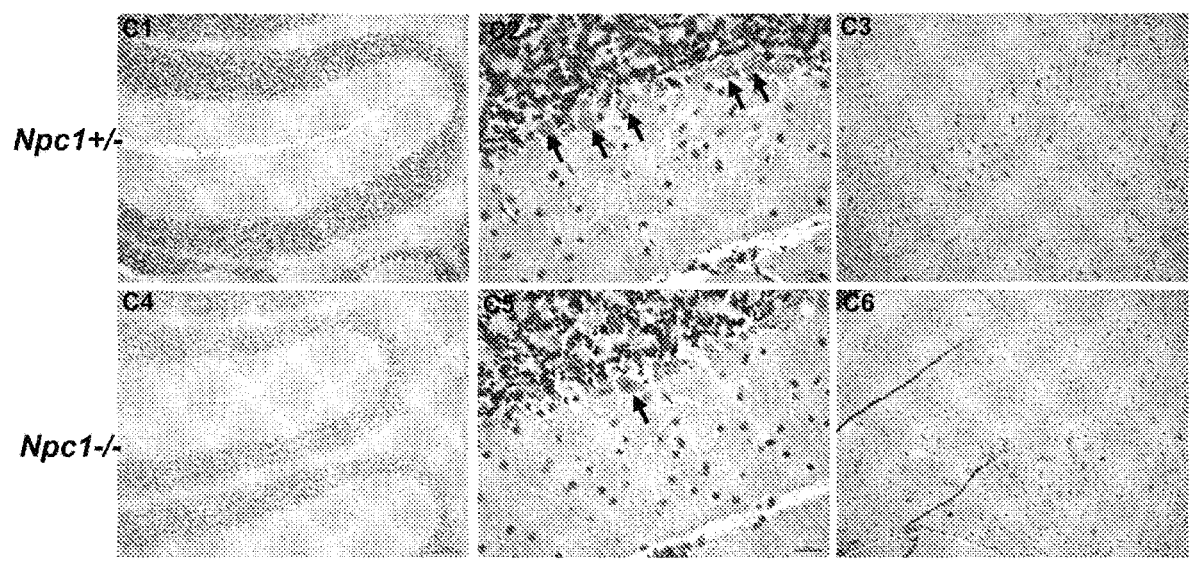
FIG. 8. Immunohistochemical analyses of spleen, liver and brain sections. (A) Immunohistochemical analyses reveal increased accumulation of neutrophils in the spleen of Npc1$^{-/-}$ mouse. Formalin-fixed paraffin embedded spleen sections (3-4 μm) of Npc1$^{-/-}$ and Npc1$^{+/-}$ mice (age 48-52 days) were stained with anti-Gr-1 antibodies to visualize neutrophils (cells stained in brown) which were primarily observed in the marginal zone, and in the red pulp of the spleen. Prominent accumulation of neutrophils was seen in the red pulp of Npc1$^{-/-}$ mouse (A3-4) compared to Npc1$^{+/-}$ mouse (A1-2). A2 and A4 are magnified view of area shown by dotted box in A1 and A3 respectively. M, megacaryocyte; T, trabecula. Original magnifications, ×400 (A1 &A3) and ×1000 (A2&A4). (B) Detection of giant foci of neutrophils (cells stained in brown) in the liver of Npc1$^{-/-}$ mouse age 48-52 days (B3-4). These large foci of neutrophils were not detected in the liver of age-matched Npc1$^{+/-}$ mouse (B1-2). Immunohistochemical staining on formalin-fixed paraffin embedded liver sections (3-4 μm) were carried out using anti-Gr-1 antibodies to visualize neutrophils. Tissue damage is clearly evident (B3-4) in the area of neutrophils accumulation in Npc1$^{-/-}$ mouse. B2 and B4 are magnified views of areas shown by dotted boxes in B1 and B3 respectively. Original magnifications, ×400 (B1&B3) and ×1000 (B2&B4). (C) Immunohistochemical staining of formalin-fixed paraffin embedded brain sections of Npc1$^{-/-}$ and Npc1$^{+/-}$ mice (age 48-52 days) was performed using anti-Gr-1 antibodies. The entire brain (sagittal sections) was scanned. Panels are; C1 and C4, cerebellum of Npc1$^{+/-}$ and Npc1$^{-/-}$ mouse respectively; C2 and C5, magnified view of cerebellum of Npc1$^{+/-}$ and Npc1$^{-/-}$ mouse respectively; C3 and C6, magnified view of regions from mid brain of Npc1$^{+/-}$ and Npc1$^{-/-}$ mouse respectively. Several purkinje cells are evident (shown by black arrows) in Npc1$^{+/-}$ (C2), however in Npc1$^{-/-}$ (C5) only few are seen. Original magnifications, ×100 (C1, C3, C4 & C6) and ×400 (C2&C5).

The increase in neutrophils is consistent with the innate immune cell footprint observed in microarray. As an additional follow up, we functionally validated neutrophils accumulation by immunohistochemistry (IHC), using spleen from Npc1$^{-/-}$ and Npc1$^{+/-}$ littermates aged 48-52 days, which is an intermediate time point in the life span. Neutrophils (Gr-1$^+$ cells stained in brown) were primarily observed in the marginal zone and in the red pulp of the spleen in both Npc1$^{+/-}$ and Npc1$^{-/-}$ mice (FIG. 8A). However, a massive accumulation of neutrophils was seen in the red pulp of Npc1$^{-/-}$ mouse (FIG. 8A, panel A3-4) compared to Npc1$^{+/-}$ mouse (FIG. 8A, panel A1-2). Since *S. typhimurium* showed attenuated growth in liver, we examined whether neutrophils were also elevated in the liver. Prior data in the literature have suggested accumulation of foamy macrophages in liver but neutrophils have not been investigated [2,3,8]. As shown in FIG. 8B, (panel B3-4), giant foci of neutrophils (Gr-1$^+$ cells stained in brown) were seen in the liver of Npc1$^{-/-}$ mouse, compared to the liver of Npc1$^{+/-}$ mouse (FIG. 8B, panel B1-2). Notably, damage to liver tissue in the region of neutrophil accumulation was seen in Npc1$^{-/-}$ mice. In summary the data support that neutrophils infiltrate spleen and liver of Npc1$^{-/-}$ mice.

Immunohistochemical staining failed to show accumulation of neutrophils in the brain (FIG. 8 C). Thus, anti microbial lysosomal secretory protein transcripts (such as lysozymes, cathepsins etc) elevated in the brain come from other cellular sources. Although we did not determine the exact source of over expression of lysozyme and other markers, a likely source in brain may be microglia and/or astrocytes that have been shown to be activated in brain [9]. Since lysozyme and other secretory lysosomal proteins are expressed in variety of cells, additional sources cannot be ruled out. Lysozyme and other lysosomal proteins particularly in plasma could be derived from neutrophils which are known to store high proportion of these proteins in the secretory granules which are specialized lysosomes [50,51]. Elevation of neutrophils in the liver and spleen of NPC mice strengthens this hypothesis. Autopsies are rarely undertaken in humans to analyze diseased organs (since the cause of death is known to be due to NPC) and thus the involvement of neutrophils in spleen and liver in human disease have not been addressed. However, standard blood work up is carried out in patients and does not reveal notable cellular hematological abnormalities. Our analysis of mouse blood likewise revealed that cellular parameters in both $Npc1^{-/-}$ and $Npc1^{+/-}$ mice remained in the normal range (Table 5). Notably, there was no significant change in either circulating neutrophils or macrophages in the blood (Table 5).

Discussion

The examination of transcriptional changes seen from freshly weaned animals to late in neurodegeneration, in three major organ systems, enabled prediction of innate immunity trends that could not be obtained from single or a few time points in each organ. Our data reveal that in the brain, a restricted set of innate immune processes are activated early in this organ, exacerbated with age and are the dominant conserved response through the animal's life span. Prior analysis of individual time points reveal increase in innate immune transcripts in the brain, but a relatively large number of genes are changed at any given time point, which obscured discernment of conserved patterns detectable at all stages. Specifically, we see age-dependent elevation of lysosomal proteins in the brain, suggesting elevation of these proteins, possibly in a systemic way in many different cell types. The most likely reason is that NPC1 is a lysosomal protein and thus its systemic loss induces a compensatory response in other lysosomal components in all cells. Consistently, over expression of Cathepsin D (CTSD) has been reported in the brain of murine models of several other lysosomal diseases such as Gaucher's disease, Sandhoff disease, GM1 gangliosidoses, Neimann-Pick A [52]. Elevated Ctsb transcripts have also been observed in the brain of Sandhoff and Tay-Sachs patients [53]. In addition to innate immune markers, we also see elevation of transcripts of alpha-N-acetylglucosaminidase (Naglu) and HexosaminidaseB (Hexb), genes linked to lysosomal diseases MPS IIIB and Sandhoff disease respectively.

Our data also reveal that over expression of lysosomal, innate immune proteins in the brain is conserved in liver and spleen of NPC. Conservation in secretory, soluble, lysosomal proteins shared between brain and liver enabled prioritization of candidate proteins that correlate to cerebral disease and are likely to be detected in plasma. Our work here validated the top hit lysozyme. Recent studies [54] suggest that LGALS3 and CTSD may be suitable disease markers in patient plasma. These markers were selected on the basis of transcriptional expression in the $Npc1^{-/-}$ liver alone in absence of data from brain. This study originally prioritized Lgals3 (highly up regulated) Plau (moderately up regulated) and Ctsd (mildly up regulated). However, only LGALS3 and CTSD were validated in patient plasma. Plau is absent in our list, however both Lgals3 and Ctsd are included (Table 4). Based on our data of transcript elevation in the brain, Ctsd is likely a better index of neurological disease, because it is moderately up regulated in both the brain and the liver. In contrast Lgals3 may be a preferred marker for liver disease since we find that it is not substantially up regulated in the brain. Cluzeau et al., 2012 [54] demonstrated that Lgals3 and Ctsd transcripts reduced in response to HUCD in $Npc1^{-/-}$ mice. We show that lysozyme levels decrease in plasma in response to HUCD in mice carrying a point mutation in NPC1. Together, these data strongly validate our predictions of lysosomal, secretory innate immune proteins alone or in combination, may provide useful surrogate disease markers for NPC in plasma. As indicated earlier, many are also up regulated in other lysosomal disorders, suggesting they may also developed as pan or specific plasma markers for neurological diseases associated with lysosomal storage and where diagnosis is a major problem.

To further validate our gene expression data we compared them to prior gene expression studies undertaken in NPC whole animals and/or cultured cells [5,13,14,15,28,36]. Since NPC is a lipid storage disease, we examined whether there were changes in genes related to metabolism of lipids and fatty acids. Indeed, 180 genes and 117 genes were respectively linked to lipid and fatty acid metabolism (Table S4). This is consistent with prior analysis of single time points analyzed from $Npc1^{-/-}$ mice [5,13,14]. In contrast, we found no major changes in Liver X receptor (LXR) pathways which regulate levels of cellular cholesterol [36] but consistent with prior reports that there is no significant activation of LXR genes [28,16,46] in NPC organs. As exception, Abcg1, Lpl and Pltp were slightly elevated (Table S2), but this was also noted by Cluzeau et al., 2012 [54]. Prior gene expression analyses in the brain by qPCR, revealed over expression of genes involved in extracellular cholesterol trafficking (Apod, Apoe), intracellular cholesterol trafficking (Lipa, Npc2), sterol synthesis and metabolism (Cyp7b1, Cyp11a1) and cell abundance (Gfap, Pcp4) [28]. Our data suggest that other than Npc2 and Gfap, none were consistently up regulated across the animal life span in the brain. However inflammatory genes such as Cd68, Itgax, Itgb2, C3ar1, Cd44, Cyba, Fcgr2b, Gm, Ptprc etc were consistently up regulated in NPC brain (Table S4). Genes related to calcium regulation (Camk1, Camta2) and oxidative stress (Cyba, Cybb, Jund, Ncf2, Ncf4) reported in cell culture studies [15] were also consistently up regulated in the liver of NPC mice (Table S2). Cluzeau et al., 2012 [54] reported age dependent expression of 18 genes in the liver. Our study confirms 14 out of 18 genes showing good correspondence between the two data sets in the liver. These genes correspond to pathways of lipid homeostasis (Abcg1, Hexa, Lpl), cell adhesion and extracellular remodeling (Itgax, Itgb2, Mmp12), immune response and inflammation (Ctss, Gpnmb, Lyz2), developmental signaling (Rragd), oxidative stress (Cyba, Cybb), synaptic plasticity (Syngr1) (Table S2).

Lysozyme is a small, stable protein present in blood as well as additional secretions like saliva and thus particularly suited to being developed as a simple disease test. Elevation of lysozyme in both $Npc1^{nih}$ and $Npc1^{nmf}$ mice strongly suggest that secretory lysosomal protein markers may be associated with both severe and milder disease progression as observed in patients. Additionally, plasma lysozyme levels provide a simple test to follow the effectiveness of a drug in mouse models of NPC. Curiously, although transcript levels of lysozyme continue to increase with age in both brain and liver, the enzymatic activity of lysozyme plateaus at later stages in both the $Npc1^{nih}$ and $Npc1^{nmf}$ models. One possibility is that as the disease becomes severe, lysozyme protein denatures and loses its activity due to prolonged oxidative stress [5], but this will require additional study. Nonetheless, at a minimum, lysozyme activity provides a useful marker in preclinical development of new therapeutics.

Our study also provide insights into activation of innate immune functions as well as comprehensive analysis of innate immune cells in the spleen of $Npc1^{-/-}$ mice, and thus established for the first time, that defect in NPC1 leads to increased infiltration of neutrophils in the spleen and liver.

Indeed, up regulation of genes coding for neutrophils-specific proteins such as NCF4 (neutrophil cytoplasmic factor 4, increased ~7 fold) in the liver along with its interacting proteins NCF2 (neutrophil cytoplasmic factor 2) and CYBA (cytochrome b-245, alpha polypeptide, also known as p22phox) predicted infiltration of neutrophils to liver. Neutrophils or polymorphonuclear lymphocytes (PMNLs) are essential innate immune cells, and the host's first line of defense against various bacterial and fungal infections. They are laden with various cytotoxic granules enriched with different powerful antimicrobial molecules such as cationic peptides, proteases, lactoferrin, myeloperoxidase etc [55,56]. They undergo respiratory burst and produce reactive oxygen intermediates to target microbial pathogens [55,57]. In addition to microbial killing, granule components also mediate cell to cell interaction, adhesion and extravasation. Elevated neutrophils in spleen, liver of $Npc1^{-/-}$ mice could be attributed due to increased chemoattraction and extravasation, without steady state elevation in blood. The over expression of matrix metalloproteases, galectins, integrins, phygocyte oxidases, adhesins etc in spleen and/or liver of $Npc1^{-/-}$ mice supports enhanced neutrophils migration to these organs.

Although, we did not carry out cellular analysis of liver, in addition to neutrophils, large 'foamy' macrophages were readily detected in sections through NPC liver (data not shown) and undoubtedly contribute to an inflammatory response, as has been previously reported [2,8]. Indeed recent studies suggest that removal of macrophages by Ccl3 deletion aggravates the NPC disease [14] suggesting macrophages may be protective in NPC. It should be noted that although neutrophils are required to resolve inflammation, their sustained activation, degranulation and release of cytotoxic molecules leads to tissue injury [58]. Indeed, neutrophil apoptosis followed by their phagocytosis by macrophages is an essential mechanism for regulating neutrophil functions and is an important control point in the development and resolution of inflammation [59,60]. Neutrophil numbers are not compromised in Ccl3 mutant mouse [61]. In the absence of macrophage function, the tissue would be exposed to cytotoxic molecules released from apoptotic neutrophils and may thereby aggravate the injury. Future studies directed towards understanding the neutrophils function in the Ccl3/Npc1 double knockout mouse may provide a better understanding of neutrophil and macrophage involvement in NPC disease. In addition whether neutrophils are elevated in human NPC spleen and liver needs to be investigated.

Future studies will also focus on determining whether lysozyme and other lysosomal/secretory proteins are disease markers in human NPC patients as well as other lysosomal disorders. One early report suggests a modest increase in plasma lysozyme in four adult patients with Gaucher's disease [62]. Elevated lysozyme transcripts and protein have been found in neuronal cells in the brain of another lysosomal disorder mouse model Sanfilippo syndrome type B (also known as MPS IIIB) [63,64]. A linkage between lysozyme and hyperphoshoylated tau has been suggested in the MPS IIIB mouse brain [64]. At high concentration, lysozyme on its own is known to be amyloidogenic [65] and exposure of cultured rat neurons to oligomers of hen egg white lysozyme had been found to induce hyperphosphorylation of tau [66]. Thus, in addition to serving as secretory markers, lysozyme and other secreted lysosomal proteins expressed in glial and neuronal (and possibly endothelial) cells in the brain, may also exacerbate neurological disease.

Materials and Methods

Materials

All fine chemicals and antibiotics were obtained from Sigma (St Louis, Mo., USA), unless otherwise indicated. Anti-mouse F4/80-FITC antibody (clone CI:A31) was from Abd Serotec (Raleigh, N.C., USA). Anti-mouse CD335-FITC (clone 29A1.4), CD11c-FITC (clone N418), CD11b-PE (clone M1/70), and Gr-1-APC (clone RB6-8C5) were from eBioscience (San Diego, Calif., USA). For IHC, unlabeled rat anti-mouse Gr-1 (clone RB6-8C5, eBioscience) was used to detect neutrophils. The secondary antibody was biotinylated rabbit anti-rat IgG (mouse absorbed, Vector Laboratories)

Production of $Npc1^{nih}$ and $Npc1^{nmf164}$ mutant mice $Npc1^{nih}$ was purchased from JAX labs. It is a widely used NPC BALB/c strain [67], carrying a truncation and premature translation of NPC1 protein and originally established by Peter Penchev at the National Institutes of Health (Bethesda, Md., USA). $Npc1^{nmf164}$ is a BALB/c strain derived from the recently described $Npc1^{nmf164}$ in C57BL/6J [30] which contains an ethyl-nitroso urea-induced point mutation in the Npc1 gene. The mutation is a single nucleotide change (A to G at cDNA bp 3163) resulting in an aspartate to glycine change at position 1005 (D1005G). The mutation was transferred from C57BL/6J to the BALB/c strain by Robert P. Erickson, University of Arizona Health Sciences Center, Tucson, Ariz., USA. Homozygous mutants of both strains ($Npc1^{-/-}$) along with wild type littermates ($Npc1^{+/+}$), were generated by crossing heterozygous mutant ($Npc1^{+/-}$) males and females, in-house. $Npc1^{nih}$ Mouse pups were genotyped according to published protocols [67] whereas $Npc1'^{864}$ mice were genotyped based on PCR followed by digestion with BstEII [30]. In this study, unless otherwise indicated, $Npc1^{nih}$ mice were used.

Microarrays and Expression Analyses

Brain from 11 $Npc1^{-/-}$ and 16 control female mice ($Npc1^{+/+}$ and $Npc1^{+/-}$) age ranging from 20-84 days (see FIG. 9A for details) and spleen and liver from 6 $Npc1^{-/-}$ and 6 $Npc1^{+/-}$ female mice age ranging from 20-71 days (see FIG. 9B for details) were surgically harvested, kept in RNA later and stored at −20° C. until used. RNA was isolated using Roche MagNa Pure Compact automated system and labeling was done using MessageAmp™ Premier RNA Amplification Kit (Invitrogen). Affymetrix mouse 430 2.0 array hybridizations were performed by 'UCLA Clinical Microarray Core', UCLA, Los Angeles, Calif., USA, following standard Affymetrix GeneChip Expression Analysis protocol. RNA from each animal was profiled individually. The acquisition of array image was undertaken by using Affymetrix GeneChip Command Console 1.1 (AGCC). Subsequent raw data were analyzed using DNA-Chip Analyzer (D-Chip) with the .CEL files obtained from AGCC. This analysis was undertaken irrespective of consideration of littermates. A PM/MM difference model was used for estimating gene expression levels and combined with a quantile approach for data normalization. Thresholds for selecting significant genes were set at a relative difference≥1.5-fold, absolute difference≥100 signal intensity units and $p<0.05$. Genes that met all three criteria were considered as significantly changed. All data are available from NCBI, GEO accession number GSE39621.

Identification of Secretory Proteins that Show Age-Dependent, Over-Expression in Brain and Liver Genes up regulated in the brain of $Npc1^{-/-}$ mice across all time points, were further selected for secretory proteins identified by an N-terminus signal sequence, recognized by SignalP 4.0 (www.cbs.dtu.dk/services/SignalP/) The Uni- Prot database (www.uniprot.org/) was also utilized to confirm the presence of a signal sequence and identify additional secretory proteins that lack conventional signal sequences. Proteins known to localize to membranes or predicted to have transmembrane domains as predicted by the UniProt database were filtered out. The resulting short list from the brain was cross referenced with genes over expressed in liver at all time points to yield 18 genes. For each of these genes, the mean signal intensities detected for age matched $Npc1^{+/-}$ (control) mice on the microarray chip was subtracted from that seen with $Npc1^{-/-}$ mice. This yielded 12 genes with progressive age-dependent increase at three distinct time points across the animal's life span in both brain and liver.

In Vivo Infection of Mice

*Salmonella enterica* serovar *Typhimurium* SL1344 was grown in Luria-Bertani (LB) broth containing streptomycin sulfate (50 µg/ml). Female $Npc1^{+/+}$, $Npc1^{+/-}$ and $Npc1^{-/-}$ mice (age 6-8 weeks) were used for the *S. typhimurium* infection. Bacteria from overnight cultures were pelleted by centrifugation for 5 min at 6000 rpm and were re-suspended in PBS. Mice were given $1 \times 10^4$ bacteria in 100 µl by i.p injection. Serial dilutions of inoculants were plated on selective media to determine the actual doses. At 48 hours post infection (hpi), mice were sacrificed. Spleen and liver were isolated, weighed, homogenized, serial dilutions were made and plated on selective media to determine the number of bacterial colony forming units (CFU).

Flow Cytometry

The number and types of different immune cells in spleen of female $Npc1^{+/-}$ and $Npc1^{-/-}$ littermates (6-8 weeks) were enumerated as follows. Spleens were harvested, splenocytes were prepared and cells were counted using a hemocytometer. *S. typhimurium* infection of mice was performed as described earlier and splenocytes were isolated 48 hpi. For flow cytometry, cells were stained with fluorophore conjugated antibodies to CD335 (FITC; for NK cells), CD11c (FITC; for dendritic cells), F4/80 (FITC; for macrophages) CD11b and Gr-1 (PE and APC respectively, for neutrophils). Cells positive for both F4/80 and CD11b were considered monocytes/macrophages whereas cells positive for CD11b and high Gr-1 expression were considered neutrophils. Depending on the requirements and fluorophore compatibility splenocytes were stained either separately or in combinations. Suitable isotype control for each antibody was included as controls and compensation was performed wherever required. $10^5$ events were typically recorded in Beckman Coulter FC500 flow cytometer.

Organ Harvest and Immunohistochemistry

Female, littermates, $Npc1^{+/-}$ and $Npc1^{-/-}$ mice (age 48-52 days) were sacrificed by asphyxiation using $CO_2$ The circulatory bed was washed with PBS (pH 7.4), and subsequently perfused with 10% neutral buffered formalin (~4% formaldehyde). The organs (brain, liver, lung and spleen) were surgically harvested and stored in 4% formaldehyde at room temperature (RT) until transfer to paraffin. Formalin paraffin-embedded tissue sections (3-4 µm) were dewaxed in xylene and alcohol. Antigen retrieval was done by pre-incubation of deparaffinized samples with 0.05% proteinase K (Dako, Germany) in 50 mM Tris-HCl (pH 7.5) for 8 min at RT. After washing, the sections were immersed in 3% $H_2O_2$ in distilled water for 20 min at RT to block endogenous peroxidase. After an additional wash with PBS, the sections were treated with 5% rabbit serum for 30 min, followed by successive incubation in avidin and biotin (Avidin/biotin blocking kit, Vector Laboratories) to block endogenous biotin. Anti-mouse Gr-1 (5 µg/ml in PBS with 2% rabbit serum) was applied to the sections for 60 min at RT. Secondary antibodies were biotinylated rabbit anti-rat IgG (mouse absorbed, Vector Laboratories). Reagents were prepared according to the manufacturer's instructions. The peroxidase complexes were revealed by incubation with 3,3'-diaminobenzidine-tetra-hydrochloride (DAB, Vector Laboratories) and the sections were lightly counterstained with Mayer's hemalum. The slides were then mounted in cytoseal XYL (Thermo Scientific, Kalamazoo, USA). Sections stained only with secondary antibodies served as controls. Pictures were acquired on a Nikon Olympus microscope, using a Nikon digital DS-Fi1-U2 camera controlled by NIS-Elements F3.0 Nikon software (all from Nikon Instruments INC, Tokyo, Japan). Images were visualized with A10 PL 10×/0.25, or a DPlan Apo 40×/1.00 oil-immersion or a DPlan Apo 100×/1.30 oil-immersion objective lens (Nikon).

Lysozyme Activity Assay in Mouse Plasma

Lysozyme activity in the plasma of $Npc1^{+/+}$, $Npc1^{+/-}$ and $Npc1^{-/-}$ mice was measured using fluorescence based lysozyme assay kit (EnzCheck, Molecular Probes, Grand Island, N.Y., USA). The assay measures the lysozyme activity on *Micrococcus lysodeikticus* cell walls, which are labeled to such a degree that the fluorescence is quenched. Lysozyme action relieves this quenching; yielding an increase in fluorescence that is proportional to lysozyme activity. Plasma from both female and male $Npc1^{nih}$ mice corresponding to 50-500 µg protein (~2 to 10 µl in volume) was used in a 100 µl reaction volume. The reaction was carried out either at 37° C. for 1 h (when 500 µg plasma protein was used) or at 37° C. for 24 h (when 50 µg plasma protein was used). For $Npc1^{nmf164}$ mice, we used 50 µg plasma protein and the reaction mixture was incubated at 37° C. for 24 h. Fluorescence was read using excitation/emission of 494/518 nm in a multiwall plate reader spectramax M2 (Molecular devices, CA, USA). The values obtained were normalized to 1 by dividing the numbers by the maximum value of lysozyme obtained among $Npc1^{+/-}$ mice. Purified chicken egg white lysozyme was used as a positive control.

Drug Injections and Blood Withdrawal

Starting at P21-27 and once a week thereafter, $Npc1^{nmf164}$ homozygous mutant female mice were injected i.p with 20% 2-hydroxypropyl-beta-cyclodextrin (HPβCD, 4000 mg/Kg) prepared in 0.2% DMSO and 0.9% saline. Control mice received 0.2% DMSO in 0.9% saline. Blood via cheek bleed was collected from mice, age 50-55 days from both treatment groups in EDTA tubes (BD, CA). Plasma was separated by centrifugation at 2500 rpm for 15 min and stored at −70° C. until used. For hematology analyses, 20 µl blood was collected in a microfuge tube coated and dried with 20 µl of 1.25 mg/ml EDTA. Blood cell parameters were analyzed by Hemavet 950 (Drew Scientific, Dallas).

Miscellaneous

All animal experiments were performed with the approval and authorization from the 'Institutional Review Board' and the 'Animal Care and Use Committee', University of Notre Dame. Student's t test was carried out to determine the statistical significance of the data. $p \leq 0.05$ considered significant.

Supplemental Tables

Table S1.

List of differentially expressed genes in the brain across the life span (20-84 days) of $Npc1^{-/-}$ mice. Up regulated innate immunity genes listed in InnateDB are shown in bold letters.

Table S2.

List of differentially expressed genes in the liver across three age group (20-71 days) of Npc1$^{-/-}$ mice. Up regulated innate immunity genes listed in InnateDB are shown in bold letters.

Table S3.

List of differentially expressed genes in the spleen across three age groups (20-71 days) of Npc1$^{-/-}$ mice. Up regulated innate immunity genes listed in InnateDB are shown in bold letters.

Table S4.

Enrichment of top 10 biofunctions pathways and their associated genes in brain, liver and spleen of Npc1$^{-/-}$ mice Table S5.

List of 18 secretory genes up regulated in brain and liver of Npc1$^{-/-}$ mice.

TABLE 1

Top 20 up regulated genes in brain of Npc1$^{-/-}$ mice across the life span (20-84 days)

| Genes | Fold up regulation |
|---|---|
| Lyz1: lysozyme 1 | 12.2 |
| Clec7a: C-type lectin domain family 7,membera | 11.16 |
| Gm11428: predicted gene 11428 | 10.32 |
| Lyz2: lysozyme 2 | 9.62 |
| Gp49a: glycoprotein 49 A | 8.44 |
| Itgax: integrin alpha X | 7.09 |
| Mpeg1: macrophage expressed gene 1 | 5.93 |
| Cd84: CD84 antigen | 5.87 |
| Gpnmb: glycoprotein (transmembrane) nmb | 5.34 |
| H19: H19 fetal liver mRNA | 4.9 |
| Fcgr2b: Fc receptor, IgG, low affinity IIb | 4.38 |
| Ms4a7: membrane-spanning 4-domains, subfamily A, member 7 | 4.32 |
| Tnfaip2: tumor necrosis factor, alpha-induced protein 2 | 4.32 |
| Cd68: CD68 antigen | 4.26 |
| Ifit1: interferon-induced protein with tetratricopeptide repeats 1 | 4.25 |
| Gfap: glial fibrillary acidic protein | 4.14 |
| C4b: complement component 4B (Childo blood group) | 4.14 |
| C3ar1: complement component 3a receptor 1 | 3.99 |
| Usp18: similar to ubiquitin specific protease UBP43 | 3.91 |
| Trem2: triggering receptor expressed on myeloidcells2 | 3.88 |

Genes marked in bold are related to innate immunity and the genes marked in bold and also underlined are innate immunity genes catalogued by InnateDB.

TABLE 2

Top 20 up regulated genes in liver of Npc1$^{-/-}$ mice across three age groups (20-71 days)

| Genes | Fold up regulation |
|---|---|
| Mmp12: matrix metallopeptidase 12 | 80.37 |
| Il7r: interleukin 7 receptor | 55.29 |
| Gpnmb: glycoprotein (transmembrane) nmb | 48.32 |
| Pou3f1/Oct-6 | 39.5 |
| Lgals3: lectin, galactose binding, soluble3 | 36.39 |
| Egr2: early growth response 2 | 25.78 |
| Capg: capping protein (actin filament), gelsolin-like | 25.69 |
| Clec4d: C-type lectin domain family 4,memberd | 25.15 |
| Nupr1: nuclear protein 1 | 23.94 |
| Gpr137b: G protein-coupled receptor 137B | 23.23 |
| Klra3/9: killer cell lectin-like receptor, subfamily A, member 3/9 | 22.81 |
| Clec7a: C-type lectin domain family 7,membera | 21.49 |
| Camp: cathelicidin antimicrobial peptide* | 21.32 |
| Mm.138637.1 | 20.92 |
| Slamf7: SLAM family member7 | 19.18 |
| Mm.201472.1 | 17.34 |
| Speg: SPEG complex locus | 16.02 |
| Bcl2a1a/b/d: B-cell leukemia/lymphoma 2 related protein A1a/b/d | 15.61 |
| Odz4: odd Oz/ten-m homolog 4 (*Drosophila*) | 15.51 |
| Ms4a7: membrane-spanning 4-domains, subfamily A, member 7 | 15.08 |

Genes marked in bold are related to innate immunity and the genes marked in bold and also underlined are innate immunity genes catalogued by InnateDB.

TABLE 3

Top 20 up regulated genes in spleen of Npc1$^{-/-}$ mice across three age groups (20-71 days)

| | regulation |
|---|---|
| Atp6v0d2: ATPase, H+ transporting, lysosomal V0 subunit D2 | 58.08 |
| Gpnmb: glycoprotein (transmembrane) nmb | 19.98 |
| Hal: histidine ammonia lyase | 10.06 |
| Clec7a: C-type lectin domain family 7,membera | 9.7 |
| Gm11428: predicted gene 11428 | 8.84 |
| Trim29: tripartite motif-containing 29 | 8.65 |
| Atf3: activating transcription factor3 | 8.37 |
| Mmp12: matrix metallopeptidase 12 | 8.24 |
| Ahnak2: AHNAK nucleoprotein 2 | 7.64 |
| Dnahc2: dynein, axonemal, heavy chain 2 | 7.55 |
| Cdkn1c: cyclin-dependent kinase inhibitor 1C (P57) | 6.84 |
| Mm.138637.1 | 6.23 |
| Ms4a7: membrane-spanning 4-domains, subfamily A, member 7 | 6.21 |
| Fabp5: fatty acid binding protein 5 | 6.1 |
| 9430019H13Rik: RIKEN cDNA 9430019H13 gene | 5.88 |
| Msr1: macrophage scavenger receptor1 | 5.86 |
| Anpep: alanyl (membrane) aminopeptidase | 5.05 |
| Elane: elastase, neutrophil expressed | 4.68 |
| F10: coagulation factor X | 4.56 |
| Ms4a3: membrane-spanning 4-domains, subfamily A, member 3 | 4.52 |

Genes marked in bold are related to innate immunity and the genes marked in bold and also underlined are innate immunity genes catalogued by InnateDB.

TABLE 4

List of 12 potential biomarker genes

| Genes | Entrez Gene ID | Fold up regulation in brain | Fold up regulation in liver |
|---|---|---|---|
| Lyz1: lysozyme 1 | 17110 | 12.2 | 6.4 |
| Lyz2: lysozyme 2 | 17105 | 9.62 | 6.91 |
| C1qb: complement component 1q, beta polypeptide | 12260 | 3.7 | 2.2 |
| Lgals3: Lectin, galactose binding, soluble3 | 16854 | 3.38 | 36.39 |
| C1qa: complement component 1q, alpha polypeptide | 12259 | 2.72 | 1.61 |
| Grn: granulin | 14824 | 2.26 | 1.58 |
| Ctss: cathepsin S | 13040 | 1.95 | 4.97 |
| Ctsd: cathepsin D | 13033 | 1.86 | 2.43 |
| Timp2: tissue inhibitor of metalloproteinase 2 | 21858 | 1.85 | 3.94 |

TABLE 4-continued

List of 12 potential biomarker genes

| Genes | Entrez Gene ID | Fold up regulation in brain | Fold up regulation in liver |
|---|---|---|---|
| Man2b1: mannosidase 2, alpha B1 | 17159 | 1.71 | 1.51 |
| Hexb: hexosaminidase B | 15212 | 1.62 | 2.58 |
| Ctsb: cathepsin B | 13030 | 1.54 | 4.06 |

Genes marked in bold code for secretory lysosomal proteins

TABLE 5

Blood cell parameters and hematological analyses in Npc1$^{-/-}$ mice

|  | Normal Range | Npc1$^{+/-}$ | Npc1$^{-/-}$ |
|---|---|---|---|
| Leukocytes |  |  |  |
| WBC (K/µl) | 1.8-10.7 | 8.3 ± 0.80 | 8.43 ± 1.39 |
| NE (K/µl) | 0.1-2.4 | 1.18 ± 0.16 | 1.53 ± 0.54 |
| LY (K/µl) | 0.9-9.3 | 6.82 ± 0.67 | 6.515 ± 0.93 |
| MO (K/µl) | 0.0-0.4 | 0.29 ± 0.03 | 0.36 ± 0.08 |
| EO (K/µl) | 0.0-0.2 | 0.01 | 0.025 |
| BA (K/µl) | 0.0-0.2 | 0 | 0.005 |
| Erythrocytes |  |  |  |
| RBC (M/µl) | 6.36-9.42 | 9.69 ± 0.05 | 10.005 ± 0.04 |
| Hb (g/dl) | 11.0-15.1 | 12.85 ± 0.05 | 11.9 ± 0.30 |
| HCT (%) | 35.1-45.4 | 61.35 ± 0.15 | 55.3 ± 0.3 |
| MCV (fl) | 45.4-60.3 | 63.3 ± 0.20 | 55.25 ± 0.05 |
| MCH (pg) | 14.1-19.3 | 13.25 ± 0.15 | 11.85 ± 0.25 |
| MCHC (g/dl) | 30.2-34.2 | 20.95 ± 0.15 | 21.5 ± 0.4 |
| RDW (%) | 12.4-27.0 | 15.45 ± 0.05 | 17.25 ± 0.75 |
| Thrombocytes |  |  |  |
| PLT (K/µl) | 592-2972 | 855 ± 6 | 1023.5 ± 55.5 |
| MPV (fl) | 5.0-20.0 | 4.6 | 4.85 ± 0.05 |

Blood (~20 µl) was collected from female Npc1$^{+/-}$ (n = 2, age 63 and 66 days) and Npc1$^{-/-}$ mice (n = 2, age 63 and 66 days) by cheek bleed. Blood cell parameters were analyzed by Hemavet 950. Values represent mean ± SEM.
Abbreviations are, WBC = White Blood Cells, NE = Neutrophils, LY = Lymphocytes, MO = Monocytes, EO = Eosinophils, BA = Basophils, RBC = Red Blood Cells, Hb = Hemoglobin, HCT = Hematocrit, MCV = Mean Corpuscular Volume, MCH = Mean Corpuscular Hemoglobin, MCHC = Mean Corpuscular Hemoglobin Concentration, RDW = Red Cell Distribution width, PLT = Platelet, and MPV = Mean Platelet Volume. K/µl stands for 1000/µl.

REFERENCES

1. Vanier M T (2010) Niemann-Pick disease type C. Orphanet J Rare Dis 5: 16.
2. Rimkunas V M, Graham M J, Crooke R M, Liscum L (2008) In vivo antisense oligonucleotide reduction of NPC1 expression as a novel mouse model for Niemann Pick type C-associated liver disease. Hepatology 47: 1504-1512.
3. Sayre N L, Rimkunas V M, Graham M J, Crooke R M, Liscum L (2010) Recovery from liver disease in a Niemann-Pick type C mouse model. J Lipid Res 51: 2372-2383.
4. Smith D, Wallom K L, Williams I M, Jeyakumar M, Platt F M (2009) Beneficial effects of anti-inflammatory therapy in a mouse model of Niemann-Pick disease type C1. Neurobiol Dis 36: 242-251.
5. Vazquez M C, Del Pozo T, Robledo F A, Carrasco G, Pavez L, et al. (2011) Alteration of gene expression profile in niemann-pick type C mice correlates with tissue damage and oxidative stress. PLoS One 6: e28777.
6. Liao G, Cheung S, Galeano J, Ji A X, Qin Q, et al. (2009) Allopregnanolone treatment delays cholesterol accumulation and reduces autophagic/lysosomal dysfunction and inflammation in Npc1−/− mouse brain. Brain Res 1270: 140-151.
7. Rimkunas V M, Graham M J, Crooke R M, Liscum L (2009) TNF-{alpha} plays a role in hepatocyte apoptosis in Niemann-Pick type C liver disease. J Lipid Res 50: 327-333.
8. Beltroy E P, Richardson J A, Horton J D, Turley S D, Dietschy J M (2005) Cholesterol accumulation and liver cell death in mice with Niemann-Pick type C disease. Hepatology 42: 886-893.
9. Pressey S N, Smith D A, Wong A M, Platt F M, Cooper J D (2012) Early glial activation, synaptic changes and axonal pathology in the thalamocortical system of Niemann-Pick type C1 mice. Neurobiol Dis 45: 1086-1100.
10. Schrantz N, Sagiv Y, Liu Y, Savage P B, Bendelac A, et al. (2007) The Niemann-Pick type C2 protein loads isoglobotrihexosylceramide onto CD1d molecules and contributes to the thymic selection of NKT cells. J Exp Med 204: 841-852.
11. Sagiv Y, Hudspeth K, Mattner J, Schrantz N, Stern R K, et al. (2006) Cutting edge: impaired glycosphingolipid trafficking and NKT cell development in mice lacking Niemann-Pick type C1 protein. J Immunol 177: 26-30.
12. Baudry M, Yao Y, Simmons D, Liu J, Bi X (2003) Postnatal development of inflammation in a murine model of Niemann-Pick type C disease: immunohistochemical observations of microglia and astroglia. Exp Neurol 184: 887-903.
13. Liao G, Wen Z, Irizarry K, Huang Y, Mitsouras K, et al. (2010) Abnormal gene expression in cerebellum of Npc1−/− mice during postnatal development. Brain Res 1325: 128-140.
14. Lopez M E, Klein A D, Hong J, Dimbil U J, Scott M P (2012) Neuronal and epithelial cell rescue resolves chronic systemic inflammation in the lipid storage disorder Niemann-Pick C. Hum Mol Genet doi:101093/hmg/dds126.
15. Reddy J V, Ganley I G, Pfeffer S R (2006) Clues to neuro-degeneration in Niemann-Pick type C disease from global gene expression profiling. PLoS One 1: e19.
16. De Windt A, Rai M, Kytomaki L, Thelen K M, Lutjohann D, et al. (2007) Gene set enrichment analyses revealed several affected pathways in Niemann-pick disease type C fibroblasts. DNA Cell Biol 26: 665-671.
17. Tang Y, Leao I C, Coleman E M, Broughton R S, Hildreth J E (2009) Deficiency of niemann-pick type C-1 protein impairs release of human immunodeficiency virus type 1 and results in Gag accumulation in late endosomal/lysosomal compartments. J Virol 83: 7982-7995.
18. Watarai M, Makino S, Michikawa M, Yanagisawa K, Murakami S, et al. (2002) Macrophage plasma membrane cholesterol contributes to Brucella abortus infection of mice. Infect Immun 70: 4818-4825.
19. Goluszko P, Nowicki B (2005) Membrane cholesterol: a crucial molecule affecting interactions of microbial pathogens with mammalian cells. Infect Immun 73: 7791-7796.
20. Coppens I, Sinai A P, Joiner K A (2000) *Toxoplasma gondii* exploits host low-density lipoprotein receptor-mediated endocytosis for cholesterol acquisition. J Cell Biol 149: 167-180.
21. Gatfield J, Pieters J (2000) Essential role for cholesterol in entry of mycobacteria into macrophages. Science 288: 1647-1650.
22. Samuel B U, Mohandas N, Harrison T, McManus H, Rosse W, et al. (2001) The role of cholesterol and glycosylphosphatidylinositol-anchored proteins of erythrocyte rafts in regulating raft protein content and malarial infection. J Biol Chem 276: 29319-29329.
23. Carette J E, Raaben M, Wong A C, Herbert A S, Obernosterer G, et al. (2011) Ebola virus entry requires the cholesterol transporter Niemann-Pick C1. Nature 477: 340-343.
24. Cote M, Misasi J, Ren T, Bruchez A, Lee K, et al. (2011) Small molecule inhibitors reveal Niemann-Pick C1 is essential for Ebola virus infection. Nature 477: 344-348.
25. Tsolis R M, Kingsley R A, Townsend S M, Ficht T A, Adams L G, et al. (1999) Of mice, calves, and men. Comparison of the mouse typhoid model with other Salmonella infections. Adv Exp Med Biol 473: 261-274.
26. Haraga A, Ohlson M B, Miller S I (2008) Salmonellae interplay with host cells. Nat Rev Microbiol 6: 53-66.
27. Monack D M, Bouley D M, Falkow S (2004) *Salmonella typhimurium* persists within macrophages in the mesenteric lymph nodes of chronically infected Nramp1+/+ mice and can be reactivated by IFNgamma neutralization. J Exp Med 199: 231-241.
28. Li H, Repa J J, Valasek M A, Beltroy E P, Turley S D, et al. (2005) Molecular, anatomical, and biochemical events associated with neurodegeneration in mice with Niemann-Pick type C disease. J Neuropathol Exp Neurol 64: 323-333.
29. Parra J, Klein A D, Castro J, Morales M G, Mosqueira M, et al. (2011) Npc1 deficiency in the C57BL/6J genetic background enhances Niemann-Pick disease type C spleen pathology. Biochem Biophys Res Commun 413: 400-406.
30. Maue R A, Burgess R W, Wang B, Wooley C M, Seburn K L, et al. (2012) A novel mouse model of Niemann-Pick type C disease carrying a D1005G-Npc1 mutation comparable to commonly observed human mutations. Hum Mol Genet 21: 730-750.
31. Voikar V, Rauvala H, Ikonen E (2002) Cognitive deficit and development of motor impairment in a mouse model of Niemann-Pick type C disease. Behav Brain Res 132: 1-10.
32. Lynn D J, Winsor G L, Chan C, Richard N, Laird M R, et al. (2008) InnateDB: facilitating systems-level analyses of the mammalian innate immune response. Mol Syst Biol 4: 218.
33. Drummond R A, Brown G D (2011) The role of Dectin-1 in the host defense against fungal infections. Curr Opin Microbiol 14: 392-399.
34. Lee K H, Ono M, Inui M, Yuasa T, Takai T (2000) Stimulatory function of gp49A, a murine Ig-like receptor, in rat basophilic leukemia cells. J Immunol 165: 4970-4977.
35. Nakatsuji T, Gallo R L (2011) Antimicrobial Peptides: Old Molecules with New Ideas. J Invest Dermatol.
36. Repa J J, Li H, Frank-Cannon T C, Valasek M A, Turley S D, et al. (2007) Liver X receptor activation enhances cholesterol loss from the brain, decreases neuroinflammation, and increases survival of the NPC1 mouse. J Neurosci 27: 14470-14480.
37. Hofmann E, Reichart U, Gausterer C, Guelly C, Meijer D, et al. (2010) Octamer-binding factor 6 (Oct-6/Pou3f1) is induced by interferon and contributes to dsRNA-mediated transcriptional responses. BMC Cell Biol 11: 61.
38. Jiang Q, Li W O, Aiello F B, Klarmann K D, Keller J R, et al. (2005) Retroviral transduction of IL-7Ralpha into IL-7Ralpha−/− bone marrow progenitors: correction of lymphoid deficiency and induction of neutrophilia. Gene Ther 12: 1761-1768.
39. Kasten K R, Prakash P S, Unsinger J, Goetzman H S, England L G, et al. (2010) Interleukin-7 (IL-7) treatment accelerates neutrophil recruitment through gamma delta T-cell IL-17 production in a murine model of sepsis. Infect Immun 78: 4714-4722.
40. Parikh S S, Litherland S A, Clare-Salzler M J, Li W, Gulig P A, et al. (2003) CapG(−/−) mice have specific host defense defects that render them more susceptible than CapG(+/+) mice to *Listeria monocytogenes* infection but not to *Salmonella enterica* serovar *Typhimurium* infection. Infect Immun 71: 6582-6590.
41. Ripoll V M, Irvine K M, Ravasi T, Sweet M J, Hume D A (2007) Gpnmb is induced in macrophages by IFN-gamma and lipopolysaccharide and acts as a feedback regulator of proinflammatory responses. J Immunol 178: 6557-6566.
42. Wraith J E, Baumgartner M R, Bembi B, Covanis A, Levade T, et al. (2009) Recommendations on the diagnosis and management of Niemann-Pick disease type C. Mol Genet Metab 98: 152-165.
43. Yanjanin N M, Velez J I, Gropman A, King K, Bianconi S E, et al. (2010) Linear clinical progression, independent of age of onset, in Niemann-Pick disease, type C. Am J Med Genet B Neuropsychiatr Genet 153B: 132-140.
44. Porter F D, Scherrer D E, Lanier M H, Langmade S J, Molugu V, et al. (2010) Cholesterol oxidation products are sensitive and specific blood-based biomarkers for Niemann-Pick C1 disease. Sci Transl Med 2: 56ra81.
45. Patterson M C, Vecchio D, Prady H, Abel L, Wraith J E (2007) Miglustat for treatment of Niemann-Pick C disease: a randomised controlled study. Lancet Neurol 6: 765-772.
46. Liu B, Turley S D, Burns D K, Miller A M, Repa J J, et al. (2009) Reversal of defective lysosomal transport in NPC disease ameliorates liver dysfunction and neurodegeneration in the npc1−/− mouse. Proc Natl Acad Sci USA 106: 2377-2382.
47. Davidson C D, Ali N F, Micsenyi M C, Stephney G, Renault S, et al. (2009) Chronic cyclodextrin treatment of murine Niemann-Pick C disease ameliorates neuronal cholesterol and glycosphingolipid storage and disease progression. PLoS One 4: e6951.
48. Ramirez C M, Liu B, Taylor A M, Repa J J, Burns D K, et al. (2010) Weekly cyclodextrin administration normalizes cholesterol metabolism in nearly every organ of the Niemann-Pick type C1 mouse and markedly prolongs life. Pediatr Res 68: 309-315.
49. Xie X, Brown M S, Shelton J M, Richardson J A, Goldstein J L, et al. (2011) Amino acid substitution in NPC1 that abolishes cholesterol binding reproduces phenotype of complete NPC1 deficiency in mice. Proc Natl Acad Sci USA 108: 15330-15335.
50. Jethwaney D, Islam M R, Leidal K G, de Bernabe D B, Campbell K P, et al. (2007) Proteomic analysis of plasma membrane and secretory vesicles from human neutrophils. Proteome Sci 5: 12.
51. Lominadze G, Powell D W, Luerman G C, Link A J, Ward R A, et al. (2005) Proteomic analysis of human neutrophil granules. Mol Cell Proteomics 4: 1503-1521.
52. Vitner E B, Dekel H, Zigdon H, Shachar T, Farfel-Becker T, et al. (2010) Altered expression and distribution of cathepsins in neuronopathic forms of Gaucher disease and in other sphingolipidoses. Hum Mol Genet 19: 3583-3590.
53. Myerowitz R, Lawson D, Mizukami H, Mi Y, Tifft C J, et al. (2002) Molecular pathophysiology in Tay-Sachs and Sandhoff diseases as revealed by gene expression profiling. Hum Mol Genet 11: 1343-1350.
54. Cluzeau C V, Watkins-Chow D E, Fu R, Borate B, Yanjanin N, et al. (2012) Microarray expression analysis and identification of serum biomarkers for Niemann-Pick disease, type C1. Hum Mol Genet 21: 3632-3646.
55. Segal A W (2005) How neutrophils kill microbes. Annu Rev Immunol 23: 197-223.
56. Kumar V, Sharma A (2010) Neutrophils: Cinderella of innate immune system. Int Immunopharmacol 10: 1325-1334.
57. Nathan C (2006) Neutrophils and immunity: challenges and opportunities. Nat Rev Immunol 6: 173-182.
58. Mantovani A, Cassatella M A, Costantini C, Jailion S (2011) Neutrophils in the activation and regulation of innate and adaptive immunity. Nat Rev Immunol 11: 519-531.
59. El Kebir D, Filep J G (2010) Role of neutrophil apoptosis in the resolution of inflammation. ScientificWorldJournal 10: 1731-1748.
60. Silva M T (2011) Macrophage phagocytosis of neutrophils at inflammatory/infectious foci: a cooperative mechanism in the control of infection and infectious inflammation. J Leukoc Biol 89: 675-683.
61. Ajuebor M N, Hogaboam C M, Le T, Proudfoot A E, Swain M G (2004) CCL3/MIP-1alpha is pro-inflammatory in murine T cell-mediated hepatitis by recruiting CCR1-expressing CD4(+) T cells to the liver. Eur J Immunol 34: 2907-2918.
62. Silverstein E, Friedland J (1977) Elevated serum and spleen angiotensin converting enzyme and serum lysozyme in Gaucher's disease. Clin Chim Acta 74: 21-25.
63. DiRosario J, Divers E, Wang C, Etter J, Charrier A, et al. (2009) Innate and adaptive immune activation in the brain of MPS IIIB mouse model. J Neurosci Res 87: 978-990.
64. Ohmi K, Kudo L C, Ryazantsev S, Zhao H Z, Karsten S L, et al. (2009) Sanfilippo syndrome type B, a lysosomal storage disease, is also a tauopathy. Proc Natl Acad Sci USA 106: 8332-8337.
65. Trexler A J, Nilsson M R (2007) The formation of amyloid fibrils from proteins in the lysozyme family. Curr Protein Pept Sci 8: 537-557.
66. Vieira M N, Forny-Germano L, Saraiva L M, Sebollela A, Martinez A M, et al. (2007) Soluble oligomers from a non-disease related protein mimic Abeta-induced tau hyperphosphorylation and neurodegeneration. J Neurochem 103: 736-748.
67. Loftus S K, Morris J A, Carstea E D, Gu J Z, Cummings C, et al. (1997) Murine model of Niemann-Pick C disease: mutation in a cholesterol homeostasis gene. Science 277: 232-235.

Example 2

Plasma Signature of Neurological Disease in the Monogenetic Disorder Niemann Pick Type C Early diagnosis of neurological disorders would greatly improve their management and treatment. A major hurdle is that inflammatory products of cerebral disease are not easily detected in blood. Inflammation in multiple organs and heterogeneity in disease present additional challenges in distinguishing the extent to which a blood based marker reflects disease in brain or other afflicted organs. Murine models of the monogenetic disorder Niemann Pick Type C (NPC) present aggressive forms of cerebral and liver inflammatory disease. Microarray analyses previously revealed age-dependent changes in innate immunity transcripts in the mouse brain. We have now validated four putative secretory inflammatory markers that are also elevated in mouse liver. We include limited, but first time analysis of human NPC liver and cerebellum. Further we utilized 2-hydroxypropyl-beta-cyclodextrin (HPβCD; an emerging therapeutic) administered intraperitoneally in mice, which abrogates inflammatory pathology in the liver but has limited effect on the brain. By analyzing the corresponding effects on inflammatory plasma proteins, we identified cathepsin S as a lead indicator of liver disease. In contrast lysozyme was a marker of both brain and liver disease. HPβCD had no effect on transcripts of neuron specific 24-hydroxylase and its product 24(S)-hydroxycholesterol was not a useful indicator in mouse plasma. Our data suggest that dual analysis of levels of the inflammatory markers lysozyme and cathepsin S may enable detection of multiple distinct states of neurodegeneration in plasma.

Introduction

Inflammatory proteins, especially those of innate immunity are under investigation as biomarkers to monitor disease onset and progression in a wide range of neurodegenerative and metabolic disorders (1-3). Heterogeneity in the progression of these diseases underscores the critical need for biomarkers. This is particularly so for inherited lysosomal disorders, because they are rare which increases the challenges of detection and treatment. Multiple organs may be affected raising the question of whether markers reflect change in one or more organ systems. Plasma markers for neurological disease have been particularly elusive in both rare and more prevalent neurodegenerative disorders (such as Alzheimer's and Parkinson's).

Niemann-Pick Type C (NPC) is an autosomal recessive neurodegenerative, lysosomal disorder caused by defects in function of either genes Npc1 or Npc2, although in ~95% of patients disease is caused by defect in Npc1(4). Progressive neurodegeneration is a prominent feature. In addition, NPC is also recognized as a significant cause of liver disease in early life (5-7). A mouse model BALB/c Npc1$^{-/-}$ also known as Npc1$^{nih}$ where the Npc1 gene is truncated (8) enables the study of aggressive forms of brain and liver disease. Further, since terminal stage disease manifests under 90 days, it provides a relatively short model to monitor both neurodegenerative and liver disease.

Multiple inflammatory, innate immune changes have been reported by transcriptional and protein analysis in the liver, spleen and brain of NPC animals (9-12). At the cellular level, there is prominent accumulation of foamy macrophages in liver (9, 10, 13) and activation of microglia in brain (14). Impaired development and reduced natural killer T (NKT) cells in spleen and thymus have been found in NPC null mice (15, 16). In addition, expression arrays suggest transcriptional changes in NPC cells grown in in vitro cultures (17, 18).

We investigated conserved transcriptional changes seen in the brain throughout the life span of the Npc1$^{nih}$ mouse by examining animals at six different ages, from weaning to late neurodegeneration (19). These analyses revealed innate immunity trends that could not be obtained from isolated (or a few) time points. We compared them to changes in the liver to identify age-dependent elevation of eight genes of lysosomal innate immunity proteins in the brain and the liver, suggesting they may be potentially suitable as biomarkers for disease in both organs and secreted into plasma. The top candidate lysozyme was validated in plasma of Npc1$^{nih}$ and Npc1$^{nmf164}$ (Npc1$^{nmf}$, a BALB/c strain with a point mutation (D1005G) in the NPC1 protein). Our analyses also revealed that neutrophils accumulate in the NPC liver suggesting a new cellular component that contributes to inflammatory damage there. In independent studies, Cluzeau et at (20) correlated age-dependent gene expression in mouse liver to identify two plasma markers validated in mice and humans but their link to molecular changes in the brain was not investigated.

Our interest is also to understand how potential biomarkers and inflammatory changes will serve to assess therapies and their differential effects on disease in brain. To do this, we expanded validation of candidate genes using multiple members of the cathepsin family in brain and liver of murine models. We also extended findings in mice to a limited, but first molecular analysis of human cerebellum and liver. Further we monitored changes in cathepsins as well as previously identified lysozyme in mice treated with 2-hydroxypropyl-beta-cyclodextrin (HPβCD, commonly known as cyclodextrin), an emerging therapeutic known to improve disease outcomes in mice (21-24) and being expanded for use in humans. Cathepsins are cysteine and aspartic proteases which secreted into the body fluid including blood and several cathepsins have been identified as a blood based markers for several cancers and inflammatory diseases (25-27). However, use of cathepsins as plasma biomarkers in neurodegenerative lysosomal disorders has been poorly explored. Lysozyme transcripts were the most highly elevated in the brain and their elevation in mouse plasma has been reported (19), but how the contribution from the liver could be distinguished from that in the brain remained unknown.

Experimental Procedures

Materials

All fine chemicals were obtained from Sigma (St Louis, Mo., USA), unless otherwise indicated. For immunohistochemistry (IHC), rat anti-mouse Ly-6G (clone 1A8, BioXcell) was used to detect neutrophils and monoclonal anti-calbindin (C9848, Sigma) antibody was used for Purkinje neurons. Rabbit anti-CTSS (H-50) antibodies was from Santa Cruz Biotechnology (Dallas, Tex., USA). Antibodies to lysozyme (28) were a kind gift of Professor Tomas Ganz, (University of California at Los Angeles). Oligonucleotides for qPCR were purchased from Invitrogen (Carlsbad, Calif., USA).

Production of Npc1$^{nih}$ and Npc1$^{nmf164}$ Mutant Mice

Breeding pair of Npc1$^{nih}$ (BALB/c Nctr-Npc1$^{m1N}$/J) mice was purchased from Jackson laboratory (Bar Harbor, Me., USA). It is a widely used NPC BALB/c strain (8), carrying a truncation and premature translation of NPC1 protein and originally established by Peter Pentchev at the National Institutes of Health (Bethesda, Md., USA). Npc1$^{nmf164}$ is a BALB/c strain derived from the recently described Npc1$^{nmf164}$ in C57BL/6J (29) which contains an ethyl-nitroso urea-induced point mutation in the Npc1 gene. The mutation is a single nucleotide change (A to G at cDNA bp 3163) resulting in an aspartate to glycine change at position 1005 (D1005G) resulting in slower diseases progression due to partial loss in NPC1 function. The mutation was transferred from C57BL/6J to the BALB/c strain by Robert P. Erickson, University of Arizona Health Sciences Center, Tucson, Ariz., USA. Homozygous mutants of both strains (Npc1$^{-/-}$) along with wild type littermates (Npc1$^{+/+}$), were generated by crossing heterozygous mutant (Npc1$^{+/-}$) males and females, in-house. Npc1$^{nih}$ Mouse pups were genotyped according to published protocols (8) whereas Npc1$^{nmf164}$ mice were genotyped based on PCR followed by digestion with BstEII (29). In this study, unless otherwise indicated, Npc1$^{nih}$ mice were used.

RNA Extraction

In mice, formalin fixed paraffin embedded tissue was sectioned (4-5 μm) and total RNA was isolated using RNeasy FFPE kit (Qiagen, Germantown, Md., USA) which included treatment with DNAse. Frozen human liver and cerebellum from 4 NPC patients and 4 age-, gender- and ethnicity-matched controls were obtained from the NICHD Brain and Tissue Bank for Developmental Disorders (University of Maryland, Baltimore, Md., USA), as approved by the Institutional Review Board (IRB), of the University of Notre Dame, Ind., USA (FWA 00002462). Total RNA was isolated using RNeasy kit (Qiagen, Germantown, Md., USA). Eluted RNA was further digested with RNase free DNaseI and re-purified using RNeasy column. The quality of RNA was checked using Bioanalyzer chip (Agilent Technologies, Santa Clara, Calif., USA) and quantity was determined using Nanodrop 2000 (Thermo Fisher Scientific, Waltham, Mass., USA).

Quantitative PCR

Quantitative PCR (qPCR) was performed using Power SYBR Green RNA-to-$C_T$ 1-Step Kit and an ABI Prism 7500 Fast real-time PCR system (Applied Biosystems, Grand Island, USA). Reaction was set in 20 μl using 100 nM primers and 5-100 ng total RNA as template. The thermal cycling parameters were as follows: step 1, 48° C. for 30 min; step 2, 95° C. for 10 min; step 3, 95° C. for 15 sec °C.; step 4, 60° C. for 15 sec. Step 3-4 was repeated for 40 cycles followed by melt curve analysis. The nucleotide sequence of gene specific primers and their sources are listed in Table 1. Specific amplification was validated by analysis of template titration, melt curves and agarose gel electrophoresis. In both mouse and human tissues, the mRNA levels were normalized to the housekeeping gene, Gapdh (Glyceraldehyde 3-phosphate dehydrogenase). Fold change was calculated by relative standard curve method after correcting PCR efficiency. In mice, the fold change in expression levels of different genes in Npc1$^{-/-}$ was calculated relative to average levels of expression in Npc1$^{+/-}$ mice. In human tissues, fold change in transcript expression in NPC liver and cerebellum was expressed relative to average expression in age-matched controls.

Lysozyme Activity Assay

Lysozyme activity in plasma was measured using fluorescence based lysozyme assay kit (EnzCheck, Life Technologies, Carlsbad, Calif., USA) as describer earlier (19). Plasma corresponding to 25 μg protein from female and male Npc1$^{nih}$ mice was used in a 100 μl reaction volume. The reaction was carried out at 37° C. for 24 h. Fluorescence was read using excitation/emission of 494/518 nm in a multiwell plate reader spectramax M2 (Molecular devices, CA, USA). The values obtained were normalized by dividing the numbers by the mean value of lysozyme obtained among untreated Npc1$^{+/-}$ mice. Purified chicken egg white lysozyme was used as a positive control.

Cathepsin S ELISA

Plasma total Cathepsin S was determined using ELISA Duo Set kit (DY1183) from R&D Systems (Minneapolis, Minn., USA) according to the manufacturer's instructions. Plasma of Npc1$^{+/+}$ and Npc1$^{+/-}$ mice of both Npc1$^{nih}$ and Npc1$^{nmf164}$ strains was diluted to 1:10 whereas Npc1$^{-/-}$ mice of both strains were diluted to 1:20. All measurements were done in triplicate wells. For normalization, the raw absorbance values were divided by the average absorbance of Npc1$^{+/-}$ mice of each strain of a given age group.

24(S)-Hydroxy Cholesterol (24-HC) ELISA

Plasma 24-HC concentration was determined using ELISA kit from Enzo Life Sciences (Farmingdale, N.Y., USA) according to the manufacturer's instructions. Plasma was diluted to 1:1000 in supplied buffer and measurements were done in triplicate wells. Pure 24-HC (supplied with kit) was used to prepare the standard curve. 24-HC concentration was normalized to plasma protein content.

Organ Harvest and Immunohistochemistry

Mice were sacrificed by asphyxiation using $CO_2$. The circulatory bed was washed with PBS (pH 7.4), and subsequently perfused with 10% neutral buffered formalin (~4% formaldehyde). The organs (brain and liver) were surgically harvested and stored in 4% formaldehyde at room temperature (RT) until transfer to paraffin. Paraffin-embedded tissue sections (3-4 μm) were dewaxed in xylene and alcohol. For Ly-6G and calbindin staining, antigen retrieval was done by pre-incubating deparaffinized samples with 0.05% proteinase K (Dako, Germany) in 50 mM Tris-HCl (pH 7.5) for 8 min at RT. CTSS and lysozyme were retrieved by boiling the sections in acidic condition for 30 min. Sections were incubated with anti-Ly-6G (20 μg/ml), anti-calbindin (1:1000), anti-CTSS (20 μg/ml) or anti-lysozyme (1:20) overnight at 4° C. Reagents were prepared according to the manufacturer's instructions (Vector laboratories). The staining protocol was followed as described previously (19). The secondary antibody for neutrophil staining was biotinylated rabbit anti-rat IgG (mouse absorbed, Vector Laboratories) and for Purkinje neurons was biotinylated horse anti-mouse IgG (Vector Laboratories).

For fluorescence microscopy, FITC-conjugated IgG (MP Biomedicals, Solon, Ohio, USA) was the secondary antibody. Sections stained only with secondary antibodies served as controls. Brightfield images were acquired on a Nikon Olympus microscope, using a Nikon digital DS-Fi1-U2 camera controlled by NIS-Elements F3.0 Nikon software (all from Nikon Instruments INC, Tokyo, Japan). Images were visualized with A10 PL 10x/0.25, or a DPIan Apo 40x/1.00 oil-immersion or a DPIan Apo 100x/1.30 oil-immersion objective lens (Nikon). Fluorescence microscopy and digital image collection were performed using an Olympus IX inverted fluorescence microscope and a Photometrix cooled CCD camera (CH350/LCCD) driven by DeltaVision software from Applied Precision (Seattle, Wash., USA). DeltaVision software (softWoRx) was used to deconvolve these images. Images were visualized with 40x oil-immersion objective lens and are single optical sections. ImageJ (National Institute of Health, Bethesda, Md., USA) software was used to process and quantify the fluorescence intensity of CTSS and lysozyme.

Drug Injections and Blood Withdrawal

Starting at P21 and once a week thereafter, $Npc1^{nih}$ and $Npc1^{nmf164}$ mice were injected i.p with 20% 2-hydroxypropyl-beta-cyclodextrin (HPβCD, 4000 mg/Kg) prepared in 0.2% DMSO and 0.9% saline. Control mice received 0.2% DMSO in 0.9% saline. Blood was collected either via cheek bleed or terminal heart bleed from mice in EDTA tubes (BD Biosciences, San Jose, Calif., USA). Plasma was separated by centrifugation at 2500 rpm for 15 min and stored at −70° C. until used.

Statistical Tests

Student's t test was carried out to determine the statistical significance of the data. P<0.05 considered significant.

Results

Validation of Cathepsin b (Ctsb), d (Ctsd) and d (Ctss) in Liver and Brain of NPC Mice and NPC Patients Out of twelve potential biomarker genes identified in our previous study (19), three belonged to cathepsin family. These were cathepsin B (Ctsb), cathepsin D (Ctsd) and cathepsin S (Ctss). Although, there is no information about cathepsin S in NPC disease, cathepsins B and D have been reported to be over expressed in the cerebellar neurons in $Npc1^{-/-}$ mouse brain and have been linked to increased neurodegeneration (30-32), suggesting the family may be suitable for further investigation.

Figure 12:
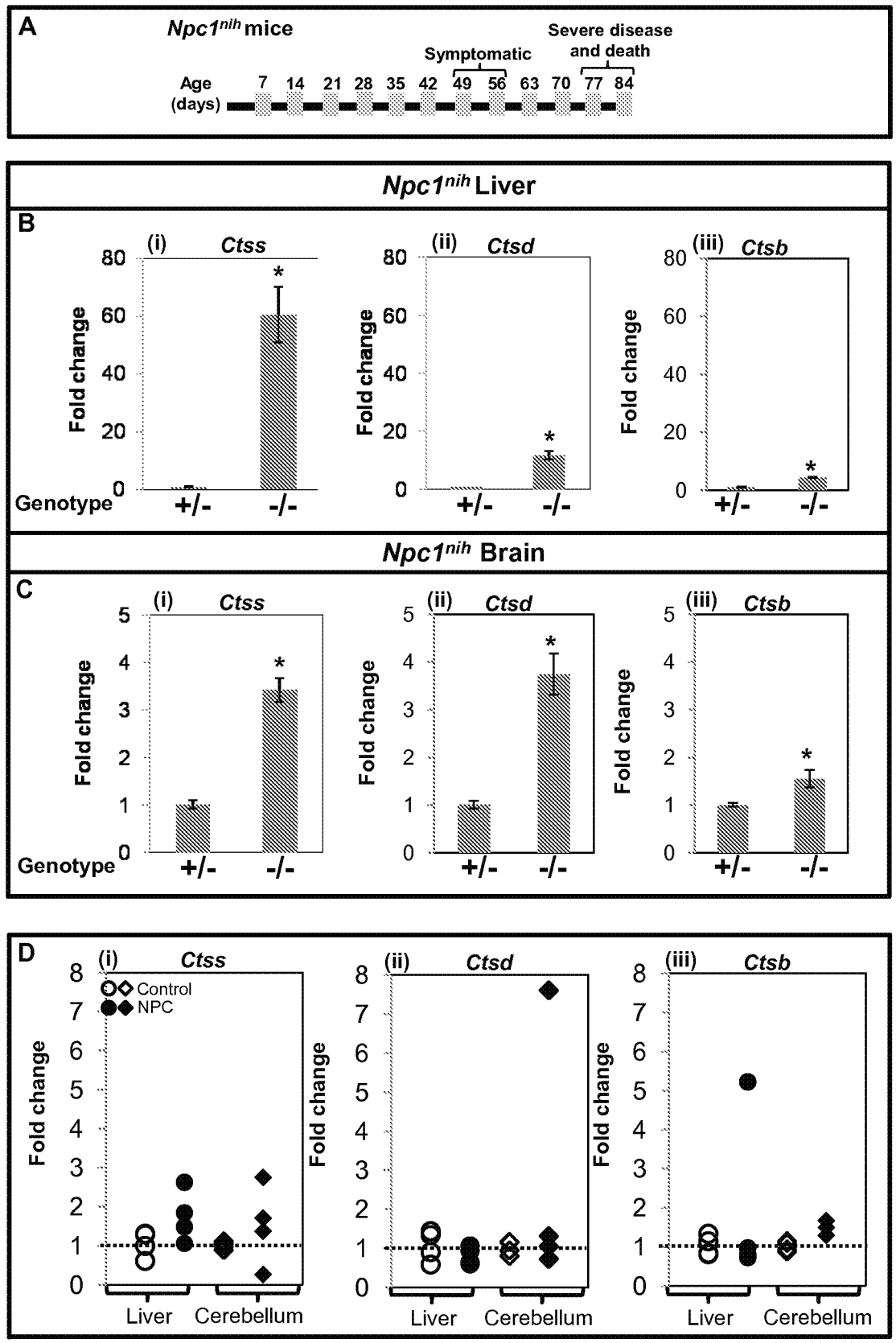
FIG. 12. Elevated expression of cathepsin s, d and b in NPC mice and patients. (A) Diagrammatic representation of the onset of phenotypic symptoms and life span of Npc1$^{nih}$ mice. qPCR reveals that Ctss (cathepsin s), Ctsd (cathepsin d) and Ctsb (cathepsin b) transcripts are elevated in liver (B, i-iii) and brain (C, i-iii) of Npc1$^{-/-}$ (-/-) mice compared to Npc1+/- (+/-) counterparts at 70-83 days. Each group consisted of 4 mice. The data represent mean triplicate values±SD. (D, i-iii) Expression analysis of Ctss, Ctsd and Ctsb in liver and cerebellum of human NPC patients. Total RNA was isolated from frozen liver and cerebellum from 4 NPC and 4 control subjects. Expression levels of cathepsins were determined by qPCR. Fold change is relative to average value of control subjects. Change above 1 (shown by dotted line) represents the extent of over expression. For both mouse and human qPCR studies, Gapdh was used as an internal control. *p<0.005.

Disease progression as a function of age in $Npc1^{-/-}$ mice is shown schematically in FIG. 12A. Our microarray data suggested that the fold up regulation of Ctsb, Ctsd and Ctss was 1.5, 3.2 and 6.2 respectively in the liver of late stage $Npc1^{-/-}$ mice compared to age-matched control mice (Table 2). Similarly, transcript levels of Ctsb, Ctsd and Ctss were 2.8, 1.9 and 2.7 fold higher in the brain of $Npc1^{-/-}$ mice compared to controls (Table 2). In order to validate the microarray data, we performed qPCR to determine transcript increases for Ctsb, Ctsd and Ctss in liver and brain of $Npc1^{-/-}$ mice at a late symptomatic stage (FIG. 12). As shown in FIG. 12B (panels i-iii), in the liver, the fold change in Ctsb was 4.4, Ctsd 11.7 and Ctss 60.6 in $Npc1^{-/-}$ compared to age-matched control mice. In the brain, the fold increase of Ctsb was 1.5, Ctsd 3.7 and Ctss 3.4. (FIG. 12C, panels i-iii).

The fold change detected by qPCR was not the same as seen in the microarrays. Many factors such as mRNA extraction and stability, hybridization efficiency, difference in the efficiency of cDNA synthesis may contribute to this discrepancy. While microarrays are useful in obtaining trends of change, qPCR provides the quantitative confirmatory data.

Cluzeau et al (20) have reported that plasma cathepsin D is elevated in NPC patients. However information on levels of cathepsin D, S and B in human organs are not available. We therefore obtained frozen liver and cerebellum from 4 NPC and 4 control subjects matched for age, gender and ethnicity. As shown in FIG. 12D panel i, we detected increased transcripts of Ctss in liver (1.4, 1.8 and 2.6 fold) as well as in cerebellum (1.4, 1.7 and 2.8 fold) of three NPC patients. In the fourth NPC patient, Ctss transcript was unchanged in liver but decreased in cerebellum compared to controls (FIG. 12D, panel i). In contrast, Ctsd expression was not increased in liver but increase (1.3 and 7.6 fold) was seen in two NPC cerebellum (FIG. 12D, panel ii). Ctsb showed elevation (5.2 fold) in one out of four liver samples and in the cerebellum of all four NPC patients (1.3, 1.3, 1.5 and 1.7 fold) (FIG. 12D, panel iii). Since the sample size is small, the data do not rule out Ctsd or Ctsb as potential markers. Nevertheless, since there was increase in Ctss in 3 of 4 patient samples for both organs and Ctss showed the greatest change in the mouse liver (60.6-fold), we investigated it as a lead marker of interest in subsequent work.

Figure 13:
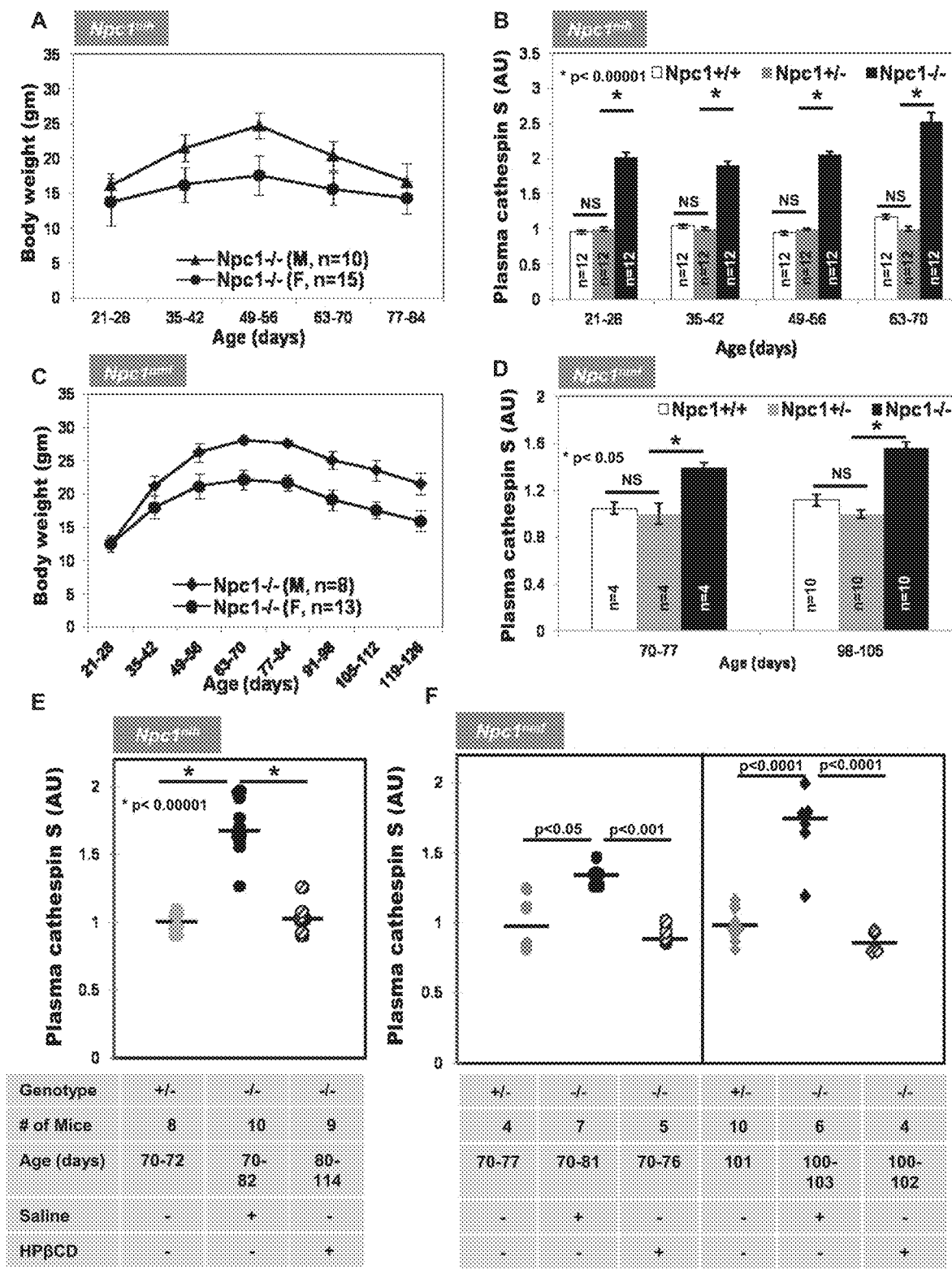
FIG. 13. Plasma cathepsin S levels are elevated in Npc1$^{nih}$ and Npc1$^{nmf164}$ mice and reduced after cyclodextrin treatment. (A) Weight as a function of age for Npc1$^{nih}$ male and female mice. Homozygous mutant Npc1$^{nih}$ (Npc1$^{-/-}$) mice begin weight loss at 49-56 days, followed by further decrease and death at 77-84 days. (B) Elevated cathepsin S detected in plasma of Npc1$^{nih}$ Npc1$^{-/-}$ mice as determined by ELISA (Material and Methods). (C) Weight as a function of age of Npc1$^{nmf}$ male and female mice. Homozygous mutant Npc1$^{nmf}$(Npc1$^{-/-}$) mice lose weight from 84-91 days onward, followed by further decrease and death at 119-126 days. (D) Elevated cathepsin S level in plasma of Npc1$^{nmf}$ Npc1$^{-/-}$ mice. (E) Cathepsin S levels in Npc1$^{nih}$ Npc1$^{-/-}$ (-/-) mice treated with saline or HPβCD compared to Npc1$^{+/-}$ (+/-). (F) Cathepsin S levels in Npc1$^{nmf}$ Npc1$^{-/-}$ (-/-) mice treated with saline or HPβCD, compared to Npc1$^{+/-}$ (+/-). In panels B, D, E, F, blood plasma was sampled at indicated time points. Fold change in cathepsin S is expressed relative to average levels of activity in Npc1$^{+/-}$ mouse plasma. The data represent mean triplicate values±SD. Median values shown by horizontal lines. Statistical significance was determined using Student's t test. 'NS' indicates not significant.

Characterization of Plasma Cathepsin S Levels in $Npc1^{nih}$ and $Npc1^{nmf}$ Mice and the Response to HPβCD In NPC mice, weight provides a central parameter to follow disease progression. The data in FIG. 13A shows the weight curves of male and female $Npc1^{nih}$ mice as a function of their age in days. As shown in FIG. 13B, plasma cathepsin S (CTSS) in $Npc1^{-/-}$ mice was significantly elevated at all ages compared to age matched $Npc1^{+/+}$ and $Npc1^{+/-}$ mice. At the first three time points (21-28, 35-42 and 49-56 days), the levels were ~2-fold higher (p<0.00001), which at later times (63-70 days), became further elevated to ~2.5-fold increase (p<0.00001) (FIG. 13B). The data shown in FIG. 13B are derived from both male and female animals, suggesting elevation of CTSS was independent of gender.

We further examined plasma from Npc1$^{nmf}$ mouse. Previous studies suggested that Npc1$^{nmf}$ in the C57BL/6J background have a life span of ~112 days and develop progressive disease (29). BALB/c Npc1$^{nmf}$ have comparable life span (~120-125 days) and exhibited weight loss from 85-90 days (19). As shown in FIG. 13C, plasma CTSS levels were indeed elevated ~1.4-1.6-fold (p<0.05) in both early (~75 days) and later (100 days) symptomatic stages. Remarkably HPβCD reduced levels of CTSS at late stages (80-114 days) of Npc1$^{nih}$ (FIG. 13E) and mild to moderately symptomatic Npc1$^{nmf}$ mice to those seen in healthy controls (FIG. 13E-F). These findings were surprising, because HPβCD-treated Npc1$^{nih}$ and Npc1$^{nmf}$ mice manifest disease at 100 days of age.

Effect of HPβCD Treatment on Ctss, Ctsd Ctsb and Other Inflammatory Marker Expression in Liver and the Pathologies of the Organ in Npc1$^{nih}$ Mice In order to investigate whether cathepsin levels in the plasma of Npc1$^{-/-}$ mice reflect disease status of the liver and its response to HPβCD, we studied the effect of treatment on (i) the expression levels of Ctss, Ctsd and Ctsb and (ii) liver pathology. After HPβCD treatment, the expression of Ctss in the liver of late stage Npc1$^{-/-}$ mice was markedly reduced and equivalent to control mice (FIG. 14A). Similar trends were also observed in the expression of Ctsd and Ctsb. (FIG. 14B-C).

We undertook analysis of additional inflammatory markers and histology. We studied the expression of two inflammatory genes, Cd68 (macrophage marker) and Itgax (marker of activated macrophage, granulocytes, dendritic cells etc, also known as Cd11c). qPCR analysis showed that Cd68 was up regulated by ~88-fold (FIG. 14D) and Itgax by ~400-fold (FIG. 14E) in Npc1$^{-/-}$ mice at late stages (70-83 days) in the liver. These were reduced to normal levels after HPβCD treatment (FIG. 14D-E), suggesting amelioration of liver inflammation. A third marker Col1a (procollagen type 1a) shown to be up regulated during liver fibrosis (10), was increased (~1.3-fold) in Npc1$^{-/-}$. HPβCD induced anomalous reduction in its expression (FIG. 14F), suggesting that although HPβCD treatment reduced inflammation, it may also adversely change levels of important molecular determinants of the liver.

To study the expression of CTSS protein and its localization in the liver, sections were subjected to IHC using anti-CTSS antibodies. The liver of Npc1$^{+/-}$ mice (age 80 days) showed healthy hepatocyte architecture (FIG. 15A). In contrast, numerous large foamy macrophages containing high levels of CTSS were seen in Npc1$^{-/-}$ mice of the same age (FIG. 15B, blue arrows). Saline had no effect (FIG. 15C) but HPβCD treatment eliminated accumulation of foamy macrophages and dramatically reduced CTSS accumulation in Npc1$^{-/-}$ (FIG. 15D).

Figure 15:
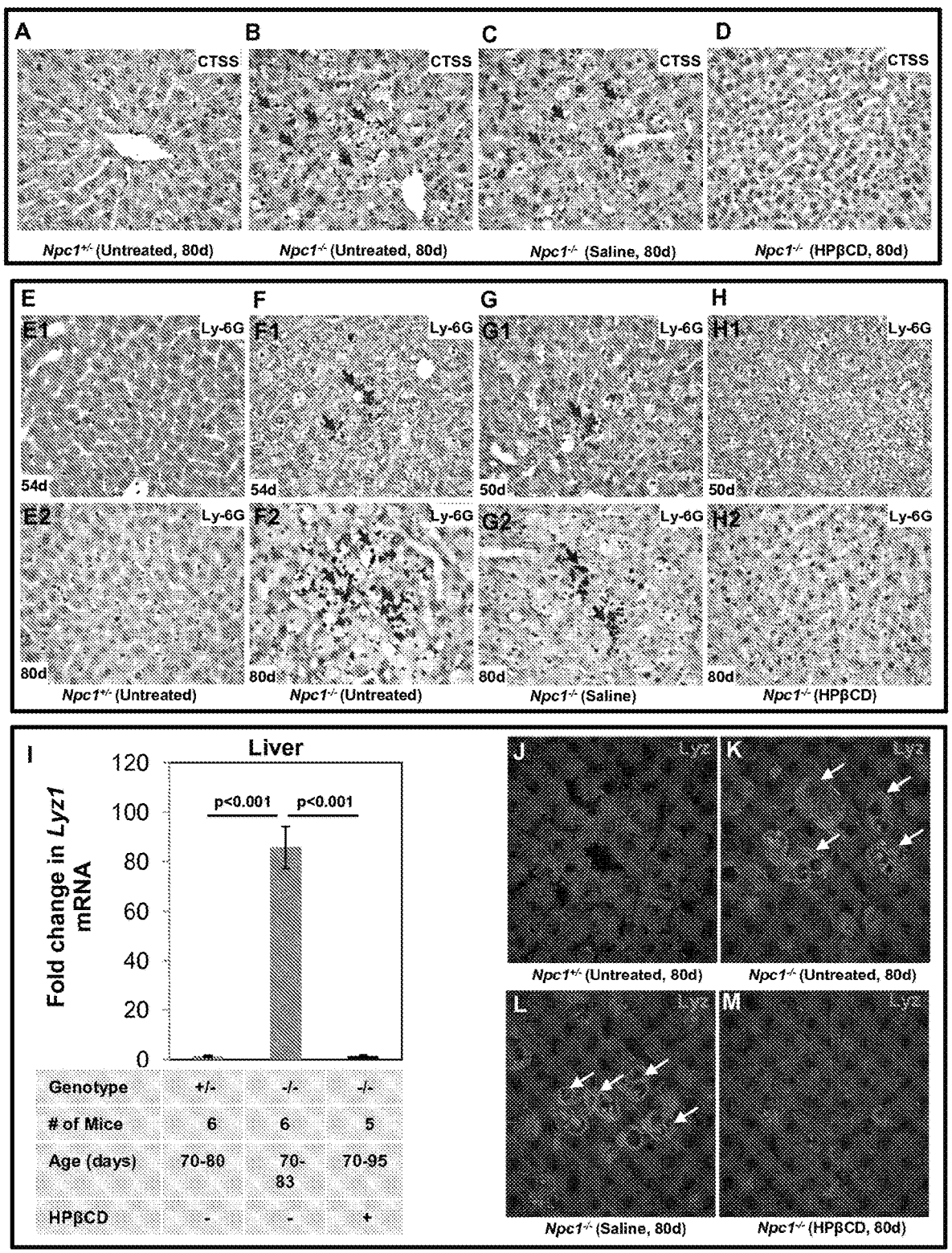
FIG. 15. Treatment with cyclodextrin reduces the cathepsin S (CTSS) level, accumulation of neutrophils and lysozyme in Npc1$^{nih}$ mouse liver. A-D. Formalin-fixed paraffin embedded liver sections (4-5 μm) of Npc1$^{+/-}$ and Npc1$^{-/-}$ mice at indicated ages were stained with anti-CTSS antibodies. The micrographs show the labeling of CTSS in (A) untreated Npc1$^{+/-}$ mice (B) untreated Npc1$^{-/-}$ mice (C)

We previously reported that giant foci of neutrophils accumulate in liver of Npc1$^{-/-}$ mice, suggesting they contribute to the inflammatory response (19). We therefore also examined the effects of HPβCD on neutrophil accumulation in the liver. Immunohistochemical analyses did not show neutrophil infiltration in healthy mice at 54 and 80 days (FIG. 15, E1-E2). In contrast, in diseased mice, clusters of neutrophils were clearly seen (Ly-6G+ve cells in brown, shown by blue arrows, FIG. 15, F1). The number of neutrophils increased in the liver of diseased mice at 80 days (FIG. 15, F2). Administration of saline had no effect (FIG. 15, G1-G2), but HPβCD treatment reduced neutrophil clusters at both 50 (FIG. 15, H1) and 80 days (FIG. 15, H2). However, there were differences in hepatocyte architecture (decreased cytoplasmic staining with slight irregular plasma membrane) in animals treated with HPβCD, suggesting treatment does not completely restore all aspects of liver health (at least as judged by histochemistry).

Our previous microarray studies also reported the up regulation of lysozyme transcripts in the liver of diseased animals. As shown in FIG. 15I, we detected ~85-fold up regulation of Lyz1 (Lysozyme1) gene in the Npc1$^{-/-}$ liver at late stages of disease compared to age matched control mice. HPβCD treatment abrogated Lyz1 over expression in the liver of Npc1$^{-/-}$ mice, bringing transcript levels back to those seen in healthy mice (FIG. 15I). To confirm that lysozyme protein levels were also elevated and determine the site(s) of concentration, we undertook immunohistochemical analyses of liver sections using antibodies to mouse lysozyme (see Materials and Methods). Large foamy macrophages contained high levels of lysozyme in the liver of Npc1$^{-/-}$ mice (age 80 days). They were absent in healthy animals (FIG. 4, J-K). HPβCD-treatment (FIG. 15M) but not saline (FIG. 15L) largely eliminated the macrophages containing lysozyme from the liver. A low, basal level of lysozyme expression was seen in hepatocytes but at levels comparable to healthy mice (FIG. 15M).

Figure 14:
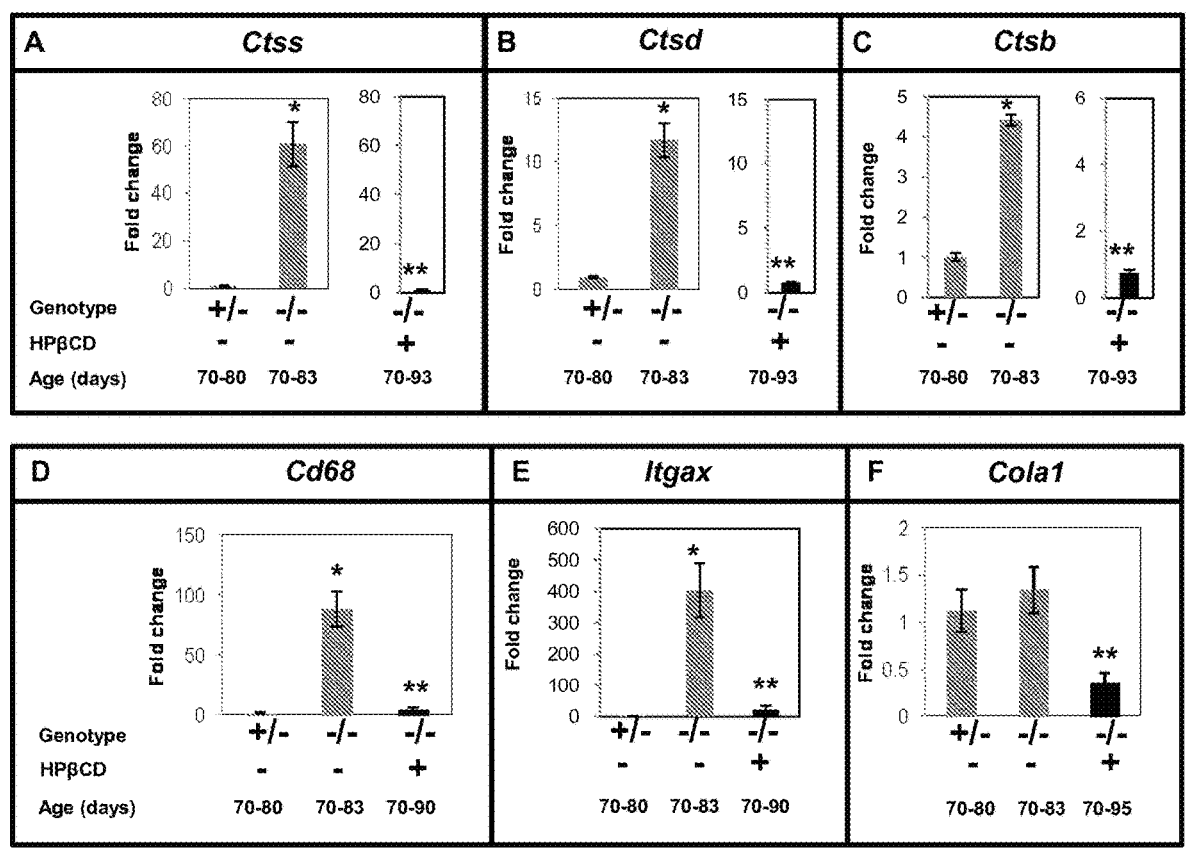
FIG. 14. Effect of cyclodextrin treatment on the expression of cathepsins and additional markers of inflammation and fibrosis in mouse liver. Ncp1$^{nih}$ Npc1$^{-/-}$ mice (-/-) were given weekly HPβCD injection. Npc1$^{+/-}$ (+/-) animals remained untreated. Animals were sacrificed at indicated ages, organs were removed and processed, and total RNA was extracted. qPCR was undertaken to determine the expression level of (A) Ctss (B) Ctsd (C) Ctsb (D) Cd68 (E) Itgax and (F) Cola1. Each group consisted of 4 mice except for the Col1a assay. Col1a included 6 Npc1$^{+/-}$, 6 untreated Npc1$^{-/-}$ and 7 HPβCD-treated Npc1$^{-/-}$ mice. Fold change shown indicates transcript levels in Npc1$^{-/-}$ relative to Npc1$^{+/-}$ mice. Gapdh was used as internal control. The data represent the mean±SD. The data shown for untreated Npc1$^{-/-}$ mice in 'A-C' are identical to those shown in FIG. 12B to enable comparisons across the study. * Npc1$^{+/-}$ vs untreated Npc1$^{-/-}$, p<0.005; ** untreated Npc1$^{-/-}$ vs treated Npc1$^{-/-}$, p<0.005.

Together these data provide new markers (such as CTSS and lysozyme) to confirm prior findings that HPβCD treatment improves inflammation in the liver. Further they show that HPβCD treatment returns CTSS levels in the liver of diseased animals to that seen in healthy counterparts (FIG. 14-15) analogous to effects seen with this marker in plasma (FIG. 14).

Effect of HPβCD Treatment on Ctss, Ctsd and Ctsb Expression in Brain and the Pathologies of the Organ in Npc1$^{nih}$ Mice In the brain, HPβCD treatment resulted in partial reduction of Ctss and Ctsd (FIG. 16A-B) whereas, Ctsb expression returned to normal levels (FIG. 16C). Activation of microglia and astrocytes in the brain has been associated with neuroinflammation and neurodegeneration in NPC disease (14, 33, 34). qPCR analyses of associated markers revealed ~24-fold up regulation of Cd68 in Npc1$^{-/-}$ mice (70-83 days) compared to age matched Npc1+/– mice (FIG. 16D). The expression of Cd68 in Npc1$^{-/-}$ mice treated with HPβCD reduced significantly but still contained ~6-fold higher transcript relative to Npc1$^{+/-}$ mice (FIG. 16D). Further, mutant animals showed ~44-fold increase in Mip-1α transcripts which was reduced to ~27-fold upon treatment with HPβCD (FIG. 16E). Untreated Npc1$^{-/-}$ mice at late stages showed ~9-fold higher Gfap transcript compared to age-matched controls (FIG. 16F), which was slightly reduced in HPβCD-treated animals (FIG. 16F). These results are consistent with the data with Ctsb, d, and s as markers and prior reports that HPβCD partially alleviates neuroinflammation in Npc1$^{-/-}$ mice (23, 35-37).

Immunohistochemical analyses of brain sections showed enhanced labeling of CTSS in the pyramidal neurons of hippocampus of Npc1$^{-/-}$ mice (FIG. 16G-J), recognized by their characteristic morphology. Quantitative analysis using ImageJ revealed ~1.7 fold (p<0.05) increase in CTSS in Npc1$^{-/-}$ mice. HPβCD treatment slightly reduced CTSS levels (~20%) whereas saline had no effect (FIG. 16K). CTSS was expressed at low levels in the rest of the brain (not shown) but there were no differences between Npc1$^{+/-}$ and Npc1$^{-/-}$ mice elsewhere, including the cerebellum (data not shown).

Loss of Purkinje neurons in the cerebellum is a characteristic feature of NPC disease and has been used as a benchmark to study brain pathology (24, 34, 38, 39). To study the effect of HPβCD on Purkinje neurons death, immunohistochemical staining of sagittal sections of brain of Npc1$^{-/-}$ mice was carried out using anti-calbindin (markers of Purkinje neurons) antibodies. Mouse cerebellum is composed of ten (I-X) different lobules. All cerebellar sections were examined, however in FIG. 17, micrographs corresponding to IX lobule have been shown as representative images. Numerous Purkinje neurons (FIG. 17A, stained in brown, shown by arrows) were clearly seen in the cerebellar section of Npc1$^{+/-}$ mouse at 80 days whereas in Npc1$^{-/-}$ mice of same age the numbers were markedly reduced (5-8/lobules) (FIG. 17B). This was unchanged upon treatment with saline (FIG. 17C). However, treatment with HPβCD preserved additional Purkinje neurons in the IX lobule of the cerebellum (FIG. 17D) although at lower levels than Npc1$^{+/-}$ animals. The intensity of calbindin positive neurons in HPβCD-treated Npc1$^{-/-}$ mouse were reduced compared to Npc1$^{+/-}$ animals (compare intensity of brown staining seen in FIG. 17A1-A2 with FIG. 17D1-D2). Purkinje neurons were also seen in the X lobule (data not shown). Even after HPβCD treatment, Purkinje neurons were barely seen in the rest of the cerebellar regions of Npc1$^{-/-}$ mice (data not shown). A semi-quantitative analysis of Purkinje neurons in a cerebellar section showed they were significantly reduced in number in Npc1$^{-/-}$ (39±11) mice as compared to Npc1$^{+/-}$ mice (473±75). Saline treatment showed no effect (40±8) whereas HPβCD treatment showed increased number of Prukinje neurons (100±16) (FIG. 17E). The data are consistent with prior results (22, 24, 40) that HPβCD treatment may to a small degree resolve neuroinflammation and inhibit loss of Purkinje neurons. Further, they are consistent with our marker analysis for inflammatory proteins including the cathepsins.

Characterization of Lysozyme Levels in Plasma, and Brain in HPβCD-Treated Npc1$^{nih}$ Mice at Terminal Stages of Disease: Localization of Lysozyme Elevation in the Cerebellum and Development of a Composite Scale to Distinguish Between Four Distinct States of Cerebral and Liver Disease Our prior studies (19) identified lysozyme transcripts as most highly elevated in the brain of Npc1$^{nih}$ mice. We further validated elevation of lysozyme in the plasma of Npc1$^{nih}$ as well as a second model Npc1$^{nmf}$ mice. Additionally, we showed that plasma lysozyme levels elevated in asymptomatic Npc1$^{nmf}$ mice (age ~50 days) were reduced by HPβCD treatment and rendered comparable to untreated wild type animals (19).

To examine time points of advanced disease, we returned to the shorter, Npc1$^{nih}$ model. This model typically manifests phenotypic symptoms (weight loss, gait, tremor etc.) from ~50-55 days and survives up to ~80-84 days (FIG. 18A). Previous studies have shown that weekly injections of HPβCD to Npc1$^{nih}$ reduce disease and extend the survival (23, 24). We therefore treated Npc1$^{-/-}$ mice with HPβCD or vehicle control (0.2% DMSO in 0.9% saline) with once a week drug injections (4000 mg/Kg) starting at age P21. Npc1$^{nih}$ treated with this regime showed delayed onset of symptoms (from ~49-56 days to ~70-80) and survived ~105-112 days (diagrammatically represented in FIG. 18A). As reported earlier, the plasma lysozyme activity of vehicle treated Npc1$^{-/-}$ mice was elevated on average 2-fold in early symptomatic (50-60 days) animals (FIG. 18B) and remained elevated at the late symptomatic stage (70 days) compared to age matched controls (FIG. 18C). Further, HPβCD treatment at 50-60 days reduced plasma lysozyme activity levels seen in wild type mice (FIG. 18B). At 80+ days HPβCD-treated animals showed reduction of plasma lysozyme compared to mock treated animals, but nonetheless displayed a 1.5-fold increase compared to normal animals (FIG. 18C).

This persistent elevation of plasma lysozyme could not be derived from the liver, since as previously shown HPβCD treatment restored lysozyme transcript and protein to normal levels in the liver (FIG. 14-15). We therefore examined the brain, where qPCR revealed ~81-fold up regulation Lyz1 in Npc1$^{-/-}$ mice at late stages of disease (FIG. 18D). Moreover after HPβCD treatment Lyz1 expression remained elevated by ~28 fold (FIG. 18D).

In immunolocalization studies by fluorescence microscopy, low levels of lysozyme were detected throughout the brains of normal and disease mice, except for the cerebellum, where there was marked increase in the mutant animals (FIG. 19B-K). Numerous cells, highly positive for lysozyme were seen in the cerebellar white mater of Npc1$^{-/-}$ mice (80 days) but not in Npc1$^{+/-}$ mice (FIG. 19B-C). HPβCD treatment had no significant effect on the lysozyme levels in the cerebellum (FIG. 19E-F). Lysozyme was also elevated in the molecular layer of the cerebellum (FIG. 19G-K). In this region, healthy mice showed minimal levels of lysozyme staining (FIG. 19G) whereas elevated fibrillar staining was seen in the Npc1$^{-/-}$ mice (FIG. 19H). Saline treatment had no effect, but HPβCD treatment resulted in a minor reduction (~25%; FIG. 19I-K). Although CTSS was increased in the hippocampus of mutant mice (FIG. 16G-J) lysozyme was unchanged here (FIG. 19L-P) and as indicated earlier, in the rest of the brain (data not shown).

In several instances, fold changes in plasma levels of both cathepsin and lysozyme were considerably lower than their transcript levels in brain and liver but more in keeping with changes seen by IHC, which is to be expected since the latter is a read out of protein levels in tissue. Taken together these data suggest that HPβCD given post weaning into the body cavity, can deplete lysozyme in the liver. It may also reduce to a small extent lysozyme in the brain, but significant levels persist. Remarkably lysozyme elevation in the brain of diseased animals appears concentrated in the cerebellum, whose function is prominently compromised in NPC (summarized in FIG. 19Q).

Nonetheless, prior to HPβCD treatment, plasma levels of lysozyme are likely to reflect inflammation in the brain as well as the liver in mice and humans (FIGS. 4, 7, 8 and 9A). In order to estimate the contribution from the inflamed liver, we needed a second marker whose levels in plasma solely reflect that of the liver (such as CTSS). Thus we considered that lysozyme along with CTSS, may contribute to a composite, quartile scale for both inflamed cerebral and liver disease (FIG. 20B i-iii). The first two quartiles reflect elevated lysozyme and thus potential contribution from cerebral disease (FIG. 20B). However, simultaneous elevation of CTSS in the second quartile, suggests liver inflammation that can also contribute lysozyme to the plasma. Accordingly, HPβCD which abrogates CTSS decreases lysozyme by 50%, reflecting that one half of lysozyme activity is contributed by the liver and the other half by the brain. Thus for the same lysozyme levels, quartile 2 is expected to reflect more moderate levels of cerebral disease compared to quartile 1 (FIG. 20B). Quartile 4 reflects low disease, while quartile 3 is indicative of just liver disease (FIG. 20B).

Comparison to Oxysterol Markers

Oxysterol species are emerging as markers of NPC disease (41, 42). Plasma oxysterols (7-ketocholesterol (7-KC) and 3β, 5α, 6β-Triol) generated by non-enzymatic pathways are largely produced by liver (43, 44) and thus are likely to be more useful to understand liver pathology rather than the brain pathology. However 24(S)-hydroxycholesterol [24(S)-HC], is derived from cholesterol by an enzyme 24-hydroxylase, which is primarily expressed in the neurons of central nervous system (45, 46). As shown in FIG. 10A, we detected ~25% reduction in the expression of Cyp46a1 (24-hydroxylase) gene in the brain of Npc1$^{-/-}$ mice at late stage disease. This is consistent with a slight reduction of 24(S)-HC reported in NPC patients (42), but our analysis of human cerebellum in four patients suggested variability in transcript levels (FIG. 21B). Unexpectedly, the levels of 24(S)-HC level in the plasma of Npc1$^{-/-}$ mice were elevated and remained largely unaffected after HPβCD treatment (FIG. 21C). Thus plasma 24(S)-HC may not assess neuropathology in mouse models.

Discussion

Oxysterols are emerging as sensitive blood-based biomarkers for NPC (42). However they are largely products of the liver not the brain. In addition, the disease is heterogeneous with respect to both neurological and metabolic symptoms as well as age of onset, which strongly argues for the need for multiple markers.

Elevation of several cathepsins including CTSB, CTSD and CTSS have been implicated in the neurodegenerative diseases (47). The level and activity of CTSB and CTSD is elevated in the hippocampal, cerebellar and cortical neurons (30, 31, 34) of Npc1$^{-/-}$ mice. By IHC CTSS can be detected in almost all regions of brain. However CTSS was elevated only in hippocampal neurons of Npc1$^{-/-}$ mice compared to healthy counterparts. It is possible that the hippocampal neurons can tolerate a minor elevation of these proteases and remain resistant to degeneration. Increased cytosolic level of CTSB and CTSD has been shown to activate the autophagic pathways thereby leading to neuronal death in Npc1$^{-/-}$ cells or mice (31, 32). CTSS may do the same. Additionally, activated microglia can release CTSB and CTSD that along with CTSS can induce neuronal death through digestion of extracellular matrix (48).

But importantly, CTSS detected in plasma of NPC mouse models does not reflect cerebral disease but is derived largely from the liver. Our studies suggest that amongst the cathepsins, S appears to be the best candidate biomarker for liver disease. Although transcript analysis in mouse organs suggests that Ctss increases gradually, direct measurements in plasma revealed high levels from the outset. The marked elevation of Ctss in the liver and its concomitant responsiveness to HPβCD treatment in plasma and liver, suggests that it may be a preferred marker of early liver disease. This is of value because although neurodegeneration is a prominent feature and linked to fatal disease, NPC is recognized as a significant cause of liver disease in early life (5-7). A history of neonatal jaundice or persisting hepatosplenomegaly are common among patients with early- and late infantile onset disease. NPC is the second most common cause of neonatal cholestasis resulting in liver failure and death of ~10% patients (49, 50). Thus, along with oxysterols, plasma CTSS may also help in diagnosis of NPC particularly in a new born child or infants manifesting cholestatic jaundice along with hepatomegaly or splenomegaly.

The Purkinje cell layer (PCL) in the cerebellum contains two types of cells, Purkinje neurons and Bergmann glial cells (BGCs). At advanced disease states, the Purkinje neurons are largely lost in Npc1$^{-/-}$ mice. This suggests that increased lysozyme in PCL layer and molecular layer (ML) is due to its expression and secretion by BGCs. Activated microglia and BGCs may secrete higher level of lysozyme that may also play a role in the loss of Purkinje neurons in Npc1$^{-/-}$ mice (through mechanisms that remain poorly defined undefined). Lysozyme at higher concentration has been shown to be amyloidogenic (51) and exposure of cultured rat neurons to oligomers of hen egg white lysozyme had been found to induce hyperphosphorylation of tau (52). In fact neurons expressing lysozyme have been shown to have increased hyperphosphoylated tau in the MPS IIIB mouse brain (28). Therefore, it is plausible that over expression of lysozyme may allow it to reach a critical concentration at which it either oligomerizes or aggregates and serve as template for the aggregation of tau and its phosphorylation, in the cerebellum. Importantly cerebellar ataxia is a major clinical symptom of NPC.

Prior studies have suggested that macrophage activation and accumulation in the liver is responsive to HPβCD treatment (22, 23) We confirm that with two new markers CTSS and lysozyme and also show that neutrophils accumulation is reduced, suggesting both types of inflammatory cells respond to lipid accumulation. One possibility is that anomalous neutrophil migration occurs in response to changes in lipid gradients to inflict inflammatory damage which is then removed by macrophage action. At late stages of disease, reduction of inflammatory proteins lysozyme and CTSS in plasma closely corresponds to reduction of inflammation in the liver. Yet the liver is not completely 'normal'. The observed reduction of collagen in liver can be correlated with compromised cellular organization, suggesting that high levels of HPβCD in circulation may also have adverse effects on liver. Nonetheless the dramatic reduction in inflammation may outweigh, resulting in net benefit. Further studies are required to establish improved liver function.

HPβCD injections has been previously been shown to slightly but detectably improve brain pathology and levels of inflammatory markers (21-24, 35, 37). Our data are consistent with these findings, both with respect to organ pathologies as well as marker analysis. Nonetheless the improvement in the liver pathology after HPβCD treatment far exceeds that in the brain. In the initial microarray analysis of age-dependent increase in transcripts, lysozyme was the top most transcript hit. Since both brain pathology and plasma lysozyme levels are relatively refractory to intraperitoneal HPβCD injections, it is likely they are linked. Indeed HPβCD-treated animals, although rescued in liver pathology, nonetheless die of cerebral disease.

How loss of the NPC protein function leads to neuroinflammation is poorly understood. One possibility is that lysosomal functions are compromised due to harmful accumulation of cholesterol and other lipids. In response, cellular systems may compensate the functional loss by overexpressing lysosomal proteins such as cathepsins and lysozyme. This may be a general phenomenon as neuroinflammation is hallmark of almost all LSDs (2, 53). Malfunctioning of lysosomal system may hamper phagocytosis, rapid membrane synthesis and recycling in macrophages and microglial cells, which in turn may lead to their activation and subsequent overexpression of markers of neuroinflammation.

Inflammatory proteins corresponding to members of chemokines and cytokines family have been explored in CSF of NPC patients however further investigation is required to establish their usefulness as biomarkers (54). Oxysterols largely reflect liver function. However 24(S)-HC has been proposed as a marker for neuronal disease in humans since it is produced in the brain, but in the Npc1$^{-/-}$ mouse model we fail to provide insights into the utility of this marker for human disease.

Rather our data show that plasma lysozyme is derived from the brain and over expressed in the cerebellum. This is important since cerebellar ataxia is a major symptom of NPC. Lysozyme in conjunction with CTSS may be used to distinguish distinct states of brain and liver disease that has hitherto not been possible but would be very helpful to monitoring the progression and management of human disease. In this regard mouse models may be particularly helpful in dissecting the differential response of major disease organs to emerging therapeutics in both preclinical and clinical studies.

REFERENCES

1. Cappellano, G., M. Carecchio, T. Fleetwood, L. Magistrelli, R. Cantello, U. Dianzani, and C. Comi. 2013. Immunity and inflammation in neurodegenerative diseases. *American journal of neurodegenerative disease* 2: 89-107.
2. Parkinson-Lawrence, E. J., T. Shandala, M. Prodoehl, R. Plew, G. N. Borlace, and D. A. Brooks. 2010. Lysosomal storage disease: revealing lysosomal function and physiology. *Physiology (Bethesda, Md.* 25: 102-115.
3. Wilms, H., L. Zecca, P. Rosenstiel, J. Sievers, G. Deuschl, and R. Lucius. 2007. Inflammation in Parkinson's diseases and other neurodegenerative diseases: cause and therapeutic implications. *Current pharmaceutical design* 13: 1925-1928.
4. Vanier, M. T. 2010. Niemann-Pick disease type C. *Orphanet J Rare Dis* 5: 16.
5. Patterson, M. C., C. J. Hendriksz, M. Walterfang, F. Sedel, M. T. Vanier, and F. Wijburg. 2012. Recommendations for the diagnosis and management of Niemann-Pick disease type C: an update. *Mol Genet Metab* 106: 330-344.
6. Garver, W. S., G. A. Francis, D. Jelinek, G. Shepherd, J. Flynn, G. Castro, C. Walsh Vockley, D. L. Coppock, K. M. Pettit, R. A. Heidenreich, and F. J. Meaney. 2007. The National Niemann-Pick C1 disease database: report of clinical features and health problems. *Am J Med Genet A* 143A: 1204-1211.
7. Imrie, J., S. Dasgupta, G. T. Besley, C. Harris, L. Heptinstall, S. Knight, M. T. Vanier, A. H. Fensom, C. Ward, E. Jacklin, C. Whitehouse, and J. E. Wraith. 2007. The natural history of Niemann-Pick disease type C in the UK. *Journal of inherited metabolic disease* 30: 51-59.
8. Loftus, S. K., J. A. Morris, E. D. Carstea, J. Z. Gu, C. Cummings, A. Brown, J. Ellison, K. Ohno, M. A. Rosenfeld, D. A. Tagle, P. G. Pentchev, and W. J. Pavan. 1997. Murine model of Niemann-Pick C disease: mutation in a cholesterol homeostasis gene. *Science* 277: 232-235.
9. Rimkunas, V. M., M. J. Graham, R. M. Crooke, and L. Liscum. 2008. In vivo antisense oligonucleotide reduction of NPC1 expression as a novel mouse model for Niemann Pick type C-associated liver disease. *Hepatology* 47: 1504-1512.
10. Sayre, N. L., V. M. Rimkunas, M. J. Graham, R. M. Crooke, and L. Liscum. 2010. Recovery from liver disease in a Niemann-Pick type C mouse model. *Journal of lipid research* 51: 2372-2383.
11. Smith, D., K. L. Wallom, I. M. Williams, M. Jeyakumar, and F. M. Platt. 2009. Beneficial effects of anti-inflammatory therapy in a mouse model of Niemann-Pick disease type C1. *Neurobiol Dis* 36: 242-251.
12. Vazquez, M. C., T. Del Pozo, F. A. Robledo, G. Carrasco, L. Pavez, F. Olivares, M. Gonzalez, and S. Zanlungo. 2011. Alteration of gene expression profile in niemann-pick type C mice correlates with tissue damage and oxidative stress. *PloS one* 6: e28777.
13. Beltroy, E. P., J. A. Richardson, J. D. Horton, S. D. Turley, and J. M. Dietschy. 2005. Cholesterol accumulation and liver cell death in mice with Niemann-Pick type C disease. *Hepatology* 42: 886-893.
14. Pressey, S. N., D. A. Smith, A. M. Wong, F. M. Platt, and J. D. Cooper. 2012. Early glial activation, synaptic changes and axonal pathology in the thalamocortical system of Niemann-Pick type C1 mice. *Neurobiol Dis* 45: 1086-1100.
15. Schrantz, N., Y. Sagiv, Y. Liu, P. B. Savage, A. Bendelac, and L. Teyton. 2007. The Niemann-Pick type C2 protein loads isoglobotrihexosylceramide onto CD1d molecules and contributes to the thymic selection of NKT cells. *J Exp Med* 204: 841-852.
16. Sagiv, Y., K. Hudspeth, J. Mattner, N. Schrantz, R. K. Stern, D. Zhou, P. B. Savage, L. Teyton, and A. Bendelac. 2006. Cutting edge: impaired glycosphingolipid trafficking and NKT cell development in mice lacking Niemann-Pick type C1 protein. *J Immunol* 177: 26-30.
17. Reddy, J. V., I. G. Ganley, and S. R. Pfeffer. 2006. Clues to neuro-degeneration in Niemann-Pick type C disease from global gene expression profiling. *PloS one* 1: e19.
18. De Windt, A., M. Rai, L. Kytomaki, K. M. Thelen, D. Lutjohann, L. Bernier, J. Davignon, J. Soini, M. Pandolfo, and R. Laaksonen. 2007. Gene set enrichment analyses revealed several affected pathways in Niemann-pick disease type C fibroblasts. *DNA Cell Biol* 26: 665-671.
19. Alam, M. S., M. Getz, I. Safeukui, S. Yi, P. Tamez, J. Shin, P. Velazquez, and K. Haldar. 2012. Genomic expression analyses reveal lysosomal, innate immunity proteins, as disease correlates in murine models of a lysosomal storage disorder. *PloS one* 7: e48273.
20. Cluzeau, C. V., D. E. Watkins-Chow, R. Fu, B. Borate, N. Yanjanin, M. K. Dail, C. D. Davidson, S. U. Walkley, D. S. Ory, C. A. Wassif, W. J. Pavan, and F. D. Porter. 2012. Microarray expression analysis and identification of serum biomarkers for Niemann-Pick disease, type C1. *Hum Mol Genet* 21: 3632-3646.
21. Liu, B., H. Li, J. J. Repa, S. D. Turley, and J. M. Dietschy. 2008. Genetic variations and treatments that affect the lifespan of the NPC1 mouse. *Journal of lipid research* 49: 663-669.
22. Liu, B., S. D. Turley, D. K. Burns, A. M. Miller, J. J. Repa, and J. M. Dietschy. 2009. Reversal of defective lysosomal transport in NPC disease ameliorates liver dysfunction and neurodegeneration in the npc1−/− mouse. *Proc Natl Acad Sci USA* 106: 2377-2382.
23. Ramirez, C. M., B. Liu, A. M. Taylor, J. J. Repa, D. K. Burns, A. G. Weinberg, S. D. Turley, and J. M. Dietschy. 2010. Weekly cyclodextrin administration normalizes cholesterol metabolism in nearly every organ of the Niemann-Pick type C1 mouse and markedly prolongs life. *Pediatr Res* 68: 309-315.
24. Davidson, C. D., N. F. Ali, M. C. Micsenyi, G. Stephney, S. Renault, K. Dobrenis, D. S. Ory, M. T. Vanier, and S. U. Walkley. 2009. Chronic cyclodextrin treatment of murine Niemann-Pick C disease ameliorates neuronal cholesterol and glycosphingolipid storage and disease progression. *PloS one* 4: e6951.
25. Leto, G., F. M. Tumminello, G. Pizzolanti, G. Montalto, M. Soresi, I. Ruggeri, and N. Gebbia. 1996. Cathepsin D serum mass concentrations in patients with hepatocellular carcinoma and/or liver cirrhosis. *Eur J Clin Chem Clin Biochem* 34: 555-560.

26. Herszenyi, L., F. Farinati, R. Cardin, G. Istvan, L. D. Molnar, I. Hritz, M. De Paoli, M. Plebani, and Z. Tulassay. 2008. Tumor marker utility and prognostic relevance of cathepsin B, cathepsin L, urokinase-type plasminogen activator, plasminogen activator inhibitor type-1, CEA and CA 19-9 in colorectal cancer. *BMC Cancer* 8: 194.

27. Lv, B. J., J. S. Lindholt, X. Cheng, J. Wang, and G. P. Shi. 2012. Plasma cathepsin S and cystatin C levels and risk of abdominal aortic aneurysm: a randomized population-based study. *PloS one* 7: e41813.

28. Ohmi, K., L. C. Kudo, S. Ryazantsev, H. Z. Zhao, S. L. Karsten, and E. F. Neufeld. 2009. Sanfilippo syndrome type B, a lysosomal storage disease, is also a tauopathy. *Proc Natl Acad Sci USA* 106: 8332-8337.

29. Maue, R. A., R. W. Burgess, B. Wang, C. M. Wooley, K. L. Sebum, M. T. Vanier, M. A. Rogers, C. C. Chang, T. Y. Chang, B. T. Harris, D. J. Graber, C. A. Penatti, D. M. Porter, B. S. Szwergold, L. P. Henderson, J. W. Totenhagen, T. P. Trouard, I. A. Borbon, and R. P. Erickson. 2012. A novel mouse model of Niemann-Pick type C disease carrying a D1005G-Npc1 mutation comparable to commonly observed human mutations. *Hum Mol Genet* 21: 730-750.

30. Liao, G., Y. Yao, J. Liu, Z. Yu, S. Cheung, A. Xie, X. Liang, and X. Bi. 2007. Cholesterol accumulation is associated with lysosomal dysfunction and autophagic stress in Npc1−/− mouse brain. *Am J Pathol* 171: 962-975.

31. Amritraj, A., K. Peake, A. Kodam, C. Salio, A. Merighi, J. E. Vance, and S. Kar. 2009. Increased activity and altered subcellular distribution of lysosomal enzymes determine neuronal vulnerability in Niemann-Pick type C1-deficient mice. *Am J Pathol* 175: 2540-2556.

32. Amritraj, A., Y. Wang, T. J. Revett, D. Vergote, D. Westaway, and S. Kar. 2013. Role of cathepsin D in U18666A-induced neuronal cell death: potential implication in Niemann-Pick type C disease pathogenesis. *J Biol Chem* 288: 3136-3152.

33. Lopez, M. E., A. D. Klein, U. J. Dimbil, and M. P. Scott. 2011. Anatomically defined neuron-based rescue of neurodegenerative Niemann-Pick type C disorder. *J Neurosci* 31: 4367-4378.

34. German, D. C., C. L. Liang, T. Song, U. Yazdani, C. Xie, and J. M. Dietschy. 2002. Neurodegeneration in the Niemann-Pick C mouse: glial involvement. *Neuroscience* 109: 437-450.

35. Liu, B., C. M. Ramirez, A. M. Miller, J. J. Repa, S. D. Turley, and J. M. Dietschy. 2010. Cyclodextrin overcomes the transport defect in nearly every organ of NPC1 mice leading to excretion of sequestered cholesterol as bile acid. *Journal of lipid research* 51: 933-944.

36. Grammatikakis, I., N. Evangelinakis, G. Salamalekis, V. Tziortzioti, C. Samaras, C. Chrelias, and D. Kassanos. 2009. Prevalence of severe pelvic inflammatory disease and endometriotic ovarian cysts: a 7-year retrospective study. *Clin Exp Obstet Gynecol* 36: 235-236.

37. Ramirez, C. M., B. Liu, A. Aqul, A. M. Taylor, J. J. Repa, S. D. Turley, and J. M. Dietschy. 2011. Quantitative role of LAL, NPC2, and NPC1 in lysosomal cholesterol processing defined by genetic and pharmacological manipulations. *Journal of lipid research* 52: 688-698.

38. Ko, D. C., L. Milenkovic, S. M. Beier, H. Manuel, J. Buchanan, and M. P. Scott. 2005. Cell-autonomous death of cerebellar purkinje neurons with autophagy in Niemann-Pick type C disease. *PLoS genetics* 1: 81-95.

39. Yu, T., and A. P. Lieberman. 2013. Npc1 acting in neurons and glia is essential for the formation and maintenance of CNS myelin. *PLoS genetics* 9: e1003462.

40. Taylor, A. M., B. Liu, Y. Mari, B. Liu, and J. J. Repa. 2012. Cyclodextrin mediates rapid changes in lipid balance in Npc1−/− mice without carrying cholesterol through the bloodstream. *Journal of lipid research* 53: 2331-2342.

41. Jiang, X., R. Sidhu, F. D. Porter, N. M. Yanjanin, A. O. Speak, D. T. te Vruchte, F. M. Platt, H. Fujiwara, D. E. Scherrer, J. Zhang, D. J. Dietzen, J. E. Schaffer, and D. S. Ory. 2011. A sensitive and specific LC-MS/MS method for rapid diagnosis of Niemann-Pick C1 disease from human plasma. *Journal of lipid research* 52: 1435-1445.

42. Porter, F. D., D. E. Scherrer, M. H. Lanier, S. J. Langmade, V. Molugu, S. E. Gale, D. Olzeski, R. Sidhu, D. J. Dietzen, R. Fu, C. A. Wassif, N. M. Yanjanin, S. P. Marso, J. House, C. Vite, J. E. Schaffer, and D. S. Ory. 2010. Cholesterol oxidation products are sensitive and specific blood-based biomarkers for Niemann-Pick C1 disease. *Sci Transl Med* 2: 56ra81.

43. Olsen, B. N., P. H. Schlesinger, D. S. Ory, and N. A. Baker. 2012. Side-chain oxysterols: from cells to membranes to molecules. *Biochimica et biophysica acta* 1818: 330-336.

44. Brown, A. J., and W. Jessup. 2009. Oxysterols: Sources, cellular storage and metabolism, and new insights into their roles in cholesterol homeostasis. *Molecular aspects of medicine* 30: 111-122.

45. Hughes, T. M., C. Rosano, R. W. Evans, and L. H. Kuller. 2013. Brain cholesterol metabolism, oxysterols, and dementia. *J Alzheimers Dis* 33: 891-911.

46. Leoni, V., and C. Caccia. 2011. Oxysterols as biomarkers in neurodegenerative diseases. *Chemistry and physics of lipids* 164: 515-524.

47. Pislar, A., and J. Kos. Cysteine Cathepsins in Neurological Disorders. *Molecular neurobiology*. DOI 10.1007/s12035-013-8576-6

48. Nakanishi, H. 2003. Microglial functions and proteases. *Molecular neurobiology* 27: 163-176.

49. Kelly, D. A., B. Portmann, A. P. Mowat, S. Sherlock, and B. D. Lake. 1993. Niemann-Pick disease type C: diagnosis and outcome in children, with particular reference to liver disease. *J Pediatr* 123: 242-247.

50. Yerushalmi, B., R. J. Sokol, M. R. Narkewicz, D. Smith, J. W. Ashmead, and D. A. Wenger. 2002. Niemann-pick disease type C in neonatal cholestasis at a North American Center. *J Pediatr Gastroenterol Nutr* 35: 44-50.

51. Trexler, A. J., and M. R. Nilsson. 2007. The formation of amyloid fibrils from proteins in the lysozyme family. *Curr Protein Pept Sci* 8: 537-557.

52. Vieira, M. N., L. Forny-Germano, L. M. Saraiva, A. Sebollela, A. M. Martinez, J. C. Houzel, F. G. De Felice, and S. T. Ferreira. 2007. Soluble oligomers from a non-disease related protein mimic Abeta-induced tau hyperphosphorylation and neurodegeneration. *J Neurochem* 103: 736-748.

53. Vitner, E. B., F. M. Platt, and A. H. Futerman. 2010. Common and uncommon pathogenic cascades in lysosomal storage diseases. *J Biol Chem* 285: 20423-20427.

54. Cologna, S. M., C. V. Cluzeau, N. M. Yanjanin, P. S. Blank, M. K. Dail, S. Siebel, C. L. Toth, C. A. Wassif, A. P. Lieberman, and F. D. Porter. 2013. Human and mouse neuroinflammation markers in Niemann-Pick disease, type C1. *Journal of inherited metabolic disease*.

55. Vitner, E. B., H. Dekel, H. Zigdon, T. Shachar, T. Farfel-Becker, R. Eilam, S. Karlsson, and A. H. Futerman.

2010. Altered expression and distribution of cathepsins in neuronopathic forms of Gaucher disease and in other sphingolipidoses. *Hum Mol Genet* 19: 3583-3590.
56. Hruz, T., M. Wyss, M. Docquier, M. W. Pfaffl, S. Masanetz, L. Borghi, P. Verbrugghe, L. Kalaydjieva, S. Bleuler, O. Laule, P. Descombes, W. Gruissem, and P. Zimmermann. 2011. RefGenes: identification of reliable and condition specific reference genes for RT-qPCR data normalization. *BMC genomics* 12: 156.
57. Repa, J. J., H. Li, T. C. Frank-Cannon, M. A. Valasek, S. D. Turley, M. G. Tansey, and J. M. Dietschy. 2007. Liver X receptor activation enhances cholesterol loss from the brain, decreases neuroinflammation, and increases survival of the NPC1 mouse. *J Neurosci* 27: 14470-14480.
Footnotes The abbreviations used are: NPC, Neimann-Pick Type C; CTSS, cathepsin S; Lyz, Lysozyme; HPβCD, 2-hydroxypropyly-b eta-cyclo dextrin; 24(S)-HC, 24-hydroxycholesterol.

Example 3

Analysis of Lysozyme and Cathepsin S Markers in Plasma from Human Subjects to Distinguish Brain and Liver Disease A major hurdle is that inflammatory products of cerebral disease are not easily detected in blood. Inflammation in multiple organs and heterogeneity in disease present additional challenges in distinguishing the extent to which a blood based marker reflects disease in brain or other afflicted organs. We utilized murine models of the monogenetic disorder Niemann Pick Type C (NPC) that present aggressive forms of cerebral and liver inflammatory disease to identify secretory biomarkers for neuroinflammation. Genome-wide transcriptome data led us identify 12 candidate genes of secretory proteins that showed age-dependent over expression in both liver and brain. We utilized 2-hydroxypropyl-beta-cyclodextrin (HPβCD; an emerging therapeutic) administered intraperitoneally in mice, which abrogates inflammatory pathology in the liver but has limited effect on the brain. By analyzing the corresponding effects on inflammatory plasma proteins, we identified cathepsin S as a lead indicator of liver disease. In contrast lysozyme was a marker of both brain and liver disease. The study was extended on human samples. The level of lysozyme and cathepsin S were determined in the plasma samples from healthy individuals (age and gender matched), untreated NPC patients and Miglustat (also known as Zavesca) treated NPC patients. The plasma lysozyme level was significantly elevated in the untreated NPC samples compared to healthy controls. In the Miglustat-treated NPC samples the lysozyme level reduced compared to untreated NPC patients and were equivalent to healthy controls. Plasma cathepsin S was significantly elevated in untreated NPC patients and was further elevated in the patients treated with Miglustat. The plasma concentration of these two markers in untreated and Miglustat treated NPC samples when analyzed together yielded a composite score to assess extent of neurodegeneration. High lysozyme and low cathepsin S is an indicator of high cerebral and low systemic disease. High lysozyme and high cathepsin S is an indicator of moderate cerebral and high systemic disease. Low lysozyme and high cathepsin S is an indicator of low cerebral and high systemic disease. Low lysozyme and low cathepsin S is an indicator of low/no cerebral and low/no systemic disease. The results are shown in FIGS. 22-25.

Example 4

Assaying Plasma Lysozyme and Cathepsin S Levels in Parkinson and Alzheimer Patients In order to extrapolate the findings in NPC to other neuroinflammatory diseases, we analyzed small number of plasma samples from Parkinson and Alzheimer patients and compared them with age and gender matched controls. Two out of three Parkinson patients showed elevated lysozyme level that is expected for defect in cerebellar activity. Three out of four Alzheimer patients showed increased ratio of cathepsin S and lysozyme. In summary, the composite marker can be used as an index for neurological disease.

The section headings used herein are for organizational purposes only and are not to be construed as limiting the subject matter described in any way.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Example 5

Elevation of Neutrophils and Secretory Granule/Lysosomal Proteins, as Disease Correlates in Mouse Models of Niemann Pick Type C Multiple viral and bacterial infections are attenuated in Niemann Pick Type C (NPC) disease cells and animals, suggesting they may harbor antimicrobial mechanisms even prior to exposure to pathogens. Here we show that whole-genome expression-analyses in the spleen of BALB/c Npc1$^{-/-}$ mice relative to Npc1$^{+/-}$, predicted increased innate immunity across the animal's life-span. Cellularity and immunohistochemistry suggested elevation of neutrophils. Proliferation of the Gram-negative bacterium *Salmonella typhimurium* was reduced by ~one log. Post-infection, neutrophils increased from 7 to 14% in nulls relative to 4 to 7% in heterozygotes. Neutrophils were also increased in liver and lung, unchanged in blood and excluded from the brain of Npc1$^{-/-}$. Nonetheless, brain expression analyses revealed age-dependent elevation of secretory granule/lysosomal components such as lysozyme. This was mimicked in liver, consistent with increased neutrophil granules (which are specialized lysosomes) there. Corresponding elevation of plasma lysozyme was shown to be reduced in response to an emerging therapeutic in BALB/c Npc1$^{nmf164}$ mice bearing an Npc1 point mutation (closer to mutants seen in human disease). These data present the first evidence for neutrophils in disease organs in NPC and suggest widespread age-dependent elevation and secretion of granule/lysosomal proteins that may be explored as surrogates for this lysosomal disease.

Microbial infection is known to co-opt and require genes and pathways essential for health of the host. Recent studies report that the rare, lysosomal disorder Niemann Pick Type C (NPC) disease cells and animals are refractory to infection by multiple viruses and bacteria. NPC cells aberrantly accumulate cholesterol due to defect in one of two late endosomal proteins NPC1 and NPC2, although in 95% of patients disease is caused by defect in NPC1 (Rosenbaum and Maxfield, 2011; Vance and Peake, 2011). Resistance of NPC cells and animals to infection may occur because cholesterol and endosomal trafficking are known to play critical roles in vacuolar infection of virus, bacteria and parasites in a variety of different hosts (Coppens et al., 2000; Gatfield and Pieters, 2000; Samuel et al., 2001; Tang et al., 2009; Watarai et al., 2002). More recently, NPC1 has been shown to act as an invasion receptor for Ebola virus (Carette et al., 2011; Cote et al., 2011), suggesting a direct role for NPC1 independent of cholesterol trafficking in the infection of filoviridae.

We reasoned that since NPC cells are blocked in endo-lysosomal trafficking, mice that are Npc1$^{-/-}$ are likely to show changes in the immune response. Indeed, inflammatory changes are associated with liver, spleen and brain with increased age of NPC animals (Rimkunas et al., 2008; Sayre et al., 2010; Smith et al., 2009; Vazquez et al., 2011) and anti-inflammatory treatments have been shown to reduce disease in mice (Liao et al., 2009; Smith et al., 2009). Further, specific markers have been used to measure the extent of inflammation and its cell type specificity in the brain, as a function of age (Baudry et al., 2003; Smith et al., 2009). However comprehensive analyses of changes in gene expression in major organs known to be affected by disease, as animals transition across the life span, from a phenotypically, asymptomatic state to manifesting major disease symptoms, is not yet available. This would provide insight whether loss of the Npc1 gene influences expression of genes important for host resistance to infection, a condition that can be subsequently validated with a well developed cellular assays, model organisms and other functional read outs.

*Salmonella enterica* serovar *Typhimurium* (*S. typhimurium*), a Gram negative, rod shaped, facultative intracellular bacterial pathogen, is a major cause of food-borne enterocolitis in humans as well as a typhoid-like disease in mice (Haraga et al., 2008; Tsolis et al., 1999). After invasion, the bacteria replicate in a membrane bound compartment called *Salmonella*-containing vacuoles. Due to the ease with which it can be genetically manipulated, quantitatively analyzed both in vitro and in mouse models of infection, *Salmonella* is often used a model system to investigate cellular and organismal processes of mammalian hosts. Replication in the liver and spleen macrophages is essential for dissemination of *Salmonella* (Haraga et al., 2008; Monack et al., 2004). These organs also manifest the earliest pathologies of NPC. However, whether NPC defects influence *salmonella* virulence, and/or proliferation in vivo, is not known.

We have performed comprehensive gene expression profiling analyses to unexpectedly discover an increase of innate immunity transcripts linked to neutrophil and secretory granule functions in spleen, liver and brain, across the life span of the Npc1$^{-/-}$ mouse. Using immunohistochemistry (IHC), cellular analysis and *S. typhimurium* as a model organism, we confirm elevation of innate immunity is due to neutrophils in the spleen. Our data further support elevation of neutrophils in liver and lungs, organs that show significant disease pathologies in NPC. Although neutrophils do not cross the blood brain barrier, transcripts of multiple lysosomal/secretory granule proteins show age dependent increase in the brain. Their age dependent increase was also found in the liver and correlated with neutrophil granules. The lead candidate, lysozyme, was validated in plasma and we therefore propose that lysosomal/granule signatures may yield disease biomarkers.

Results

Elevation of Innate Immune Response Associated with Neutrophils in the Npc1$^{-/-}$ Spleen.

Since the spleen is important for infection of a wide range of microbes, we examined transcripts from this organ in Npc1$^{-/-}$, relative to Npc1$^{+/-}$ mice. Splenomegaly is also amongst the earliest clinical signs of NPC (Vanier, 2010) suggesting there are transcriptional changes in this organ early in the life span, but their nature was completely unknown. To control for inter-animal variability and examine mechanisms consistently observed over an age range from young to adult mice, we examined three pairs of Npc1$^{-/-}$ mutants relative to age-matched Npc1$^{+/-}$ at 20-25 days, 54-55 days and 67-71 days (as indicated in FIG. 9B). This age range covered animals immediately post weaning (20-25 days) through advanced neurodegeneration and weight loss (~30% reduction is observed by 60-80 days), characteristic of this model (Li et al., 2005; Parra et al., 2011). As show in FIG. 1A, Table S1, in the spleen, 227 and 18 transcripts were respectively up- and down-regulated in Npc1$^{-/-}$ animals compared to Npc1$^+$. Of the top 20 up regulated genes (FIG. 28B), five (Clec7a, Atf3, Mmp12, Msr1 and Elane) were found in a well-established innate immunity database (InnateDB, www.innatedb.ca/) (Lynn et al., 2008). Of the remaining 207 up regulated transcripts in the spleen, 25 (such as galectin1&3, cathelicidin, cathepsinB/D, granulin etc) were found to be innate immunity genes (Table S2). Notably, Elane, a serine protease, is a major component of azurophilic granules of neutrophils and targets pathogen virulence factors thereby mediating host defense (Belaaouaj et al., 2000; Belaaouaj et al., 1998; Weinrauch et al., 2002). These results suggested that changes in the innate immune compartment may underlie, at least in part, distinct genetic profiles in Npc1 null versus sufficient animals. We therefore examined the cellularity of CD355$^+$ natural killer (NK) cell, CD11c$^+$ dendritic cells (DC), CD11b$^+$F4/80$^+$ monocytes and macrophages (Mo/MO), and CD11b$^+$Gr-1$^{hi}$ neutrophils in splenic single cell suspensions of Npc1$^{-/-}$ and Npc1$^{+/-}$ animals (FIG. 29A, S2). We selected mice of age at 6-8 weeks, because this was approximately in the middle of the age range of animals examined in our microarray studies. Flow cytometric analysis showed no effect on cellularity of NK cell or dendritic cells. Further, while the total cellularity of CD11b$^+$F4/80$^+$ Mo/MO was unaffected (~57×10$^5$ in Npc1$^{+/-}$ versus ~53× 10$^5$ in Npc1$^{-/-}$), Npc1$^{-/-}$ animals showed decreased cellularity of CD11b$^{lo}$F4/80$^{hi}$ Mo/MO as compared to Npc1$^{+/-}$ controls, ~12×10$^5$ versus ~32×10$^5$, respectively, p<0.0005 and increased cellularity of CD11b$^{hi}$F4/80$^{lo}$ Mo/MO as compared to Npc1$^{+/-}$ controls, ~41×10$^5$ versus ~25×10$^5$, respectively, p<0.001. Importantly, CD11b$^+$Gr-1$^{hi}$ neutrophils were significantly increased in Npc1$^{-/-}$ animals, ~90× 10$^5$ versus ~34×10$^5$, respectively, p<0.0005. The increased cellularity in neutrophils is consistent with the innate immune cell footprint observed in microarray. We functionally validated neutrophils accumulation by IHC, using spleen from Npc1$^{-/-}$ and Npc1$^{+/-}$ littermates aged 48-52 days, which is an intermediate time point in the life span As shown in FIG. 2B neutrophils (Gr-1$^+$ cells stained in brown) were primarily observed in the marginal zone and in the red pulp of the spleen in both Npc1$^{+/-}$ and Npc1$^{-/-}$ mice. However, a massive accumulation of neutrophils was seen in the red pulp of Npc1$^{-/-}$ mouse (FIG. 29B, panel B3-4) compared to Npc1$^{+/-}$ mouse (FIG. 29B, panel B1-2).

To test whether this increased cellularity in neutrophils seen in FIGS. 2A&B was functionally active in Npc1$^{-/-}$ spleens, we infected mice with *S. typhimurium* whose proliferation is known to be significantly inhibited by neutrophils (Vassiloyanakopoulos et al., 1998). Since we wanted to directly assess bacterial proliferation in the spleen (and bypass the gut) the animals were infected through intraperitoneal (i.p) route and bacterial load in spleen was determined at 48 hours post infection (hpi) by measuring colony forming units (see Materials and Methods). As shown in FIG. 2C, we found comparable bacterial loads in Npc1$^{+/+}$ and Npc1$^{+/-}$ mice. However, there was ~8-10 fold reduction in bacterial load in spleen of Npc1$^{-/-}$ mice. Further, cellular analyses of spleens after *S. typhimurium* infection (FIG. 29D) indicated that the levels of NK cells was unchanged, CD11b$^{lo}$F4/80$^{hi}$ Mo/MO decreased and CD11c$^{+}$ dendritic cells increased to the some extent in Npc1$^{-/-}$ versus Npc1$^{+/-}$ mice. Importantly, CD11b$^{+}$Gr-1$^{hi}$ neutrophils were greatly increased in Npc1$^{-/-}$ compared to Npc1$^{+/-}$, ~167×10$^5$ versus ~74×10$^5$, p<0.000001 (FIG. 29D, S3). The reduced bacterial proliferation seen in Npc1$^{-/-}$ spleen is well explained by the fact that as much as ~14% cells were neutrophils compared to only ~7% in Npc1$^{+/-}$. Together, these data suggest an increased innate immunity associated with neutrophils in the Npc1$^{-/-}$ spleen.

Elevation of Neutrophils in the Liver of Npc1$^{-/-}$ Mice

As with the spleen, enlargement of liver is an early indication of NPC disease. We therefore examined whether neutrophils were also elevated in the liver. Prior data in the literature has suggested accumulation of foamy macrophages in liver but neutrophils have not been studied. (Beltroy et al., 2005; Rimkunas et al., 2008; Sayre et al., 2010). In the liver, we began with examining three pairs of Npc1$^{-/-}$ mutants relative to age-matched Npc1$^{+/-}$ at 20-25 days, 54-55 days and 67-71 days (FIG. 9B). As shown in FIG. 30A, 1644 transcripts showed consistent change through these age groups in Npc1$^{-/-}$ mice. 964 were reliably up regulated and 680 were down regulated in the liver (Table S3). Changes in gene expression seen in the top 20 genes were relatively large in the range of ~80 to 15 fold. (FIG. 30B). Eleven (marked in bold) are reported to have roles in innate immunity and/or antimicrobial activity against viruses, bacteria and/or fungi. Mmp12, Lgals3, Clec4d, Clec7a, Camp, Slamf7 and Bcl2a1 are incorporated in InnateDB, (www.innatedb.ca/) (Lynn et al., 2008). Four additional innate immunity determinants include Gpnmb, Il7r, Pou3f1/Oct 6 and Capg (Hofmann et al., 2010; Jiang et al., 2005; Kasten et al., 2010; Li et al., 2010; Parikh et al., 2003). In the remaining 948, we detect an additional 77 genes (Table S4) that are found in Innate DB and include several cathepsins (cathepsinb/d/s) that are known to be harmful to intracellular pathogens. This is also true of several important, innate immunity genes shared between liver and spleen. For example Mmp12 up regulated ~80 fold in liver and ~8 fold in spleen appears to be a macrophage specific antimicrobial protease. However, Camp (cathelicidin) up regulated ~21 fold in liver is primarily expressed by neutrophils and play direct role in killing of *S. typhimurium* (Houghton et al., 2009; Rosenberger et al., 2004). Another molecule of interest was Clec7a (also known as Galectin1 or Dectin1) which was up regulated ~21 fold in liver and ~9 fold spleen. It is a pathogen recognition receptor, important in host defense against fungal infections (Drummond and Brown, 2011; Reid et al., 2009), that is expressed by both macrophages and neutrophils. In addition, we find neutrophil-specific genes such as Ncf4 (neutrophil cytoplasmic factor 4) was increased ~7 fold in the liver (FIG. 30C) along with its interacting proteins Ncf2 and Cyba (cytochrome b-245, alpha polypeptide, also known as p22phox). In summary, the expression data suggested that along with macrophages, neutrophils may also be increased in the liver of Npc1$^{-/-}$ mice. We therefore employed IHC to determine neutrophil prevalence in the liver of Npc1$^{+/-}$ and Npc1$^{-/-}$ mice (age 48-52 days). As shown in FIG. 30D, (panel D3-4), giant foci of neutrophils (Gr-1$^{+}$ cells stained in brown) were seen in the liver of Npc1$^{-/-}$ mouse, compared to the liver of Npc1$^{+/-}$ mouse (panel D1-2). Notably, damage to liver tissue was in the region of neutrophil accumulation were seen in Npc1$^{-/-}$ mice.

Consistently, infection by *S. typhimurium* was blocked ~8-10 fold in the liver of Npc1$^{-/-}$ mice, (FIG. 30E) analogous to the spleen. Thus, expression analyses, immunohistochemical analyses and close correspondence between the extent of inhibition of bacterial infection seen in liver and spleen, strongly support mechanisms of innate immunity due to neutrophils are likely to also be active in the liver of Npc1$^{-/-}$ animals. The expression data revealed that as many as 63 genes were associated with neutrophil granules, of which 21 were secretory proteins (Table S5). Importantly, the transcripts of antimicrobial proteins e.g. cathelicidin, defensin, lysozymes, cathepsins etc were among the highly up regulated transcripts in the liver of Npc1$^{-/-}$ mice.

Examination of Neutrophils in Lung, Blood and Brain

In addition to the liver and spleen, profound changes linked to NPC disease are also seen in the lung and brain (Manabe et al., 1995; Rosenbaum and Maxfield, 2011). IHC did in fact suggest higher infiltration of neutrophils in the alveolar septa of the lungs of Npc1$^{-/-}$ mouse (FIG. 31A, panel A3-4) but up to a lesser degree in Npc1 mouse (FIG. 31A, panel A1-2). Neutrophils were not found in the alveolar cavities of the lungs in either Npc1$^{-/-}$ or Npc1$^{+/-}$ mice. Although autopsies are rarely undertaken in humans to analyze diseased organs, standard blood work up is carried out in patients and does not reveal notable cellular abnormalities. Our analysis of mouse blood likewise revealed that cellular parameters in both Npc1$^{-/-}$ and Npc1$^{+/-}$ remained in the normal range (FIG. 31B). Notably, there was no significant change in either circulating neutrophils or macrophages in the blood (FIG. 31B). However neutrophil granule proteins from liver may well be released and elevated in the plasma (as revealed later in this study). Finally, IHC was carried out to study the presence of neutrophils (Gr-1$^{+}$ cells) in brain of Npc1$^{-/-}$ mice (age 48-52 days). Neutrophils remained undetected, despite scanning the entire sagittal section of brain.

The results shown in FIG. 32 present representative images from the cerebellum and mid brain regions from Npc1$^{-/-}$ (panel A1 and A3, respectively) and Npc1$^{-/-}$ (panel A4 and A6, respectively). As expected, significant loss of purkinje cells was observed in the cerebellum of Npc1$^{-/-}$ mouse (FIG. 32, panel 5).

Elevation in Innate Immunity Transcripts in Brain of Npc1$^{-/-}$ Mice

Progressive neurological dysfunction is a prominent feature of NPC disease, and hence understanding correlates in the brain is of critical importance to understanding disease progression. To comprehensively cover the life span, we examined transcripts in brain from animals immediately after weaning (20-25 days) to those at terminal stages of disease (80-84 days) (FIG. 9A). Across this range, five time points were utilized to closely map the life span of Npc1$^{-/-}$ mice. For each point, transcripts of brains from two Npc1$^{-/-}$ mice were compared to age matched, Npc1$^{+/-}$ mice. Npc1$^{+/+}$ animals were also included in two time points (as outlined in FIG. 9A) to enable comparative analysis across all three genotypes. Examination of brain transcripts up regulated in Npc1$^{-/-}$ mice relative to Npc1$^{+/-}$ mice across all time points, revealed change in 188 genes, with elevation in 117 and decrease in 71 (Table S6). Remarkably, of the top 5 genes up regulated (FIG. 33A), four are annotated to be Lysozyme1, Clec7A, Lysozyme2, Gp49a and all play a role in mechanisms of innate immunity (Drummond and Brown, 2011; Lee et al., 2000; Nakatsuji and Gallo, 2011). Lysozyme1 showed the greatest increase with ~12 fold elevation. Lysozyme and Clec7a are associated with granules and plasma membrane of many cells (including macrophages), while GP49a associates with immunoglobulin superfamily receptors present on mast cells. InnateDB suggest a total of 27 up regulated genes associated with innate immunity (Table S7). Other up regulated innate immunity transcripts were found to be associated with major histocompatibility complex (H2-d1, H2-k1, H2-1 and H2-t3), Fc receptors (Fcgr2b, Fcgr3, Fcer1g and Fcrls), complement system (C1qa, C1qb, C1qc, C4b, and C3ar1), cathepsins, (Ctsb, Ctsd. Ctss and Ctsz), galactose binding lectins (Lgals1, Lgals3, Lgals9 and Lgals3 bp), interferon induced proteins (Ifit1, Ifit3, Ifitm2, Ifitm3, Ifi35, Ifi44 and Ifi2712a), macrophage/microglia (Mpeg1, CD688), integrins (Itgax, Itgb2) etc. Of the five most down regulated genes, only one (diminished ten-fold) was annotated as major urinary protein (MUP).

These data suggest that although neutrophils do not penetrate the brain, anti microbial lysosomal secretory proteins seen in neutrophils granules (such as lysozymes, cathepsins etc), are elevated in the brain. Although we did not determine the exact source of over expression of lysozyme and other markers, a likely source may be microglia and/or astrocytes that have been shown to be activated in brain (Pressey et al., 2012). Since lysozyme is expressed in variety of cells, additional sources cannot be ruled out. Nonetheless, there is concomitant elevation in lysozyme transcripts in brain and the liver (FIG. 33B). Further, out of 51 transcripts of up regulated secretory proteins seen in the brain, 26 were also over expressed in the liver (Table I) of which 14 are stored in neutrophils granules (Table I, shaded in gray). Since the liver is a major source of secretory proteins in blood, this suggested that a subset of secretory proteins in the liver may function as biomarkers of disease in the brain.

Elevated Lysozyme Activity in the Plasma of $Npc1^{-/-}$ Mice

There is as yet, no blood-based biomarker for NPC and this greatly delays diagnosis of the disease, which can take on average of five years (Porter et al., 2010; Wraith et al., 2009; Yanjanin et al., 2010). Recent studies suggest that elevation of oxysterols in plasma could well be developed into the first blood-based diagnostic for NPC (Porter et al., 2010). However, although $Npc1^{-/-}$ show the highest elevation, oxysterols are also slightly increased in $Npc1^{+/-}$ animals. Further, Oxysterols may not respond to substrate reduction therapies such as miglustat (Zavesca) that reduces levels of sphingolipids rather than cholesterol (Patterson et al., 2007), suggesting multiple biomarkers will be required. In order to test whether neutrophils granule proteins in liver are elevated in the plasma, we selected lysozyme, a small, stable soluble protein as a candidate molecule. Furthermore, lysozyme transcripts are also elevated in the brain. Indeed lysozyme transcripts in both liver and brain show age-dependent elevation (FIG. 33B), suggesting it may be an appropriate disease correlate. Our interest was to determine whether lysozyme protein and/or enzymatic activity were elevated in blood of $Npc1^{-/-}$. To facilitate rapid quantification, we pursued lysozyme's well defined muramidase activity in a blood plasma assay. As shown in FIG. 4, levels of active lysozyme were indeed elevated in $Npc1^{-/-}$ mice 3-4 weeks old (representing 21-28 days at weaning and soon after) relative to age $-/-$ matched, $Npc1^{+/+}$ and $Npc1^{+/-}$. Further, plasma from $Npc1^{-/-}$ mice showed progressively increased lysozyme activity reaching a peak at 7-8 week of age. At 9-10 weeks (most animals die by 11 weeks in $Npc1^{nih}$ model), lysozyme levels may plateau. The data shown in FIG. 4 is derived from both male and female animals, suggesting age dependent elevation of lysozyme was independent of gender. The assay could be carried out using 2 to 20 ul of plasma, suggesting it is sensitive and has a large dynamic range.

Elevation of Lysozyme in BALB/c $Npc1^{nmf164}$ Mice and its Reduction in Response to Treatment with Cyclodextrin, an Emerging Therapeutic.

Although the Npc1 null mouse captures the progression of human disease, most patients show point mutations rather than a truncation in the gene. We therefore examined the BALB/c $Npc1^{nmf164}$ ($Npc1^{nmf}$) mouse with milder disease progression due to a single point mutation (D1005G) in the cysteine rich domain of the protein, which is the most common region for human mutations. Previous studies suggest that $Npc1^{nmf}$ in the C57BL/6J background have a life span of ~112 days and develop progressive disease (Maue et al., 2012). They show delayed weight loss starting from 9-10 weeks and the rate was slower than the $Npc1^{nih}$ mice. Histological analyses on liver, spleen and brain showed abnormal cholesterol accumulation, and purkinje cell loss at a slower rate than the $Npc1^{nih}$ (Maue et al., 2012). We find that BALB/c $Npc1^{nmf}$ have a similar life span (~120-125 days) and disease progression to that of C57BL/6J $Npc1^{nmf164}$ mice. Typically they exhibited weight loss from 12 weeks and by the end of 16 weeks ~15-20% weight loss was observed (FIG. 34A).

As shown in FIG. 7B, levels of active lysozyme were indeed elevated in $Npc1^{nmf}$ mice 3-4 weeks old (representing 21-28 days at weaning and soon after) relative to age matched, controls. Further, plasma from $Npc1^{nmf}$ mice also showed progressively increased lysozyme activity reaching a peak at 10-11 week of age. At 14-15 weeks (most animals die by 17-18 weeks in this model), lysozyme levels may plateau. The data shown in FIG. 7B is derived from both male and female animals, suggesting that elevation in lysozyme may be useful correlate for disease, especially at the early phases, when diagnosis is difficult but needed. With the emergence of new therapeutics for NPC, there is urgent need for correlates whose levels mirror improvement of disease course as a consequence of treatment. Cyclodextrin has emerged as the most effective compound at retarding NPC disease in mice (Rosenbaum and Maxfield, 2011). Previous studies suggest that weekly injections of HPβCD (2-hydroxypropyl-beta-cyclodextrin) to $Npc1^{nih}$ (a BALB/c strain) ameliorates the disease and extend the survival (Davidson et al., 2009; Ramirez et al., 2010). Similarly, weekly injections of HPβCD to $Npc1^{pf/pf}$ mice (a knockin BALB/c strain carrying point mutations resulting in failure to cholesterol binding and manifestation of NPC disease) also show improvement in disease status (Xie et al., 2011). We therefore treated $Npc1^{nmf}Npc1^{-/-}$ mice with HPβCD or vehicle control (0.2% DMSO in 0.9% saline) with once a week drug injections starting at age 21-27 days. At 50-55 days, untreated $Npc1^{-/-}$ mice had ~1.4-1.8 fold higher plasma lysozyme activity compared to $Npc1^{+/+}$ or $Npc1^{+/-}$ (age 42-49 days). The plasma lysozyme activity of the vehicle treated $Npc1^{-/-}$ mice remained elevated (comparable to $Npc1^{-/-}$ untreated) however in $Npc1^{-/-}$ mice treated with HPβCD, it was significantly reduced (FIG. 34C). Thus, lysozyme may be an early disease correlate that measures early responsiveness to a drug.

Together, the data presented here suggest that secretory granule/lysosomal proteins like lysozyme alone (or combined with others) could provide useful surrogate disease markers. These markers may be responsive to emerging drug like cyclodextrin, especially for early and mid-stage disease when phenotypic symptoms are not evident/prominent and thus surrogate markers are urgently needed.

Discussion

Despite significant advances in understanding lysosomal lipid trafficking defects and pathogenesis of NPC disease, the immunological consequences of this syndrome are only just emerging. Prior work has demonstrated that antisense mediated knock down of Npc1 in C57BL/6 mice results in tumor necrosis factor α (TNF-α)-dependent accumulation of inflammatory cells in liver (Rimkunas et al., 2008; Rimkunas et al., 2009). Accumulation of foamy macrophages in liver (Beltroy et al., 2005; Rimkunas et al., 2008; Sayre et al., 2010) and activation of microglia (Pressey et al., 2012) in brain has been reported for NPC null mice. Impaired development and reduced natural killer T (NKT) cells in spleen and thymus of NPC diseased mice has also been reported (Sagiv et al., 2006; Schrantz et al., 2007). Changes in inflammatory markers have been reported (Baudry et al., 2003; Rimkunas et al., 2009; Smith et al., 2009) consistent with organ specific (largely the brain) analysis of transcripts (Liao et al., 2010; Lopez et al., 2012; Vazquez et al., 2011). Expression arrays have also been utilized to investigate transcriptional changes in cell culture (De Windt et al., 2007; Reddy et al., 2006). However, comprehensive changes in NPC spleen, liver and brain have not been systematically examined through the life span of the mouse. Further, over all cellularity in liver and spleen, two organs that are affected early in NPC remained unknown. Our examination of transcriptional changes seen from freshly weaned animals to late in neurodegeneration, enabled prediction of innate immunity trends that could not be obtained from single or a few time points in isolated organ systems. This approach provided rationale for functional infection studies as well as comprehensive analysis of innate immune cells in the spleen of $Npc1^{-/-}$ mice, both before and after bacterial infection and thus established for the first time, that defect in NPC1 leads to increased infiltration of neutrophils in the spleen.

Neutrophils or polymorphonuclear lymphocytes (PMNLs) are essential innate immune cells, and the host's first line of defense against various bacterial and fungal infections. They are laden with various cytotoxic granules enriched with different powerful antimicrobial molecules such as cationic peptides, proteases, lactoferrin, myeloperoxidase etc (Kumar and Sharma, 2010; Segal, 2005). They undergo respiratory burst and produce reactive oxygen intermediates to target the microbial pathogen (Nathan, 2006; Segal, 2005). In addition to microbial killing, granule components also mediate cell to cell interaction, adhesion and extravasation. Elevated neutrophils in spleen, liver (and lungs) of $Npc1^{-/-}$ mice could be attributed due to increased chemoattraction and extravasation, without steady state elevation in blood. The over expression of matrix metalloproteases, galectins, integrins, phygocyte oxidase, adhesins etc in spleen and/or liver of $Npc1^{-/-}$ mice supports enhanced neutrophils migration to these organs.

Though, we did not carry out cellular analysis on liver, in addition to neutrophils, large 'foamy' macrophages are readily detected in sections through NPC liver (data not shown) and undoubtedly contribute to an inflammatory response, as has been previously reported (Beltroy et al., 2005; Rimkunas et al., 2008). Indeed recent studies suggest that removal of macrophages by Ccl3 deletion aggravates the NPC disease (Lopez et al., 2012), suggesting macrophages may be protective in NPC. It should be noted that although neutrophils are required to resolve the inflammation, their sustained activation, degranulation and release of cytotoxic molecules leads to tissue injury (Mantovani et al 2011). Indeed, neutrophil apoptosis followed by their phagocytosis by macrophages is an essential mechanism for regulating neutrophil functions and is an important control point in the development and resolution of inflammation (El Kebir & Filep 2010; Silva 2011). Neutrophil number is apparently not compromised in Ccl3 mutant mouse (Ajuebor et al., 2004). In the absence of macrophage function, the tissue would be exposed to cytoxic molecules released from apoptotic neutrophils and may thereby aggravate the injury. Future studies directed towards understanding the neutrophils function in the Ccl3/Npc1 double knockout mouse may provide a better understanding of neutrophil and macrophage involvement in NPC disease.

We see age-dependent elevation of secretory granule/lysosomal proteins in the brain, as well as other organs, suggesting elevation of these proteins, possibly in a systemic way in many different cell types, even in the absence of neutrophils. The most likely reason is that NPC1 is a lysosomal protein and thus its loss induces a compensatory response in other lysosomal components. Consistently, over expression of some of these proteins such as Cathepsin B and Cathepsin D has also been reported in the brain of murine models of several other lysosomal diseases such as Gaucher's disease, Sandhoff disease, GM1 gangliosidoses, Neimann-Pick A etc. (Myerowitz et al., 2002; Vitner et al., 2010). In addition to innate immune markers, we also see elevation of transcripts of alpha-N-acetylglucosaminidase (Naglu) and HexosaminidaseB (HexB), genes linked to lysosomal diseases MPS IIIB and Sandhoff disease respectively. Concomitant, age-dependent elevation of the same proteins in neutrophils granules (which are highly specialized lysosomes) as well as macrophages in the liver, provides a rational basis for their selection as candidate biomarkers, since most proteins in plasma are produced in the liver.

Lysozyme was selected for validation in plasma because it was maximally elevated in the brain, was also over expressed in liver and secretory in nature. It is also a small, stable protein present in blood as well as additional secretions like saliva and thus particularly suited to being developed as a biomarker. Elevation of lysozyme in both $Npc1^{nih}$ and $Npc1^{nmf}$ mice strongly suggest that lysosome/secretory granule protein markers may be associated with both severe and milder disease progression. The responsiveness of lysozyme to cyclodextrin demonstrates the first use of a plasma marker in NPC disease (in either mouse or humans). Curiously, although transcript levels of lysozyme continue to increase with age in both brain and liver, the enzymatic activity of lysozyme plateaus at later stages in both the $Npc1^{nih}$ and $Npc1^{nmf}$ models. The reasons have yet to be explored. One possibility is that as the disease becomes severe, lysozyme protein denatures and loses its activity due to prolonged oxidative stress (Vazquez et al., 2011).

Future studies will focus on determining presence of lysozyme and other lysosomal/secretory proteins as disease markers in human NPC patients as well as other lysosomal disorders. One early report suggests a modest increase in plasma lysozyme in four adult patients with Gaucher's disease (Silverstein and Friedland, 1977). Elevated lysozyme transcripts and protein have been found in neuronal cells in the brain of another lysosomal disorder San Fillipo IIIB (MPS IIIB) mouse model (DiRosario et al., 2009; Ohmi et al., 2009). A linkage between lysozyme and hyperphosphoylated tau has been suggested in the MPS111B mouse brain (Ohmi et al., 2009). At high concentration, lysozyme on its own is known to be amyloidogenic (Trexler and Nilsson, 2007) and exposure of cultured rat neurons to oligomer of hen egg white lysozyme had been found to induce hyperphosphorylation of tau (Vieira et al., 2007). Thus, in addition to serving as secretory markers, lysozyme and other secreted lysosomal/granule proteins expressed in glial and neuronal (and possibly endothelial) cells in the brain, may also exacerbate neurological disease.

Materials and Methods

Materials

All fine chemicals and antibiotics were obtained from Sigma (St Louis, Mo., USA), unless otherwise indicated. Anti mouse F4/80-FITC antibody (clone CI:A31) was from Abd Serotec (Raleigh, N.C., USA). Anti mouse CD335-FITC (clone 29A1.4), CD11c-FITC (clone N418), CD11b-PE (clone M1/70), and Gr-1-APC (clone RB6-8C5) were procured from eBioscience (San Diego, Calif., USA). For IHC unlabeled rat anti-mouse Gr-1 (clone RB6-8C5, eBioscience) was used to detect neutrophils.

Production of $Npc1^{nih}$ and $Npc1^{nmf164}$ Mutant Mice

The $Npc1^{nih}$ is the regular NPC BALB/c strain (Loftus et al., 1997), carrying a truncation and premature translation of NPC1 protein was purchased from JAX labs and was originally obtained from Peter Penchev at the National Institutes of Health (Bethesda, Md., USA). $Npc1^{nmf164}$ is a BALB/c strain and is similar to recently described $Npc1^{nmf164}$ in C57BL/6J (Maue et al., 2012). This strain shows a slower i disease progression. $Npc1^{nmf164}$ strain s an ethyl-nitroso urea-induced point mutation in the Npc1 gene and was originally discovered in C57BL/6J. Later the mutation was transferred to BALB/c strain by Robert P. Erickson, University of Arizona Health Sciences Center, Tucson, Ariz., USA. There is a single nucleotide change (A to G at cDNA bp 3163) resulting in an aspartate to glycine change at position 1005 (D1005G). Homozygous mutant of both strains ($Npc1^{-/-}$) along with wild type littermates ($Npc1^{+/+}$), were generated by crossing heterozygous mutant ($Npc1^{+/-}$) males and females in-house. $Npc1^{nih}$ Mouse pups were genotyped according to published protocols (Loftus et al., 1997) whereas $Npc1^{nmf164}$ mice were genotyped based on PCR followed by digestion with BstEII as described elsewhere (Maue et al., 2012). Throughout, the studies, we used $Npc1^{nih}$ mice unless otherwise indicated.

Microarrays and Expression Analyses

Spleen and liver from 6 $Npc1^{-/-}$ and 6 $Npc1^{+/-}$ female mice age ranging from 20-71 days (see FIG. 9B for details) and brain from 11 $Npc1^{-/-}$ and 16 control female mice ($Npc1^{+/+}$ and $Npc1^{+/-}$) age ranging from 20-84 days (see FIG. 9A for details) were surgically harvested, kept in RNA later and stored at −20° C. until used. RNA was isolated using Roche MagNa Pure Compact automated system and labeling was done using MessageAmp™ Premier RNA Amplification Kit (Invitrogen). Affymetrix mouse 430 2.0 array hybridizations were performed by 'UCLA Clinical Microarray Core', UCLA, Los Angeles, Calif., USA, following standard Affymetrix GeneChip Expression Analysis protocol. The acquisition of array image was undertaken by using Affymetrix GeneChip Command Console 1.1 (AGCC). Subsequent raw data were analyzed using DNA-Chip Analyzer (D-Chip) with the .CEL files obtained from AGCC. We used a PM/MM difference model for estimating gene expression level and quantile approach for data normalization. Thresholds for selecting significant genes were set at a relative difference≥1.5-fold, absolute difference 100 signal intensity units and p<0.05. Genes met all three criteria simultaneously were considered as significant change.

Identification of Secretory Granule Proteins of Neutrophil

In order to find out the granule proteins of neutrophils published literature were searched (Jethwaney et al., 2007; Lominadze et al., 2005; Mollinedo, 2003) and the gene list was prepared for the genes whose transcripts were found to be up regulated in liver. SignalP 4.0 server (www.cbs.dtu.dk/services/SignalP/) was used to identify the signal sequence. Proteins containing N-terminal signal sequence were considered secretory.

In Vivo Infection of Mice

*Salmonella enterica* serovar *typhimurium* SL1344 was grown in Luria-Bertani (LB) broth containing streptomycin sulfate (50 µg/ml). Female littermate $Npc1^{+/+}$, $Npc1^{+/-}$ and $Npc1^{-/-}$ mice (age 6-8 weeks) were used for the *S. typhimurium* infection. Bacteria from overnight cultures were pelleted by centrifugation for 5 min at 6000 rpm and were re-suspended in PBS. Mice were given $1×10^4$ bacteria in 100 µl by i.p injection. Serial dilutions of inoculants were plated on selective media to determine the actual doses. At 48 hpi, mice were sacrificed. Spleen and liver were isolated, weighed, homogenized, serial dilutions were made and plated on selective media to determine the number of bacterial colony forming units (CFU).

Flow Cytometry

To enumerate the numbers different immune cells in spleen, females $Npc1^{+/+}$ and $Npc1^{-/-}$ littermates (6-8 weeks) were used. Spleen was harvested and splenocytes were prepared as per standard procedure. Cells were counted using hemocytometer. *S. typhimurium* infection to mice were performed as described above and splenocytes were prepared at 48 hpi. For flow cytometry, $10^5$ cells were blocked using heat inactivated 10% normal mouse serum and 1% BSA in PBS for 30 min. Cells were stained with flurophore conjugated antibodies against CD335 (FITC) for NK cells, CD11c (FITC) for dendritic cells (DC), F4/80 (FITC) for macrophages, CD11b (PE) and Gr-1 (APC) for neutrophils. Cells positive for both F4/80 and CD11b were considered monocytes/macrophages whereas cells positive for CD11b and had high Gr-1 expression were considered neutrophils. Depending on requirements and fluorophore compatibility splenocytes were stained either separately or in combinations. Suitable isotype control for each antibody was included as controls and compensation was performed wherever required. $10^5$ events were typically recorded in Beckman Coulter FC500 flow cytometer.

Organ Harvest and Immunohistochemistry

Female littermate $Npc1^{+/-}$ and $Npc1^{-/-}$ mice (age 48-52 days) were sacrificed by $CO_2$ asphyxiation. The circulatory bed was washed with PBS (pH 7.4), followed by the perfusion with 10% neutral buffered formalin (~4% formaldehyde). The organs (brain, liver, lung and spleen) were surgically harvested and stored in 4% formaldehyde at room temperature (RT) until inclusion in the paraffin. Formalin paraffin-embedded tissue sections (3-4 µm) were dewaxed in xylene and alcohol. Antigen retrieval was done by pre-incubation of deparaffinized samples with 0.05% proteinase K (Dako, Germany) in 50 mM Tris-HCl (pH 7.5) for 8 min at RT. After washing, sections were immersed in 3% $H_2O_2$ in distilled water for 20 min at RT to block endogenous peroxidase. After an additional wash with PBS, the sections were treated with 5% rabbit serum for 30 min, followed by successive incubation in avidin and biotin (Avidin/biotin blocking kit, Vector Laboratories) to block endogenous biotin. Anti-mouse Gr-1 (5 µg/ml in PBS with 2% rabbit serum) was applied to the sections for 60 min at RT. Secondary antibodies was biotinylated rabbit anti-rat IgG (mouse absorbed, Vector Laboratories). Reagents were prepared according to the manufacturer's recommendation. The peroxidase complexes were revealed by incubation with 3,3'-diaminobenzidine-tetra-hydrochloride (DAB, Vector Laboratories) and the sections were lightly counterstained with Mayer's hemalum. The slides were then mounted in cytoseal XYL (Thermo Scientific, Kalamazoo, USA). Sections stained only with secondary antibodies served as controls. Pictures were acquired on a Nikon Olympus microscope, using a Nikon digital DS-Fi1-U2 camera controlled by NIS-Elements F3.0 Nikon software (all from Nikon Instruments INC, Tokyo, Japan). Images were visualized with A10 PL 10×/0.25, or a DPIan Apo 40×/1.00 oil-immersion or a DPIan Apo 100×/1.30 oil-immersion objective lens (Nikon).

Lysozyme Activity Assay in Plasma

Lysozyme activity in the plasma of $Npc1^{+/+}$, $Npc1^{+/-}$ and $Npc1^{-/-}$ mice was measured using fluorescence based lysozyme assay kit (EnzCheck, Molecular Probes, Grand Island, N.Y., USA). The assay measures the lysozyme activity on *Micrococcus lysodeikticus* cell walls, which are labeled to such a degree that the fluorescence is quenched. Lysozyme action relieves this quenching; yielding an increase in fluorescence that is proportional to lysozyme activity. Plasma from both female and male $Npc1^{nih}$ mice corresponding to 50-500 µg protein (~2 to 10 µl in volume) was used in a 100 µl reaction volume. The reaction was carried out either at 37° C. for 1 h (when 500 µg plasma protein was used) or at 37° C. for 24 h (when 50 µg plasma protein was used). For $Npc1^{nmf164}$ mice, we used 50 µg plasma protein and the reaction mixture was incubated at 37° C. for 24 h. Fluorescence was read using excitation/emission of 494/518 nm in a multiwall plate reader spectramax M2 (Molecular devices, CA, USA). The values obtained were normalized to 1 by dividing the numbers by the maximum value of lysozyme obtained among $Npc1^{+/-}$ mice. Purified chicken egg white lysozyme was used as a positive control.

Drug Injections and Blood Withdrawal

Starting at P21-27 and once a week thereafter, $Npc1^{nmf164}$ homozygous mutant female mice were injected i.p with 20% 2-hydroxypropyl-beta-cyclodextrin (HPβCD, 4000 mg/Kg) prepared in 0.2% DMSO and 0.9% saline. Control mice received 0.2% DMSO in 0.9% saline. Blood via cheek bleed was collected from mice, age 50-55 days from both treatment groups in EDTA tubes (BD, CA). Plasma was separated by centrifugation at 2500 rpm for 15 min and stored at −70° C. until used. Blood was collected either through cardiac puncture or cheek bleed. Plasma was isolated by centrifugation at 2500 rpm for 15 min at RT and stored at −70° C. until used. For hematology analyses, 20 µl blood was collected in a microfuge tube coated and dried with 20 µl of 1.25 mg/ml EDTA. Blood cell parameters were analyzed by Hemavet 950 (Drew Scientific, Dallas).

Miscellaneous

All animal experiments were performed with the approval and authorization from the 'Institutional Review Board' and the 'Animal Care and Use Committee', University of Notre Dame. Student's t test was carried out to determine the statistical significance of the data. P<0.05 considered significant.

LITERATURE CITED

Ajuebor, M. N., C. M. Hogaboam, T. Le, A. E. Proudfoot, and M. G. Swain. 2004. CCL3/MIP-1alpha is pro-inflammatory in murine T cell-mediated hepatitis by recruiting CCR1-expressing CD4(+) T cells to the liver. *Eur J Immunol* 34:2907-2918.

Baudry, M., Y. Yao, D. Simmons, J. Liu, and X. Bi. 2003. Postnatal development of inflammation in a murine model of Niemann-Pick type C disease: immunohistochemical observations of microglia and astroglia. *Exp Neurol* 184: 887-903.

Belaaouaj, A., K. S. Kim, and S. D. Shapiro. 2000. Degradation of outer membrane protein A in *Escherichia coli* killing by neutrophil elastase. *Science* 289:1185-1188.

Belaaouaj, A., R. McCarthy, M. Baumann, Z. Gao, T. J. Ley, S. N. Abraham, and S. D. Shapiro. 1998. Mice lacking neutrophil elastase reveal impaired host defense against gram negative bacterial sepsis. *Nat Med* 4:615-618.

Beltroy, E. P., J. A. Richardson, J. D. Horton, S. D. Turley, and J. M. Dietschy. 2005. Cholesterol accumulation and liver cell death in mice with Niemann-Pick type C disease. *Hepatology* 42:886-893.

Carette, J. E., M. Raaben, A. C. Wong, A. S. Herbert, G. Obernosterer, N. Mulherkar, A. I. Kuehne, P. J. Kranzusch, A. M. Griffin, G. Ruthel, P. Dal Cin, J. M. Dye, S. P. Whelan, K. Chandran, and T. R. Brummelkamp. 2011. Ebola virus entry requires the cholesterol transporter Niemann-Pick C1. *Nature* 477:340-343.

Coppens, I., A. P. Sinai, and K. A. Joiner. 2000. *Toxoplasma gondii* exploits host low-density lipoprotein receptor-mediated endocytosis for cholesterol acquisition. *J Cell Biol* 149:167-180.

Cote, M., J. Misasi, T. Ren, A. Bruchez, K. Lee, C. M. Filone, L. Hensley, Q. Li, D. Ory, K. Chandran, and J. Cunningham. 2011. Small molecule inhibitors reveal Niemann-Pick C1 is essential for Ebola virus infection. *Nature* 477:344-348.

Davidson, C. D., N. F. Ali, M. C. Micsenyi, G. Stephney, S. Renault, K. Dobrenis, D. S. Ory, M. T. Vanier, and S. U. Walkley. 2009. Chronic cyclodextrin treatment of murine Niemann-Pick C disease ameliorates neuronal cholesterol and glycosphingolipid storage and disease progression. *PLoS One* 4:e6951.

De Windt, A., M. Rai, L. Kytomaki, K. M. Thelen, D. Lutjohann, L. Bernier, J. Davignon, J. Soini, M. Pandolfo, and R. Laaksonen. 2007. Gene set enrichment analyses revealed several affected pathways in Niemann-pick disease type C fibroblasts. *DNA Cell Biol* 26:665-671.

DiRosario, J., E. Divers, C. Wang, J. Etter, A. Charrier, P. Jukkola, H. Auer, V. Best, D. L. Newsom, D. M. McCarty, and H. Fu. 2009. Innate and adaptive immune activation in the brain of MPS IIIB mouse model. *J Neurosci Res* 87:978-990.

Drummond, R. A., and G. D. Brown. 2011. The role of Dectin-1 in the host defense against fungal infections. *Curr Opin Microbiol* 14:392-399.

Gatfield, J., and J. Pieters. 2000. Essential role for cholesterol in entry of mycobacteria into macrophages. *Science* 288:1647-1650.

Haraga, A., M. B. Ohlson, and S. I. Miller. 2008. Salmonellae interplay with host cells. *Nat Rev Microbiol* 6:53-66.

Hofmann, E., U. Reichart, C. Gausterer, C. Guelly, D. Meijer, M. Muller, and B. Strobl. 2010. Octamer-binding factor 6 (Oct-6/Pou3f1) is induced by interferon and contributes to dsRNA-mediated transcriptional responses. *BMC Cell Biol* 11:61.

Houghton, A. M., W. O. Hartzell, C. S. Robbins, F. X. Gomis-Ruth, and S. D. Shapiro. 2009. Macrophage elastase kills bacteria within murine macrophages. *Nature* 460:637-641.

Jethwaney, D., M. R. Islam, K. G. Leidal, D. B. de Bernabe, K. P. Campbell, W. M. Nauseef, and B. W. Gibson. 2007. Proteomic analysis of plasma membrane and secretory vesicles from human neutrophils. *Proteome Sci* 5:12.

Jiang, Q., W. Q. Li, F. B. Aiello, K. D. Klarmann, J. R. Keller, and S. K. Durum. 2005. Retroviral transduction of IL-7Ralpha into IL-7Ralpha-/- bone marrow progenitors: correction of lymphoid deficiency and induction of neutrophilia. *Gene Ther* 12:1761-1768.

Kasten, K. R., P. S. Prakash, J. Unsinger, H. S. Goetzman, L. G. England, C. M. Cave, A. P. Seitz, C. N. Mazuski, T. T. Zhou, M. Morre, R. S. Hotchkiss, D. A. Hildeman, and C. C. Caldwell. 2010. Interleukin-7 (IL-7) treatment accelerates neutrophil recruitment through gamma delta T-cell IL-17 production in a murine model of sepsis. *Infect Immun* 78:4714-4722.

Kumar, V., and A. Sharma. 2010. Neutrophils: Cinderella of innate immune system. *Int Immunopharmacol* 10:1325-1334.

Lee, K. H., M. Ono, M. Inui, T. Yuasa, and T. Takai. 2000. Stimulatory function of gp49A, a murine Ig-like receptor, in rat basophilic leukemia cells. *J Immunol* 165:4970-4977.

Li, B., A. P. Castano, T. E. Hudson, B. T. Nowlin, S. L. Lin, J. V. Bonventre, K. D. Swanson, and J. S. Duffield. 2010. The melanoma-associated transmembrane glycoprotein Gpnmb controls trafficking of cellular debris for degradation and is essential for tissue repair. *FASEB J* 24:4767-4781.

Li, H., J. J. Repa, M. A. Valasek, E. P. Beltroy, S. D. Turley, D. C. German, and J. M. Dietschy. 2005. Molecular, anatomical, and biochemical events associated with neurodegeneration in mice with Niemann-Pick type C disease. *J Neuropathol Exp Neurol* 64:323-333.

Liao, G., S. Cheung, J. Galeano, A. X. Ji, Q. Qin, and X. Bi. 2009. Allopregnanolone treatment delays cholesterol accumulation and reduces autophagic/lysosomal dysfunction and inflammation in Npc1-/- mouse brain. *Brain Res* 1270:140-151.

Liao, G., Z. Wen, K. Irizarry, Y. Huang, K. Mitsouras, M. Darmani, T. Leon, L. Shi, and X. Bi. 2010. Abnormal gene expression in cerebellum of Npc1-/- mice during postnatal development. *Brain Res* 1325:128-140.

Loftus, S. K., J. A. Morris, E. D. Carstea, J. Z. Gu, C. Cummings, A. Brown, J. Ellison, K. Ohno, M. A. Rosenfeld, D. A. Tagle, P. G. Pentchev, and W. J. Pavan. 1997. Murine model of Niemann-Pick C disease: mutation in a cholesterol homeostasis gene. *Science* 277:232-235.

Lominadze, G., D. W. Powell, G. C. Luerman, A. J. Link, R. A. Ward, and K. R. McLeish. 2005. Proteomic analysis of human neutrophil granules. *Mol Cell Proteomics* 4:1503-1521.

Lopez, M. E., M. D. Klein, J. Hong, U. J. Dimbil, and M. P. P. Scott. 2012. Neuronal and epithelial cell rescue resolves chronic systemic inflammation in the lipid storage disorder Niemann-Pick C. *Hum Mol Genet* doi: 10.1093/hmg/dds126

Lynn, D. J., G. L. Winsor, C. Chan, N. Richard, M. R. Laird, A. Barsky, J. L. Gardy, F. M. Roche, T. H. Chan, N. Shah, R. Lo, M. Naseer, J. Que, M. Yau, M. Acab, D. Tulpan, M. D. Whiteside, A. Chikatamarla, B. Mah, T. Munzner, K. Hokamp, R. E. Hancock, and F. S. Brinkman. 2008. InnateDB: facilitating systems-level analyses of the mammalian innate immune response. *Mol Syst Biol* 4:218.

Manabe, T., T. Yamane, Y. Higashi, P. G. Pentchev, and K. Suzuki. 1995. Ultrastructural changes in the lung in Niemann-Pick type C mouse. *Virchows Arch* 427:77-83.

Maue, R. A., R. W. Burgess, B. Wang, C. M. Wooley, K. L. Sebum, M. T. Vanier, M. A. Rogers, C. C. Chang, T. Y. Chang, B. T. Harris, D. J. Graber, C. A. Penatti, D. M. Porter, B. S. Szwergold, L. P. Henderson, J. W. Totenhagen, T. P. Trouard, I. A. Borbon, and R. P. Erickson. 2012. A novel mouse model of Niemann-Pick type C disease carrying a D1005G-Npc1 mutation comparable to commonly observed human mutations. *Hum Mol Genet* 21:730-750.

Mollinedo, F. 2003. Human neutrophil granules and exocytosis molecular control. *Immunologia* 22:340-358.

Monack, D. M., D. M. Bouley, and S. Falkow. 2004. *Salmonella typhimurium* persists within macrophages in the mesenteric lymph nodes of chronically infected Nramp1+/+ mice and can be reactivated by IFNgamma neutralization. *J Exp Med* 199:231-241.

Myerowitz, R., D. Lawson, H. Mizukami, Y. Mi, C. J. Tifft, and R. L. Proia. 2002. Molecular pathophysiology in Tay-Sachs and Sandhoff diseases as revealed by gene expression profiling. *Hum Mol Genet* 11:1343-1350.

Nakatsuji, T., and R. L. Gallo. 2011. Antimicrobial Peptides: Old Molecules with New Ideas. *J Invest Dermatol*

Nathan, C. 2006. Neutrophils and immunity: challenges and opportunities. *Nat Rev Immunol* 6:173-182.

Ohmi, K., L. C. Kudo, S. Ryazantsev, H. Z. Zhao, S. L. Karsten, and E. F. Neufeld. 2009. Sanfilippo syndrome type B, a lysosomal storage disease, is also a tauopathy. *Proc Natl Acad Sci USA* 106:8332-8337.

Parikh, S. S., S. A. Litherland, M. J. Clare-Salzler, W. Li, P. A. Gulig, and F. S. Southwick. 2003. CapG(-/-) mice have specific host defense defects that render them more susceptible than CapG(+/+) mice to *Listeria monocytogenes* infection but not to *Salmonella enterica* serovar *Typhimurium* infection. *Infect Immun* 71:6582-6590.

Parra, J., A. D. Klein, J. Castro, M. G. Morales, M. Mosqueira, I. Valencia, V. Cortes, A. Rigotti, and S. Zanlungo. 2011. Npc1 deficiency in the C57BL/6J genetic background enhances Niemann-Pick disease type C spleen pathology. *Biochem Biophys Res Commun* 413:400-406.

Patterson, M. C., D. Vecchio, H. Prady, L. Abel, and J. E. Wraith. 2007. Miglustat for treatment of Niemann-Pick C disease: a randomised controlled study. *Lancet Neurol* 6:765-772.

Porter, F. D., D. E. Scherrer, M. H. Lanier, S. J. Langmade, V. Molugu, S. E. Gale, D. Olzeski, R. Sidhu, D. J. Dietzen, R. Fu, C. A. Wassif, N. M. Yanjanin, S. P. Marso, J. House, C. Vite, J. E. Schaffer, and D. S. Ory. 2010. Cholesterol oxidation products are sensitive and specific blood-based biomarkers for Niemann-Pick C1 disease. *Sci Transl Med* 2:56ra81.

Pressey, S. N., D. A. Smith, A. M. Wong, F. M. Platt, and J. D. Cooper. 2012. Early glial activation, synaptic changes and axonal pathology in the thalamocortical system of Niemann-Pick type C1 mice. *Neurobiol Dis* 45:1086-1100.

Ramirez, C. M., B. Liu, A. M. Taylor, J. J. Repa, D. K. Burns, A. G. Weinberg, S. D. Turley, and J. M. Dietschy. 2010. Weekly cyclodextrin administration normalizes cholesterol metabolism in nearly every organ of the Niemann-Pick type C1 mouse and markedly prolongs life. *Pediatr Res* 68:309-315.

Reddy, J. V., I. G. Ganley, and S. R. Pfeffer. 2006. Clues to neuro-degeneration in Niemann-Pick type C disease from global gene expression profiling. *PLoS One* 1:e19.

Reid, D. M., N. A. Gow, and G. D. Brown. 2009. Pattern recognition: recent insights from Dectin-1. *Curr Opin Immunol* 21:30-37.

Rimkunas, V. M., M. J. Graham, R. M. Crooke, and L. Liscum. 2008. In vivo antisense oligonucleotide reduction of NPC1 expression as a novel mouse model for Niemann Pick type C-associated liver disease. *Hepatology* 47:1504-1512.

Rimkunas, V. M., M. J. Graham, R. M. Crooke, and L. Liscum. 2009. TNF-{alpha} plays a role in hepatocyte apoptosis in Niemann-Pick type C liver disease. *J Lipid Res* 50:327-333.

Rosenbaum, A. I., and F. R. Maxfield. 2011. Niemann-Pick type C disease: molecular mechanisms and potential therapeutic approaches. *J Neurochem* 116:789-795.

Rosenberger, C. M., R. L. Gallo, and B. B. Finlay. 2004. Interplay between antibacterial effectors: a macrophage antimicrobial peptide impairs intracellular *Salmonella* replication. *Proc Natl Acad Sci* USA 101:2422-2427.

Sagiv, Y., K. Hudspeth, J. Manner, N. Schrantz, R. K. Stern, D. Zhou, P. B. Savage, L. Teyton, and A. Bendelac. 2006. Cutting edge: impaired glycosphingolipid trafficking and NKT cell development in mice lacking Niemann-Pick type C1 protein. *J Immunol* 177:26-30.

Samuel, B. U., N. Mohandas, T. Harrison, H. McManus, W. Rosse, M. Reid, and K. Haldar. 2001. The role of cholesterol and glycosylphosphatidylinositol-anchored proteins of erythrocyte rafts in regulating raft protein content and malarial infection. *J Biol Chem* 276:29319-29329.

Sayre, N. L., V. M. Rimkunas, M. J. Graham, R. M. Crooke, and L. Liscum. 2010. Recovery from liver disease in a Niemann-Pick type C mouse model. *J Lipid Res* 51:2372-2383.

Schrantz, N., Y. Sagiv, Y. Liu, P. B. Savage, A. Bendelac, and L. Teyton. 2007. The Niemann-Pick type C2 protein loads isoglobotrihexosylceramide onto CD1d molecules and contributes to the thymic selection of NKT cells. *J Exp Med* 204:841-852.

Segal, A. W. 2005. How neutrophils kill microbes. *Annu Rev Immunol* 23:197-223.

Silverstein, E., and J. Friedland. 1977. Elevated serum and spleen angiotensin converting enzyme and serum lysozyme in Gaucher's disease. *Clin Chim Acta* 74:21-25.

Smith, D., K. L. Wallom, I. M. Williams, M. Jeyakumar, and F. M. Platt. 2009.

Beneficial effects of anti-inflammatory therapy in a mouse model of Niemann-Pick disease type C1. *Neurobiol Dis* 36:242-251.

Tang, Y., I. C. Leao, E. M. Coleman, R. S. Broughton, and J. E. Hildreth. 2009. Deficiency of niemann-pick type C-1 protein impairs release of human immunodeficiency virus type 1 and results in Gag accumulation in late endosomal/lysosomal compartments. *J Virol* 83:7982-7995.

Trexler, A. J., and M. R. Nilsson. 2007. The formation of amyloid fibrils from proteins in the lysozyme family. *Curr Protein Pept Sci* 8:537-557.

Tsolis, R. M., R. A. Kingsley, S. M. Townsend, T. A. Ficht, L. G. Adams, and A. J. Baumler. 1999. Of mice, calves, and men. Comparison of the mouse typhoid model with other *Salmonella* infections. *Adv Exp Med Biol* 473:261-274.

Vance, J. E., and K. B. Peake. 2011. Function of the Niemann-Pick type C proteins and their bypass by cyclodextrin. *Curr Opin Lipidol* 22:204-209.

Vanier, M. T. 2010. Niemann-Pick disease type C. *Orphanet J Rare Dis* 5:16.

Vassiloyanakopoulos, A. P., S. Okamoto, and J. Fierer. 1998. The crucial role of polymorphonuclear leukocytes in resistance to *Salmonella* dublin infections in genetically susceptible and resistant mice. *Proc Natl Acad Sci USA* 95:7676-7681.

Vazquez, M. C., T. Del Pozo, F. A. Robledo, G. Carrasco, L. Pavez, F. Olivares, M. Gonzalez, and S. Zanlungo. 2011. Alteration of gene expression profile in niemann-pick type C mice correlates with tissue damage and oxidative stress. *PLoS One* 6:e28777.

Vieira, M. N., L. Forny-Germano, L. M. Saraiva, A. Sebollela, A. M. Martinez, J. C. Houzel, F. G. De Felice, and S. T. Ferreira. 2007. Soluble oligomers from a non-disease related protein mimic Abeta-induced tau hyperphosphorylation and neurodegeneration. *J Neurochem* 103:736-748.

Vitner, E. B., H. Dekel, H. Zigdon, T. Shachar, T. Farfel-Becker, R. Eilam, S. Karlsson, and A. H. Futerman. 2010. Altered expression and distribution of cathepsins in neuronopathic forms of Gaucher disease and in other sphingolipidoses. *Hum Mol Genet* 19:3583-3590.

Watarai, M., S. Makino, M. Michikawa, K. Yanagisawa, S. Murakami, and T. Shirahata. 2002. Macrophage plasma membrane cholesterol contributes to *Brucella abortus* infection of mice. *Infect Immun* 70:4818-4825.

Weinrauch, Y., D. Drujan, S. D. Shapiro, J. Weiss, and A. Zychlinsky. 2002. Neutrophil elastase targets virulence factors of enterobacteria. *Nature* 417:91-94.

Wraith, J. E., M. R. Baumgartner, B. Bembi, A. Covanis, T. Levade, E. Mengel, M. Pineda, F. Sedel, M. Topcu, M. T. Vanier, H. Widner, F. A. Wijburg, and M. C. Patterson. 2009. Recommendations on the diagnosis and management of Niemann-Pick disease type C. *Mol Genet Metab* 98:152-165.

Xie, X., M. S. Brown, J. M. Shelton, J. A. Richardson, J. L. Goldstein, and G. Liang. 2011. Amino acid substitution in NPC1 that abolishes cholesterol binding reproduces phenotype of complete NPC1 deficiency in mice. *Proc Natl Acad Sci USA* 108:15330-15335.

Yanjanin, N. M., J. I. Velez, A. Gropman, K. King, S. E. Bianconi, S. K. Conley, C. C. Brewer, B. Solomon, W. J. Pavan, M. Arcos-Burgos, M. C. Patterson, and F. D. Porter. 2010. Linear clinical progression, independent of age of onset, in Niemann-Pick disease, type C. *Am J Med Genet B Neuropsychiatr Genet* 153B:132-140.

What is claimed is:

1. A method for detecting an increased probability or risk of neurodegeneration caused by Niemann-Pick disease in a subject and treating said subject comprising detecting lysozyme and cathepsin S levels in a sample from the subject, wherein an increased ratio of lysozyme:cathepsin S levels in the subject compared to the ratio of lysozyme: cathepsin S levels in a control subject sample indicates an increased probability or risk of the neurodegeneration; and administering to the subject an effective amount of a drug for the treatment of the neurodegeneration in the subject;

wherein the drug comprises hydroxy propyl beta cyclodextrin (HPBCD).

2. The method of claim 1, wherein the Niemann-Pick disease is selected from the group consisting of Niemann-Pick Disease, Type A, Niemann-Pick Disease, Type B, and Niemann-Pick Disease, Type C.

3. The method of claim 1, wherein the subject is a mammal selected from the group consisting of humans, primates, monkeys, chimpanzees, dogs, cats, sheep, cattle, goats, pigs, horses, chickens, mice, rats, rabbits, and guinea pigs.

4. The method of claim 1, wherein the drug further comprises Vorinostat.

5. A method for detecting an increased probability or risk of neurodegeneration caused by Niemann-Pick disease in a subject and treating said subject comprising detecting in a sample from the subject lysozyme and cathepsin S levels, wherein an increased ratio of cathepsin S:lysozyme in the subject compared to the ratio of cathepsin S:lysozyme in a control subject sample indicates an increased probability or risk of neurodegeneration; and administering to the subject an effective amount of a drug for the treatment of the neurodegeneration in the subject;

wherein the drug comprises hydroxy propyl beta cyclodextrin (HPBCD).

6. The method of claim 5 wherein the Niemann-Pick disease is selected from the group consisting of Niemann-Pick Disease, Type A, Niemann-Pick Disease, Type B, and Niemann-Pick Disease, Type C.

7. The method of claim 5 wherein the subject is a mammal selected from the group consisting of humans, primates, monkeys, chimpanzees, dogs, cats, sheep, cattle, goats, pigs, horses, chickens, mice, rats, rabbits, and guinea pigs.

8. The method of claim 5 wherein the drug further comprises Vorinostat.

* * * * *